US012760039B2

(12) United States Patent
Williams, Sr.

(10) Patent No.: US 12,760,039 B2
(45) **Date of Patent: *Oct. 13, 2026**

(54) ANTI-INFLAMMATORY COMPOUNDS, PHARMACEUTICAL COMPOSITIONS, AND METHODS OF TREATING HEMOCHROMATOSIS, AND OTHER DISORDERS

(71) Applicant: Miralogx LLC, Tampa, FL (US)

(72) Inventor: Jonnie R. Williams, Sr., Sarasota, FL (US)

(73) Assignee: Miralogx LLC, Tampa, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 19/062,919

(22) Filed: Feb. 25, 2025

(65) Prior Publication Data

US 2026/0258056 A1 Sep. 3, 2026

Related U.S. Application Data

(63) Continuation-in-part of application No. PCT/US2023/073106, filed on Aug. 29, 2023.

(60) Provisional application No. 63/458,611, filed on Apr. 11, 2023, provisional application No. 63/403,536, filed on Sep. 2, 2022.

(51) Int. Cl.

| | |
|---|---|
| ***A61K 31/555*** | (2006.01) |
| ***C07D 471/20*** | (2006.01) |
| ***C07D 471/22*** | (2006.01) |
| ***C07D 487/22*** | (2006.01) |
| ***C07F 1/10*** | (2006.01) |
| ***C07F 3/06*** | (2006.01) |

(52) U.S. Cl.

CPC .............. *C07F 3/06* (2013.01); *A61K 31/555* (2013.01); *C07D 471/20* (2013.01); *C07D 471/22* (2013.01); *C07D 487/22* (2013.01); *C07F 1/10* (2013.01)

(58) Field of Classification Search

CPC .............. A61K 31/555; A61K 31/4439; A61K 31/497; C07D 213/53; C07D 241/12

See application file for complete search history.

(56) References Cited

U.S. PATENT DOCUMENTS

| | | | | |
|---|---|---|---|---|
| 4,540,790 A * | 9/1985 | Schmidt | C07D 213/55 546/276.4 |
| 2023/0295125 A1* | 9/2023 | Williams, Sr. | A61P 35/00 |
| 2025/0282758 A1* | 9/2025 | Williams, Sr. | A61P 35/00 |

FOREIGN PATENT DOCUMENTS

| | | | |
|---|---|---|---|
| WO | 2004/004730 A2 | 1/2004 | |
| WO | WO-2022082079 A1 * | 4/2022 | C07D 401/04 |
| WO | WO-2022147496 A1 * | 7/2022 | C12Q 1/004 |
| WO | WO-2023096854 A1 * | 6/2023 | C07D 401/14 |

OTHER PUBLICATIONS

J. Brecher, Graphical Representation Standards for Chemical Structure Diagrams (IUPAC Recommendations 2008), 80 Pure Appl. Chem. 277-410 (2008) (Year: 2008).*

D. Pufky-Heinrich et al., 81 Heterocycles, 1811-1825 (2010) (Year: 2010).*

R. Rowe et al., Handbook of Pharmaceutical Excipients, pp. 253-255 (6th ed., 2009) (Year: 2009).*

PubChem CID 69856580 (2012) (Year: 2012).*

PubChem CID 125294604 (2017) (Year: 2017).*

S. Mandal et al., 11 Journal of the Chemical Society, Chemical Communications, 744-746 (1989) (Year: 1989).*

Faouzi, M., et al. "Acidic Cannabinoids Suppress Proinflammatory Cytokine Release by Blocking Store-Operated Calcium Entry." Function, vol. 3, No. 4, Oxford University Press (OUP), 2022. doi:10.1093/function/zqac033.

Suzuki, S., et al. "Cannabigerolic Acid (CBGA) Inhibits the TRPM7 Ion Channel Through Its Kinase Domain." Function, vol. 5, No. 1, Oxford University Press (OUP), Nov. 23, 2023. doi:10.1093/function/zqad069.

Sun, Y., et al. "TRPM7 and Its Role in Neurodegenerative Diseases." Channels, vol. 9, No. 5, Informa UK Limited, Sep. 1, 2015, pp. 253-261. doi:10.1080/19336950.2015.1075675.

Doyle, C.A. et al. "Endosomal Fusion of pH-Dependent Enveloped Viruses Requires Ion Channel TRPM7." Nature Communications, vol. 15, No. 1, Springer Science and Business Media LLC, Oct. 1, 2024. doi:10.1038/s41467-024-52773-w.

Pubmed Compound Record for CID69856580 '2-6-bis(1H-imidazol-2-yl)pyrazine', U.S. National Library of Medicine, Dec. 1, 2012 (Dec. 1, 2012), pp. 1-10 (https://pubchem.ncbi.nlm.nih.gov/compound/69856580); p. 2.

Feb. 22, 2024—International Search Report and Written Opinion of ISA—PCT/US2023/073106.

* cited by examiner

*Primary Examiner* — Alexander R Pagano

(74) *Attorney, Agent, or Firm* — KellDann Law PLLC; Paul M. Rivard

(57) ABSTRACT

Pharmaceutical compounds have anti-inflammatory activity. A pharmaceutical composition may include a therapeutically effective amount of the compound(s) and a pharmaceutically acceptable vehicle. A method of treating hemochromatosis, hyperammonemia, or a disorder associated with chronic inflammation or a cancer, involves administering the pharmaceutical composition to an individual in need thereof. In another aspect, a method of inhibiting formation of metal oxides or reducing metal reactivity comprises contacting a metal with an effective amount of the compound(s).

13 Claims, 29 Drawing Sheets

| # | MEAS. RET | AREA | AREA % |
|---|---|---|---|
| 1 | 18.414 | 8.780 | 0.251 |
| 2 | 18.552 | 0.015 | 0.000 |
| 3 | 19.443 | 124.143 | 3.545 |
| 4 | 19.907 | 178.505 | 5.098 |
| 5 | 20.230 | 0.745 | 0.021 |
| 6 | 21.065 | 2420.964 | 69.140 |
| 7 | 21.439 | 748.613 | 21.379 |
| 8 | 32.645 | 12.156 | 0.347 |
| 9 | 35.045 | 7.639 | 0.218 |

A: NORMAL HPLC

B: CHIRAL HPLC

TRISOMINE PEAK 2

TRISOMINE PEAK 1

| | VCAM TRI-ISO-1 | VCAM DOXYCYCLINE |
|---|---|---|
| IC50 | 67.65 | 134231 |

| | VCAM TRI-ISO-1 | VCAM DOXYCYCLINE |
|---|---|---|
| R SQUARED | 0.9944 | 0.9989 |

[dien·Fe]$^{2+}$

[D102·Fe]$^{2+}$ $^{1}$H-NMR (700 MHz, DMSO-$d_6$)

$^{13}$C-NMR (176 MHz, DMSO-$d_6$)

$^1$H-NMR (700 MHz, DMSO-$d_6$)

$^{13}$C-NMR (176 MHz, DMSO-$d_6$)

ANTI-INFLAMMATORY COMPOUNDS, PHARMACEUTICAL COMPOSITIONS, AND METHODS OF TREATING HEMOCHROMATOSIS, AND OTHER DISORDERS

CROSS-REFERENCE TO RELATED APPLICATIONS

This application is a continuation-in-part of International App. No. PCT/US2023/073106, filed Aug. 23, 2023, which claims priority under 35 U.S.C. § 119(e) to U.S. App. No. 63/458,611, filed Apr. 11, 2023, and U.S. App. No. 63/403,536, filed Sep. 2, 2022, the disclosure of each of which is hereby incorporated by reference in its entirety.

BACKGROUND

Metal overload or imbalances are associated with a wide range of diseases and pathological conditions. For example, Hereditary Hemochromatosis (HH) is a primary iron overload (IO) condition. A mutation in the HFE (hereditary hemochromatosis) protein causes increased intestinal absorption of iron despite a normal dietary intake, leading to an abundance of iron deposition in the body, particularly in the liver, pancreas, heart, thyroid, pituitary gland, and joints. Excess iron deposition, if left untreated, causes tissue damage and fibrosis with the potential for hepatic cirrhosis, diabetes, arthropathy, congestive heart failure, hypogonadism, and skin hyperpigmentation. Excess iron deposition is also associated with inflammatory conditions, chronic kidney disease, rheumatoid arthritis, autoimmune disease, acute infections, cancer, anemia of chronic disease, type 2 diabetes, metabolic syndromes, atherosclerosis, fatty liver disease, anorexia, Grave's disease, arrhythmias, and chronic hepatitis C infection.

The current standard of care for HH is phlebotomy. By drawing off red blood cells, the major mobilizer of iron in the body, iron toxicity can be minimized. Patients may require more than 100 phlebotomies of 500 mL each to reduce iron levels to normal.

In addition to HH, there is another form of hemochromatosis known as secondary hemochromatosis which can occur in patients who have hemoglobinopathies (e.g., sickle cell disease, thalassemia, and sideroblastic anemias), congenital hemolytic anemias, and myelodysplasia. In patients with secondary hemochromatosis (also known as secondary iron overload), iron overload results from increased iron absorption, exogenous iron given to treat anemia, and repeated blood transfusions.

Secondary hemochromatosis is usually treated with iron chelators such as deferoxamine or deferasirox, but unfortunately, these therapies, can be complex to administer, require an unusual time commitment from patients, and/or are associated with adverse effects such as hypotension, GI disturbances, vision and hearing loss, and abnormal liver and kidney function. Thus, there is also a need for an alternative therapeutic approach for patients with secondary hemochromatosis.

Absolute telomere length (ATL) shortening is a key molecular feature of cellular aging and DNA damage associated with chronic diseases and mortality. Indeed, telomere shortening has been discovered to be the primary cause of human aging. In particular, reduced ATL has been associated with almost all chronic diseases related to aging such as cancer, heart disease, diabetes, and autoimmune diseases.

Telomeres are the end part of the chromosomes, and serve to protect the DNA just like shoelace tips preserve a shoelace from unraveling. When the telomeres shorten to critical lengths, the DNA is no longer protected during replication, resulting DNA damage and chromosomal rearrangements, which in turn lead to senescence, apoptosis, or oncogenic transformation of somatic cells. Accordingly, there is a need for therapeutic approaches for preventing ATL shortening and elongating telomeres.

Hyperammonemia is a metabolic disturbance characterized by an excess of ammonia in the blood. It is a dangerous condition that may lead to brain injury and death. It may be primary or secondary. Treatment of severe hyperammonemia (serum ammonia levels greater than 1000 μmol/L) should begin with hemodialysis if it is otherwise medically appropriate and tolerated.

Ammonia is a nitrogenous product of the catabolism of protein. It is converted to the less toxic substance urea prior to excretion in urine by the kidneys. The metabolic pathways that synthesize urea involve reactions that start in the mitochondria and then move into the cytosol. The process is known as the urea cycle, which comprises several enzymes acting in sequence. It is greatly exacerbated by common zinc deficiency, which raises ammonia levels further.

Hyperammonemia is one of the metabolic derangements that contribute to hepatic encephalopathy, which can cause swelling of astrocytes and stimulation of NMDA-receptors in the brain. Overstimulation of NMDA-receptors induces excitotoxicity.

Acquired hyperammonemia is usually caused by diseases that result in either acute liver failure, such as overwhelming hepatitis B or exposure to hepatoxins, or cirrhosis of the liver with chronic liver failure. Chronic hepatitis B, chronic hepatitis C, and excessive alcohol consumption are common causes of cirrhosis. The physiologic consequences of cirrhosis include shunting of blood from the liver to the inferior vena cava, resulting in decreased filtration of blood and removal of nitrogen-containing toxins by the liver, and then hyperammonemia. This type of hyperammonemia can be treated with antibiotics to kill the bacteria that initially produce the ammonia, though this does not work as well as removal of protein from the colon prior to its digestion to ammonia, achieved by lactulose administration for frequent (3-4 per day) bowel movements.

Medication induced hyperammonemia can occur with valproic acid overdose, and is due to a deficiency in carnitine. Its treatment is carnitine replacement.

Hyperammonemia can also be a severe side effect of chemotherapy of cancer.

Severe dehydration and small intestinal bacterial overgrowth can also lead to acquired hyperammonemia.

Glycine toxicity causes hyperammonemia, which manifests as CNS symptoms and nausea. Transient blindness can also occur.

Congenital hyperammonemia is usually due to genetic defects in one of the enzymes of the urea cycle, such as ornithine transcarbamylase deficiency, which leads to lower production of urea from ammonia.

Treatment centers on limiting intake of ammonia and increasing its excretion. Dietary protein, a metabolic source of ammonium, is restricted and caloric intake is provided by glucose and fat. Intravenous arginine (argininosuccinase deficiency), sodium phenylbutyrate and sodium benzoate (ornithine transcarbamoylase deficiency) are pharmacologic agents commonly used as adjunctive therapy to treat hyperammonemia in patients with urea cycle enzyme deficiencies. Sodium phenylbutyrate and sodium benzoate can serve as alternatives to urea for the excretion of waste nitrogen. Phenylbutyrate, which is the product of phenylacetate, conjugates with glutamine to form phenylacetylglutamine, which is excreted by the kidneys. Similarly, sodium benzoate reduces ammonia content in the blood by conjugating with glycine to form hippuric acid, which is rapidly excreted by the kidneys. A preparation containing sodium phenylacetate and sodium benzoate is available under the trade name Ammonul. Acidification of the intestinal lumen using lactulose can decrease ammonia levels by protonating ammonia and trapping it in the stool. This is a treatment for hepatic encephalopathy.

Many common over-the-counter and prescription drugs also can contribute to increased ammonia levels, typically as a result of increased nitrite production. It would be desirable to develop anti-inflammatory compounds which have the effect of decreasing ammonia levels in an individual. It would be particularly desirable to develop treatment therapies which are effective for treating hyperammonemia as well as other disorders associated with chronic inflammation, and cancer.

The present invention addresses the needs for alternative therapeutic approaches for treating conditions associated with metal overload, autoimmune or anti-inflammatory conditions, hemochromatosis, telomere shortening, hyperammonemia, cancer etc.

SUMMARY

In one aspect, the present disclosure relates to a compound having a structure according to Formula Ia or Formula Ib set forth below:

Formula Ia

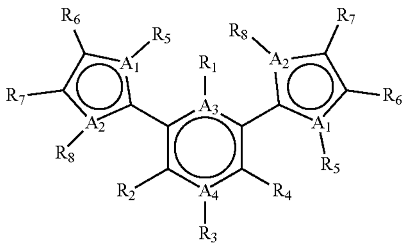

Formula Ib

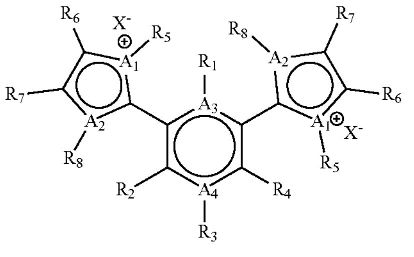

or a pharmaceutically acceptable ester or solvate thereof, wherein $X^-$ is an ion of an acid forming a pharmaceutically acceptable salt, where $A_1$, $A_2$, $A_3$, and $A_4$ are independently selected from nitrogen (N) or Carbon (C), wherein $R_1$, $R_2$, $R_3$, $R_4$, $R_5$, $R_6$, $R_7$, and $R_8$ are independently selected from the group consisting of nothing, H, OH, protected hydroxyl, alkyl, alkenyl, alkynyl, acyl, aryl, heteroaryl, cycloalkyl, and heterocycle; wherein $R_1$ is nothing if $A_3$ is N; wherein $R_3$ is nothing if $A_4$ is N; wherein the alkyl, alkenyl, alkynyl or acyl is optionally substituted with one or more substituents independently selected from the group consisting of halogen, —OH, alkyl, —O-alkyl, $NR^AR^B$, —S-alkyl, —SO-alkyl, —$SO_2$-alkyl, alkenyl, alkynyl, aryl, heteroaryl, cycloalkyl, and heterocycle; wherein $R^A$ and $R^B$ are each independently selected from hydrogen and $C_{1-4}$ alkyl; wherein the aryl or heteroaryl, whether alone or as part of a substituent group, is optionally substituted with one or more substituents independently selected from the group consisting of halogen, —OH, alkyl, —O-alkyl, —COH, —C(O)—$C_{1-4}$ alkyl, —C(O)O—$C_{1-4}$ alkyl, $NR^CR^D$, —S-alkyl, —SO-alkyl and —$SO_2$-alkyl; wherein $R^C$ and $R^D$ are each independently selected from hydrogen and $C_{1-4}$ alkyl.

In some embodiments, $R_2$ and/or $R_4$ has the structure according to Formula IIa or Formula IIb:

Formula IIa

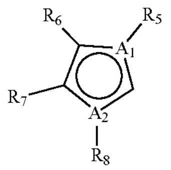

Formula IIb

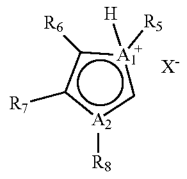

wherein $X^-$, $A_1$, $A_2$, $R_5$, $R_6$, $R_7$, and $R_8$ are defined as above.

In some embodiments, $A_1$ and $A_3$ are N, $A_4$ is C, and $R_3$ has the structure according to Formula IIa or Formula IIb.

In some embodiments, $A_2$ is C.

In some embodiments, $A_1$ is N, and/or $A_3$ and/or $A_4$ is N.

In some embodiments, $A_2$ is C.

In some embodiments, $R_2$ and $R_4$ have the structure according to Formula IIa or Formula IIb.

In some embodiments, the compound has the structure:

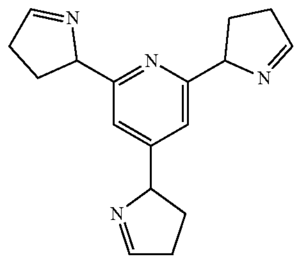 [SMILES: C1=NC(c2cc(C3CCC=N3)nc(C3CCC=N3)c2)CC1]

or a pharmaceutically acceptable salt, ester or solvate thereof.

In some embodiments, the compound is not

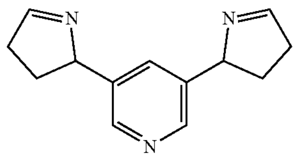

3,5-bis(3,4-dihydro-2H-pyrrol-2-yl)pyridine or a pharmaceutically acceptable salt, ester or solvate thereof.

In some embodiments, the compound has a structure selected from the group consisting of:

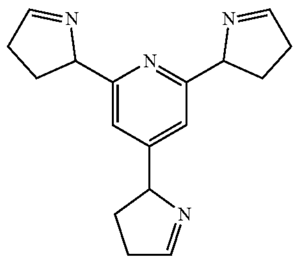

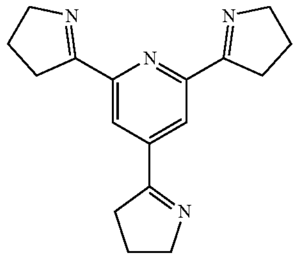

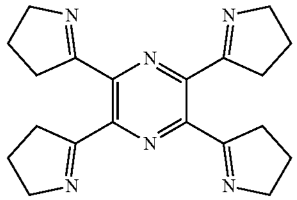

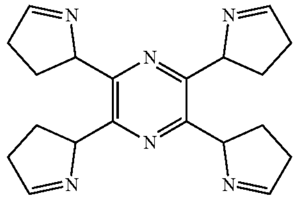

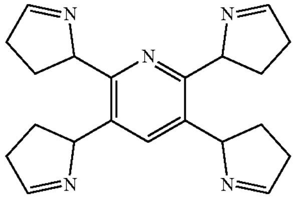

and

-continued

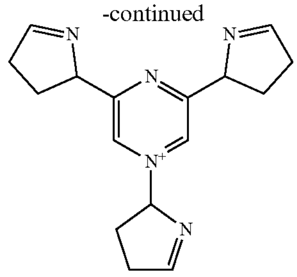

or a pharmaceutically acceptable salt, ester or solvate thereof.

According to one aspect, an anti-inflammatory compound has the structure:

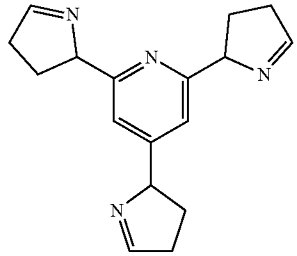 [SMILES: C1=NC(c2cc(C3CCC=N3)nc(C3CCC=N3)c2)CC1]

or a pharmaceutically acceptable salt, ester or solvate thereof.

In some embodiments, the present disclosure relates to a compound having a structure according to Formula IIIa or Formula IIIb set forth below:

Formula IIIa

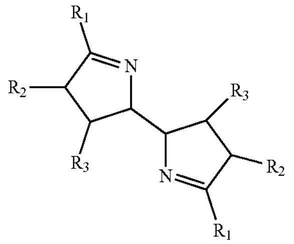

Formula IIIb

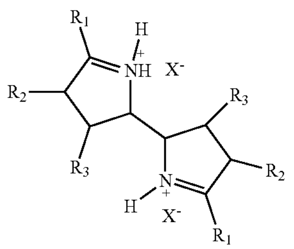

or a pharmaceutically acceptable ester or solvate thereof, wherein $X^-$ is an ion of an acid forming a pharmaceutically acceptable salt, wherein $R_1$, $R_2$, and $R_3$ are independently selected from the group consisting of H, OH, protected hydroxyl, alkyl, alkenyl, alkynyl, acyl, aryl, heteroaryl, cycloalkyl, and heterocycle; wherein the alkyl, alkenyl, alkynyl or acyl is optionally substituted with one or more substituents independently selected from the group consisting of halogen, —OH, alkyl, —O-alkyl, $NR^AR^B$, —S-alkyl, —SO-alkyl, —$SO_2$-alkyl, alkenyl, alkynyl, aryl, heteroaryl, cycloalkyl, and heterocycle; wherein $R^A$ and $R^B$ are each independently selected from hydrogen and $C_{1-4}$ alkyl; wherein the aryl or heteroaryl, whether alone or as part of a substituent group, is optionally substituted with one or more substituents independently selected from the group consisting of halogen, —OH, alkyl, —O-alkyl, —COH, —C(O)—$C_{1-4}$ alkyl, —C(O)O—$C_{1-4}$ alkyl, $NR^CR^D$, —S-alkyl, —SO-alkyl and —$SO_2$-alkyl; wherein $R^C$ and $R^D$ are each independently selected from hydrogen and $C_{1-4}$ alkyl.

In some embodiments, the compound has the following structure:

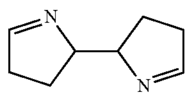

or a pharmaceutically acceptable salt, ester or solvate thereof.

In some embodiments, the present disclosure relates to a compound having a structure according to Formula IVa or Formula IVb set forth below:

Formula IVa

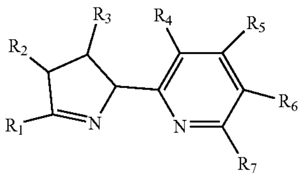

Formula IVb

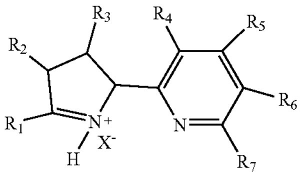

or a pharmaceutically acceptable ester or solvate thereof, wherein $X^-$ is an ion of an acid forming a pharmaceutically acceptable salt, wherein $R_1$, $R_2$, $R_3$, $R_4$, $R_5$, $R_6$, and $R_7$ are independently selected from the group consisting of H, OH, protected hydroxyl, alkyl, alkenyl, alkynyl, acyl, aryl, heteroaryl, cycloalkyl, and heterocycle; wherein the alkyl, alkenyl, alkynyl or acyl is optionally substituted with one or more substituents independently selected from the group consisting of halogen, —OH, alkyl, —O-alkyl, $NR^AR^B$, —S-alkyl, —SO-alkyl, —$SO_2$-alkyl, alkenyl, alkynyl, aryl, heteroaryl, cycloalkyl, and heterocycle; wherein $R^A$ and $R^B$ are each independently selected from hydrogen and $C_{1-4}$ alkyl; wherein the aryl or heteroaryl, whether alone or as part of a substituent group, is optionally substituted with one or more substituents independently selected from the group consisting of halogen, —OH, alkyl, —O-alkyl, —COOH, —C(O)—$C_{1-4}$ alkyl, —C(O)O—$C_{1-4}$ alkyl, $NR^CR^D$, —S-alkyl, —SO-alkyl and —$SO_2$-alkyl; wherein $R^C$ and $R^D$ are each independently selected from hydrogen and $C_{1-4}$ alkyl.

In some embodiments, the compound has the following structure:

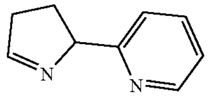

, or a pharmaceutically acceptable salt, ester or solvate thereof.

In another aspect, the present disclosure relates to a compound having a structure according to Formula Va or Formula Vb set forth below:

Formula Va

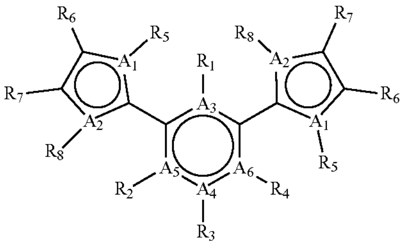

Formula Vb

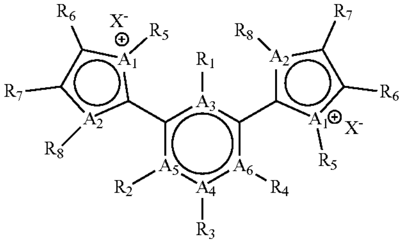

or a pharmaceutically acceptable ester or solvate thereof, wherein $X^-$ is an ion of an acid forming a pharmaceutically acceptable salt, where $A_1$, $A_2$, $A_3$, $A_4$, $A_5$, and $A_6$ are independently selected from nitrogen (N) or Carbon (C), wherein $R_1$, $R_2$, $R_3$, $R_4$, $R_5$, $R_6$, $R_7$, and $R_8$ are independently selected from the group consisting of nothing, H, OH, protected hydroxyl, alkyl, alkenyl, alkynyl, acyl, aryl, heteroaryl, cycloalkyl, and heterocycle; wherein $R_1$ is nothing if $A_3$ is N; wherein $R_3$ is nothing if $A_4$ is N; wherein the alkyl, alkenyl, alkynyl or acyl is optionally substituted with one or more substituents independently selected from the group consisting of halogen, —OH, alkyl, —O-alkyl, $NR^AR^B$, —S-alkyl, —SO-alkyl, —$SO_2$-alkyl, alkenyl, alkynyl, aryl, heteroaryl, cycloalkyl, and heterocycle; wherein $R^A$ and $R^B$ are each independently selected from hydrogen and $C_{1-4}$ alkyl; wherein the aryl or heteroaryl, whether alone or as part of a substituent group, is optionally substituted with one or more substituents independently selected from the group consisting of halogen, —OH, alkyl, —O-alkyl, —COH, —C(O)—$C_{1-4}$ alkyl, —C(O)O—$C_{1-4}$ alkyl, $NR^CR^D$, —S-alkyl, —SO-alkyl and —$SO_2$-alkyl; wherein $R^C$ and $R^D$ are each independently selected from hydrogen and $C_{1-4}$ alkyl. In some embodiments, $R_2$ and/or $R_4$ has the structure according to Formula IIa or Formula IIb, and wherein $X^-$, $A_1$, $A_2$, $R_5$, $R_6$, $R_7$, and $R_8$ are defined as above. In some embodiments, $A_1$ and $A_3$ are N, $A_4$, $A_5$, and $A_6$ are C, and $R_3$ has the structure according to Formula IIa or Formula IIb. In some embodiments, $A_1$ and $A_3$ are N, $A_4$ is C, $A_5$ or $A_6$ is N and $R_3$ has the structure according to Formula IIa or Formula IIb. In some embodiments, $A_1$, $A_3$, and $A_4$ are N, $A_5$ and $A_6$ are C, and $R_3$ has the structure according to Formula IIa or Formula IIb. In some embodiments, $A_2$ is C. In some embodiments, $A_1$ is N, and/or $A_3$ and/or $A_4$ is N. In some embodiments, $R_2$ and $R_4$ have the structure according to Formula IIa or Formula IIb.

In some embodiments, the compound according to formula Va or Vb has the structure:

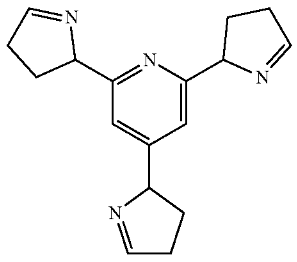 [SMILES: C1=NC(c2cc(C3CCC=N3)nc(C3CCC=N3)c2)CC1]

or a pharmaceutically acceptable salt, ester or solvate thereof.

In some embodiments, the compound according to formula Va or Vb has a structure selected from the group consisting of:

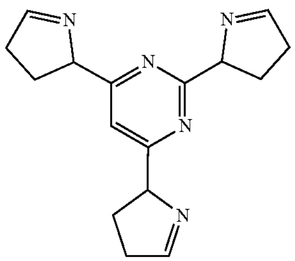

and

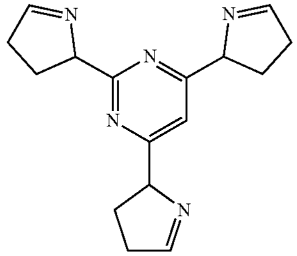 [SMILES: C1=NC(c2c[n+](C3CCC=N3)cc(C3CCC=N3)n2)CC1]

or a pharmaceutically acceptable salt, ester or solvate thereof.

In some embodiments, the compound according to formula Va or Vb has the structure:

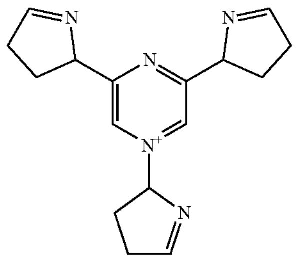 [SMILES: C1=NC(c2c[n+](C3CCC=N3)cc(C3CCC=N3)n2)CC1]

or a pharmaceutically acceptable salt, ester or solvate thereof.

In some embodiments, the compound according to formula Va or Vb has a structure selected from the group consisting of:

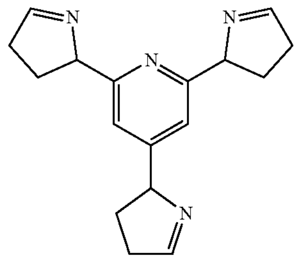

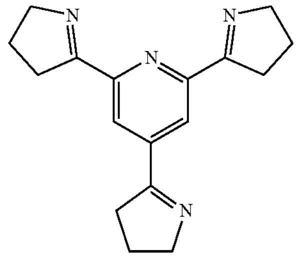

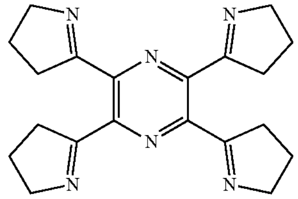

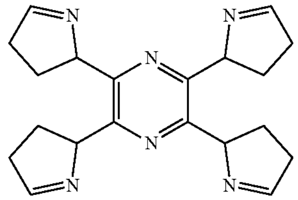

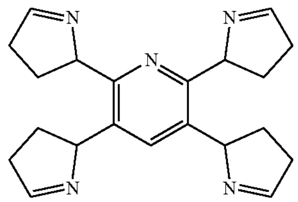

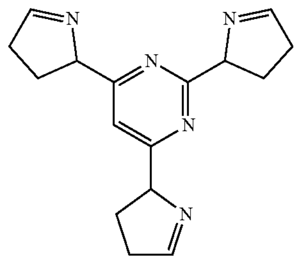

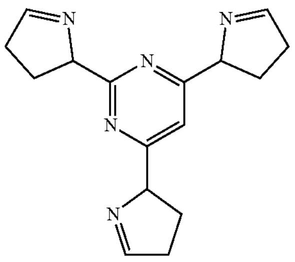

and

-continued

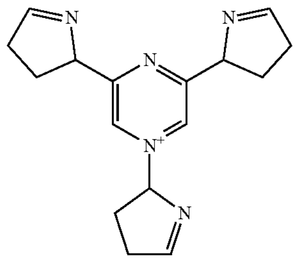

or a pharmaceutically acceptable salt, ester or solvate thereof.

In some embodiments, the compound according to formula Va or Vb has a structure selected from the group consisting of:

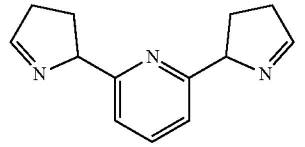

and

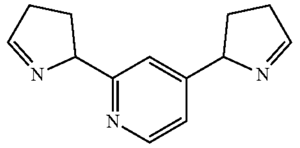

or a pharmaceutically acceptable salt, ester or solvate thereof.

In another aspect, the present disclosure relates to a compound having a structure according to Formula VIa, Formula VIb or Formula VIc set forth below:

Formula VIa

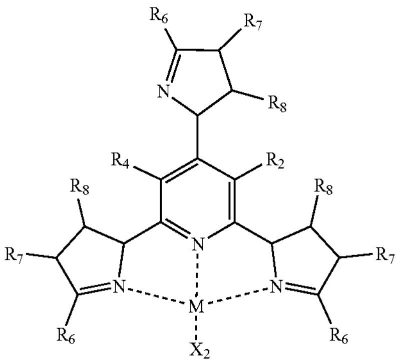

-continued

Formula VIb

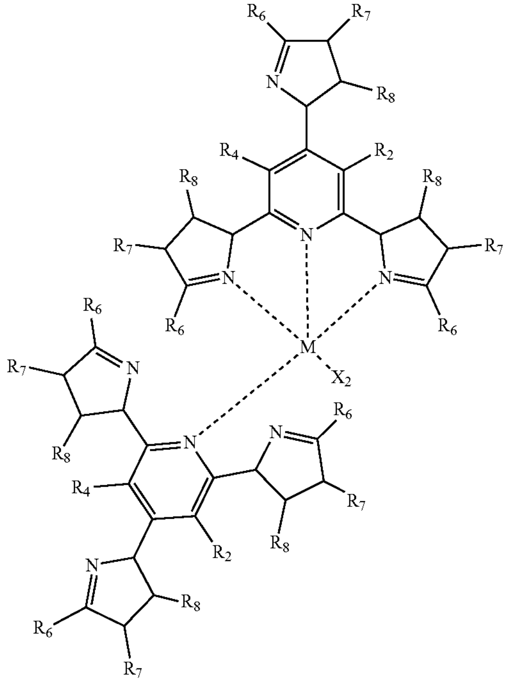

Formula VIc

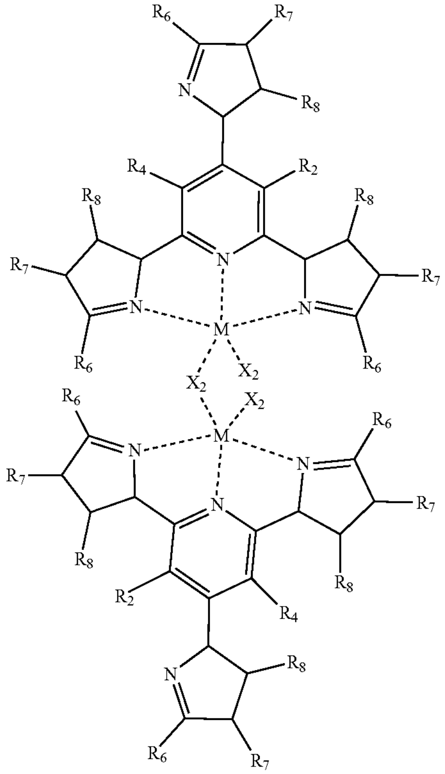

wherein each $R_2$, $R_4$, $R_6$ $R_7$, and $R_8$ is independently as previously defined, each $X_2$ is independently an ion of an acid forming a pharmaceutically acceptable salt, and each M is independently a transition metal selected from the group consisting of scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, and gold.

In some embodiments, a compound according to Formula VIa, VIb or VIc has a structure selected from the group consisting of:

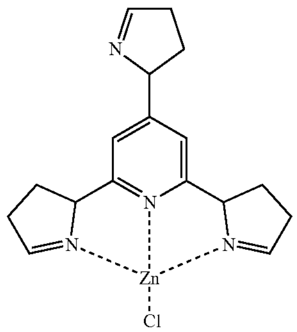

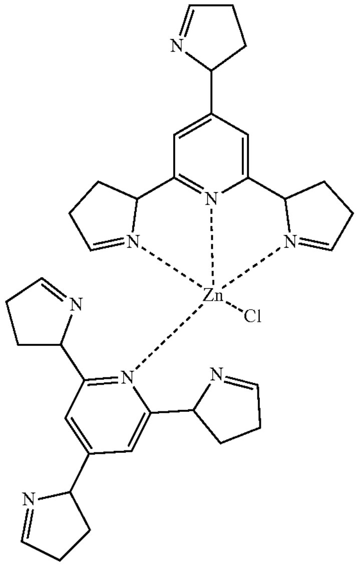

and

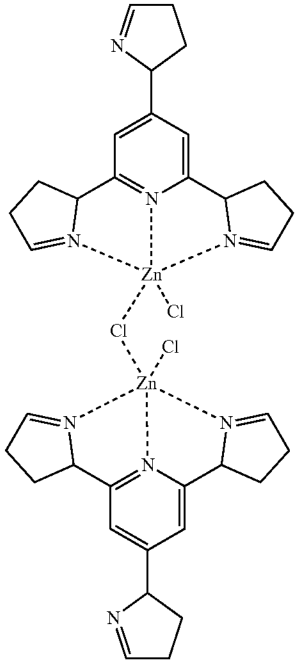

In another aspect, the present disclosure relates to a compound having a structure according to Formula VII set forth below:

Formula VII

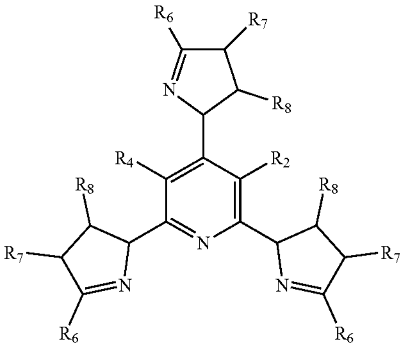

wherein $R_2$ and $R_4$ are independently H, halogen, or a calcium ion chelator group, with the proviso that $R_2$ and $R_4$ are not both hydrogen; and each $R_6$, $R_7$ and $R_8$ is independently as previously defined;

or a pharmaceutically acceptable salt, ester or solvate thereof.

In some examples of compounds of Formula VII, $R_2$ and $R_4$ are each independently H, F, a residue of carboxylic acid (—COOH), carboxylate (—COO—), hydroxyl (—OH), and amine (—$NH_2$), with the proviso that $R_2$ and $R_4$ are not both hydrogen.

In some embodiments, a compound according to Formula VII has a structure selected from the group consisting of:

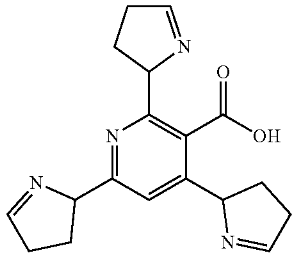
,

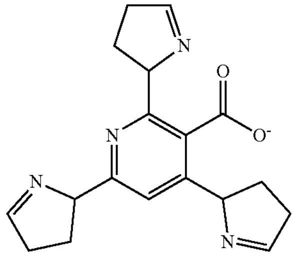

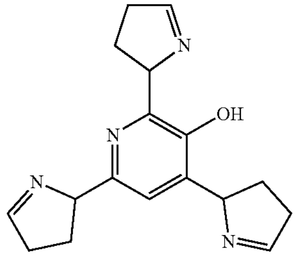
,

-continued

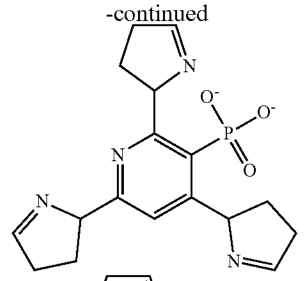

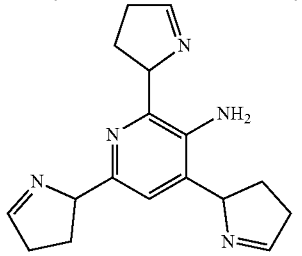

and

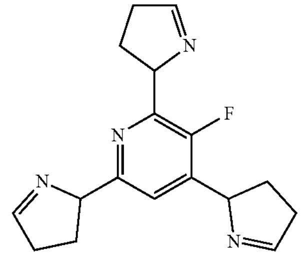

or a pharmaceutically acceptable salt, ester or solvate thereof.

In yet another aspect, a pharmaceutical composition comprises a therapeutically effective amount of at least one compound depicted above and a pharmaceutically acceptable vehicle therefor.

In still another aspect, a method of inhibiting formation of metal oxides comprising contacting a metal and at least one compound depicted above. In one example, the metal is present within a mammalian cell such as a human cell.

In another aspect, a method of treating hyperammonemia comprises administering to an individual in need thereof the aforesaid pharmaceutical composition.

In yet another aspect, a method of treating a disorder associated with chronic inflammation comprises administering to an individual in need thereof the aforesaid pharmaceutical composition. In another aspect, the present disclosure relates to a method of treating a disorder associated with chronic inflammation comprising administering to an individual in need thereof the pharmaceutical composition disclosed herein.

In another aspect, the present disclosure relates to a method of treating a subject suffering from vascular inflammation diseases or conditions, Th1 type vascular inflammation diseases or conditions, Th2 type vascular inflammation disease or conditions, Th1 type inflammation, monocyte activation responses, conditions or diseases related to T cell dependent B cell proliferation, activation, and class switching in the germinal centers of secondary lymphoid organs, Th2 type lung inflammation diseases or conditions, Th1 type lung inflammation diseases or conditions, multiple fibrosis diseases or conditions, or inflammation related responses in fibrotic tissue, diseases or conditions related to macrophage activation responses, wherein the method comprises administering the pharmaceutical composition disclosed herein to the subject.

In some embodiments, the subject suffers from chronic inflammatory diseases, vascular inflammation, restenosis, allergy, asthma, ulcerative colitis, atherosclerosis, rheumatoid arthritis, metabolic disease, organ transplantation related responses, psoriasis, Crohn's disease and inflammation caused hematological oncological diseases or conditions, pulmonary fibrosis, Chronic Obstructive Pulmonary Disease (COPD) exacerbations, sarcoidosis, pulmonary responses to respiratory infections, or Th1 type cutaneous inflammation responses to mechanical, chemical, or infectious agents.

In some embodiments, the Th1 type vascular inflammation diseases comprise chronic inflammatory diseases, vascular inflammation, or restenosis.

In some embodiments, wherein the Th2 type vascular inflammation diseases or conditions comprises allergy, asthma, or ulcerative colitis.

In some embodiments, Th1 type chronic inflammation and/or monocyte activation responses comprise atherosclerosis, restenosis, rheumatoid arthritis, or metabolic disease.

In some embodiments, the vascular inflammation diseases or conditions comprise organ transplantation related responses, rheumatoid arthritis, psoriasis, Crohn's disease and inflammation caused hematological oncological diseases or conditions.

In some embodiments, the conditions or diseases related to T cell dependent B cell proliferation, activation, and class switching in the germinal centers of secondary lymphoid organs comprises systemic lupus erythematosus (SLE), hematological oncology, autoimmune indications, asthma or allergy.

In some embodiments, the Th2 type lung inflammation diseases or conditions comprise asthma, pulmonary fibrosis, or Chronic Obstructive Pulmonary Disease (COPD) exacerbations.

In some embodiments, Th1 type lung inflammation diseases or conditions comprise sarcoidosis and pulmonary responses to respiratory infections.

In some embodiments, the Th1 type inflammation diseases or conditions comprise fibrosis, rheumatoid arthritis, dermatitis or psoriasis.

In some embodiments, the Th1 type inflammation diseases or conditions comprise Th1 type cutaneous inflammation responses to mechanical, chemical, or infectious agents.

In some embodiments, the diseases or conditions related to macrophage activation responses comprise atherosclerosis, restenosis, or rheumatoid arthritis.

In some embodiments, the present disclosure relates to a method of treating a cancer in a subject in need thereof, comprising administering a therapeutically effective amount of a compound disclosed herein or a pharmaceutical composition disclosed herein to the subject in need. In some embodiments, the cancer is selected from the group consisting of an adrenal gland tumor, an AIDS-associated cancer, an alveolar soft part sarcoma, an astrocytic tumor, bladder cancer, bone cancer, a brain and spinal cord cancer, a metastatic brain tumor, a breast cancer, a carotid body tumors, a cervical cancer, a chondrosarcoma, a chordoma, a chromophobe renal cell carcinoma, a clear cell carcinoma, a colon cancer, a colorectal cancer, a cutaneous benign fibrous histiocytoma, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder or bile duct cancer, gastric cancer, a gestational trophoblastic disease, a germ cell tumor, a head and neck cancer, hepatocellular carcinoma, an islet cell tumor, a Kaposi's Sarcoma, a kidney cancer, a leukemia, a lipoma/benign lipomatous tumor, a liposarcoma/malignant lipomatous tumor, a liver cancer, a lymphoma, a lung cancer, a medulloblastoma, a melanoma, a meningioma, a multiple endocrine neoplasia, a multiple myeloma, a myelodysplastic syndrome, a neuroblastoma, a neuroendocrine tumors, an ovarian cancer, a pancreatic cancer, a papillary thyroid carcinoma, a parathyroid tumor, a pediatric cancer, a peripheral nerve sheath tumor, a phaeochromocytoma, a pituitary tumor, a prostate cancer, a posterious uveal melanoma, a rare hematologic disorder, a renal metastatic cancer, a rhabdoid tumor, a rhabdomysarcoma, a sarcoma, a skin cancer, a soft-tissue sarcoma, a squamous cell cancer, a stomach cancer, a synovial sarcoma, a testicular cancer, a thymic carcinoma, a thymoma, a thyroid metastatic cancer, and a uterine cancer.

In some embodiments, the cancer is selected from the group consisting of colorectal cancer, hepatocellular carcinoma, glioma, kidney cancer, breast cancer, multiple myeloma, bladder cancer, neuroblastoma; sarcoma, non-Hodgkin's lymphoma, non-small cell lung cancer, ovarian cancer, pancreatic cancer, a rectal cancer, acute myeloid leukemia (AML), chronic myelogenous leukemia (CML), acute B lymphoblastic leukemia (B-ALL), chronic lymphocytic leukemia (CLL), hairy cell leukemia (HCL), blastic plasmacytoid dendritic cell neoplasm (BPDCN), non-Hodgkin's lymphomas (NHL), including mantel cell leukemia (MCL), and small lymphocytic lymphoma (SLL), Hodgkin's lymphoma, systemic mastocytosis, or Burkitt's lymphoma.

In another aspect, the present disclosure is related to a method of treating or preventing an iron overload condition or disease comprising administering to an individual in need thereof a pharmaceutical composition comprising a compound disclosed herein.

In some embodiments, the iron overload condition or disease comprises a hemochromatosis disease or condition.

In some embodiments, the iron overload conditions or diseases comprise a liver disease, inflammatory conditions, a chronic kidney disease, hyperthyroidism, anemia, a diabetes, a metabolic syndrome, Grave's disease, arrhythmias, and chronic hepatitis C infection, or a cancer.

In some embodiments, the inflammatory conditions comprise rheumatoid arthritis, autoimmune disease, acute infections, or atherosclerosis.

In another aspect, the present disclosure is related to a method of preventing or reversing telomere shortening, comprising administering to an individual in need thereof a pharmaceutical composition comprising a compound disclosed herein.

In another aspect, the present disclosure is related to a method of reversing or preventing a process, disease, or condition associated with aging, comprising administering to an individual in need thereof a pharmaceutical composition comprising a compound disclosed herein.

In some embodiments, the process associated with aging is hair loss, loss of vitality, or telomere shortening.

In some embodiments, administering of a pharmaceutical composition comprising a compound disclosed herein results in reduced VCAM-1 levels.

In one aspect, the present disclosure relates to a method of reducing VCAM-1 levels, wherein the method comprises administering to an individual in need thereof a pharmaceutical composition comprising a compound disclosed herein.

In one aspect, the present disclosure relates to a method of treating a gastrointestinal disease or disorder, wherein the method comprises administering to an individual in need thereof a pharmaceutical composition comprising a compound disclosed herein. In some embodiments, the gastrointestinal disease or disorder is selected from the group consisting of achalasia, Barrett's oesophagus, colorectal cancer, gastric cancer, oesophageal cancer, coeliac disease, colitis, Crohn's disease, diverticulosis, diverticulitis, gastritis, inflammatory bowel disease, ulcerative colitis, irritable bowel syndrome, microscopic colitis, collagenous colitis, lymphocytic colitis, pancreatitis, reflux oesophagitis, and ulcerative colitis.

In another aspect, the present disclosure relates to a method of treating an autoimmune disease, wherein the method comprises administering to an individual in need thereof a pharmaceutical composition comprising a compound disclosed herein. In some embodiments, the autoimmune disease is selected from the group consisting of lupus erythematosus; Wiskott-Aldrich syndrome; autoimmune lymphoproliferative syndrome; myasthenia gravis; rheumatoid arthritis (RA); lupus nephritis; multiple sclerosis; systemic lupus erythematosis, subacute cutaneous lupus erythematosus, cutaneous lupus erythematosus including chilblain lupus erythematosus, chronic arthritis, Sjogren's syndrome, autoimmune nephritis, autoimmune vasculitis, autoimmune hepatitis, autoimmune carditis, autoimmune encephalitis, autoimmune mediated hematological disease, inflammatory chronic rhinosinusitis, colitis, celiac disease, inflammatory bowel disease, Barrett's esophagus, and/or inflammatory gastritis.

In another aspect the present disclosure relates to a method of reducing or ameliorating reactivity, toxicity, or biodistribution of a metal in a subject in need thereof, wherein the method comprises administering to an individual in need thereof a compound or pharmaceutical composition disclosed herein. In some embodiments, the compound binds the metal.

In some embodiments, the compound binds the metal at two or more attachment sites.

In some embodiments, two or more compounds bind to the metal.

In some embodiments, the compound only binds the metal under a condition such as the presence of oxidative stress.

In some embodiments, the compound is activated by an enzyme to bind the metal.

In some embodiments, the compound is targeted to an organ or tissue.

In some embodiments, the compound alters the concentration or biodistribution of the metal in the subject.

In some embodiments, subject suffers from a metal overload disease or condition.

In some embodiments, the metal overload disease or condition comprises iron, copper, or zinc overload diseases or conditions.

In some embodiments, the metal is a transition metal.

In some embodiments, the transition metal comprises scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, and/or gold, preferably wherein the transition metal is iron, copper, and/or zinc.

In some embodiments, the metal is a trivalent metal ion, a bivalent metal ion, and/or a monovalent metal ion.

In some embodiments, the subject is a human.

In some embodiments, the subject is a mammal.

In some embodiments, the mammal comprises primates, dogs, horses, cats, cattle, or pigs.

In some embodiments, the subject comprises a non-human animal.

In some embodiments, the non-human animal is a bird or a reptile.

BRIEF DESCRIPTION OF FIGURES

FIG. 11 shows images of the resulting 2,4,6-Tri(3,4-dihydro-2H-pyrrol-2-yl)pyridine from both peaks of isolated compound 8.

DETAILED DESCRIPTION

Figure 1:
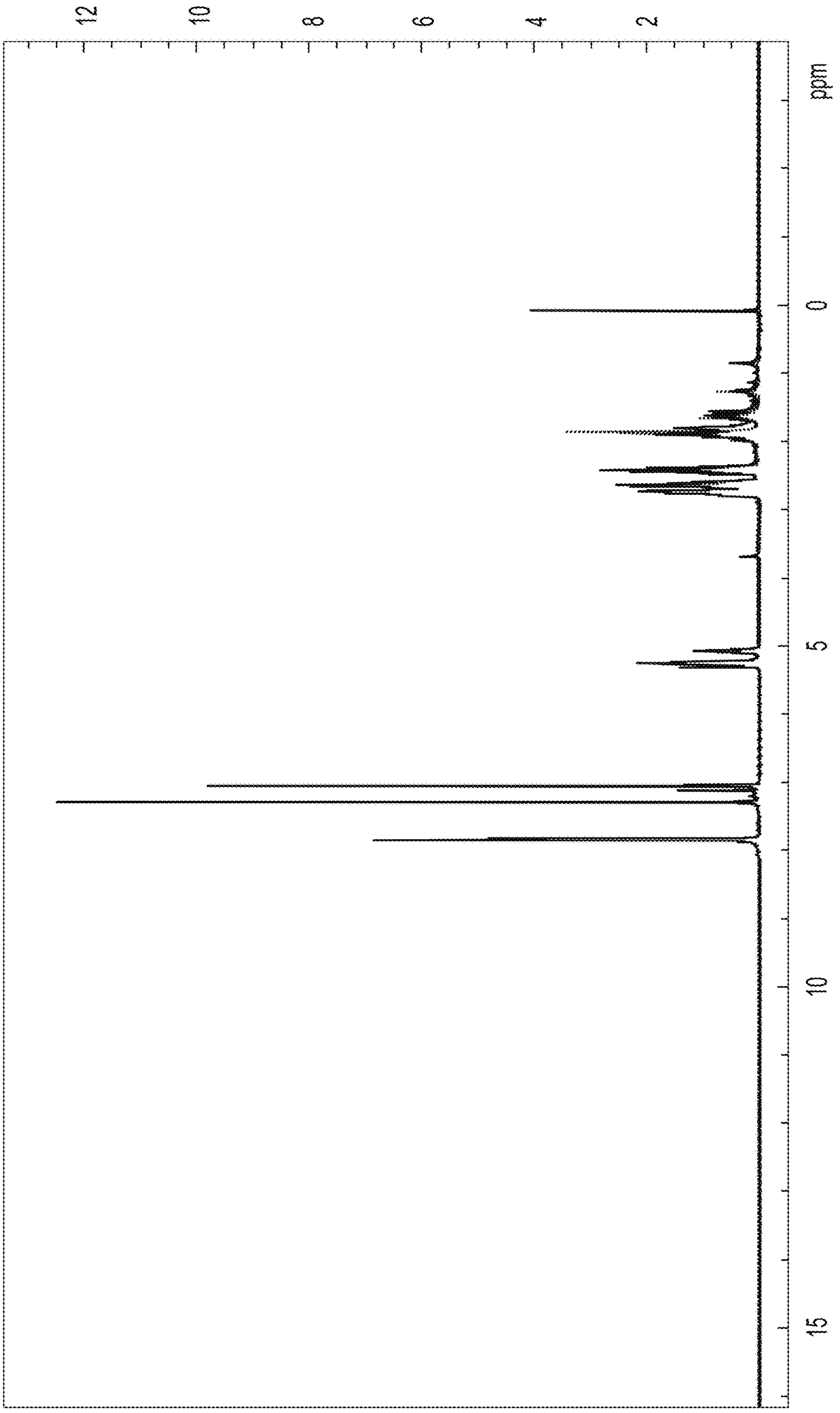
FIG. 1 shows $^1$H NMR (proton nuclear magnetic resonance) spectra for two different lots of 2,4,6-Tri(3,4-dihydro-2H-pyrrol-2-yl)pyridine synthesized according to protocol set forth in Example 5 herein. The $^1$H NMR spectra confirmed the identity and purity of the 2,4,6-Tri(3,4-dihydro-2H-pyrrol-2-yl)pyridine.
Figure 2:
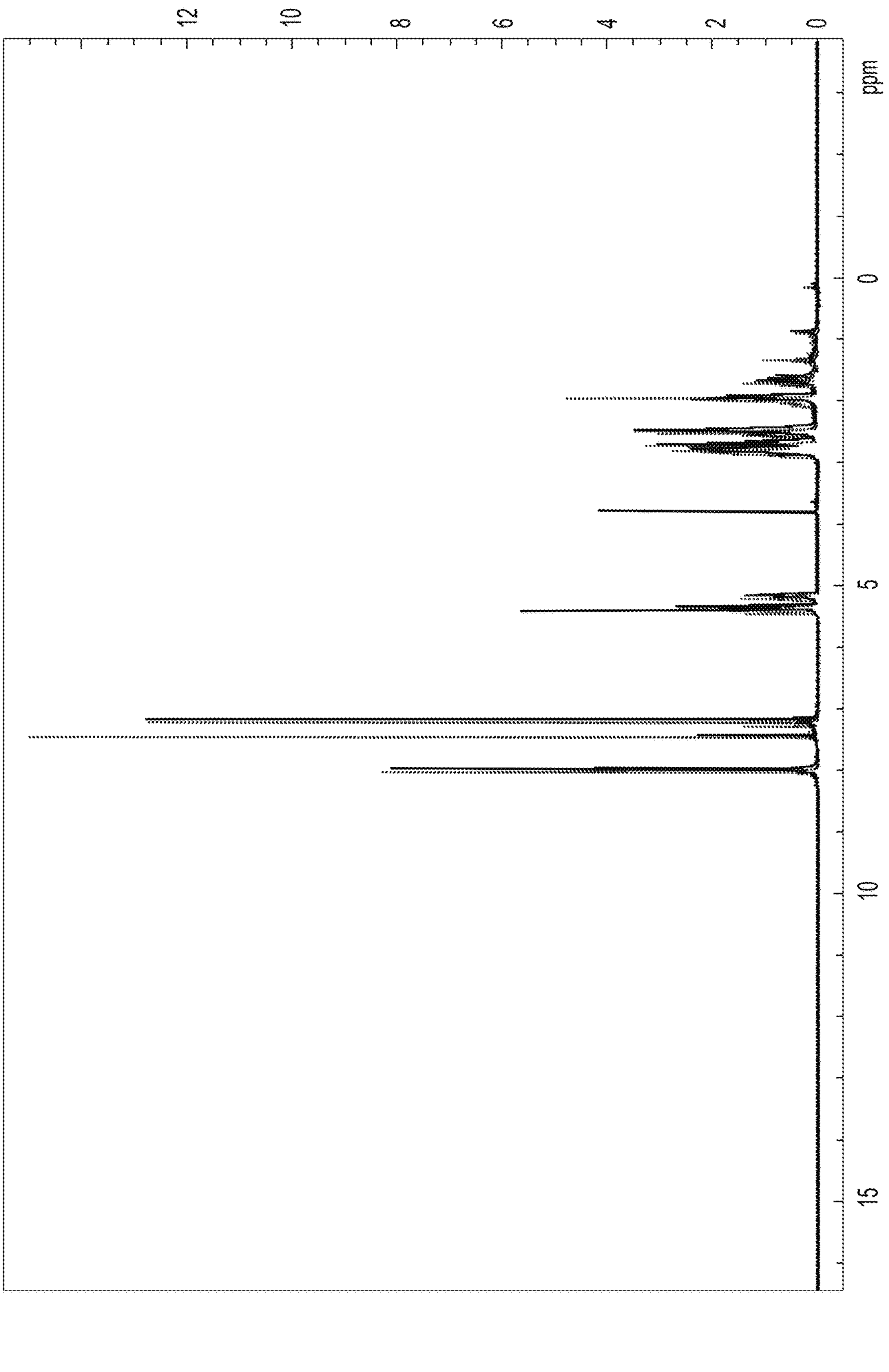
FIG. 2 shows $^1$H NMR spectra for two different lots of 2,4,6-Tri(3,4-dihydro-2H-pyrrol-2-yl)pyridine synthesized according to protocol set forth in Example 5 herein. The $^1$H NMR spectra confirmed the identity and purity of the 2,4,6-Tri(3,4-dihydro-2H-pyrrol-2-yl)pyridine.
Figure 3:
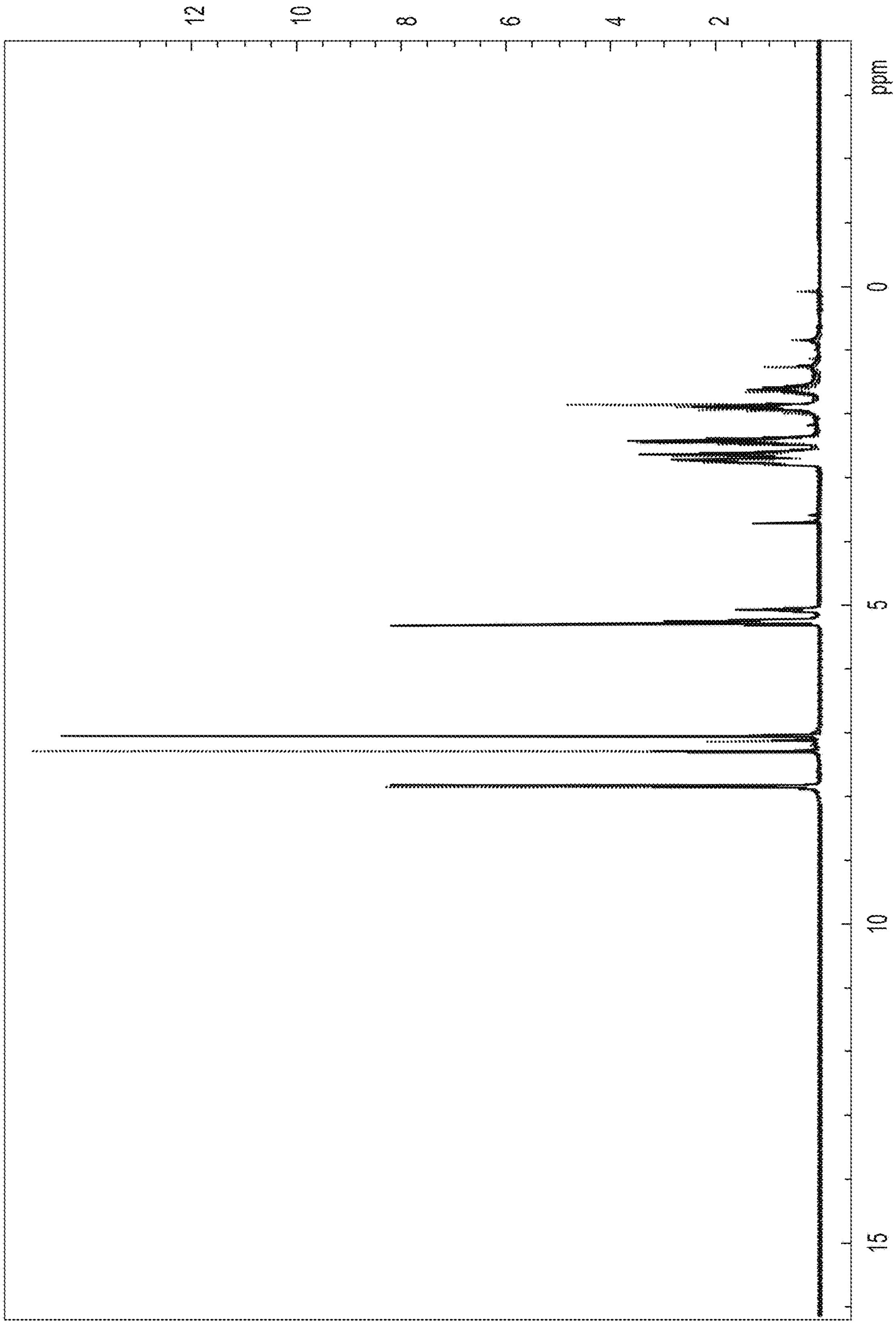
FIG. 3 shows $^1$H NMR spectra for two different lots of 2,4,6-Tri(3,4-dihydro-2H-pyrrol-2-yl)pyridine synthesized according to protocol set forth in Example 5 herein. The 1H NMR spectra confirmed the identity and purity of the 2,4,6-Tri(3,4-dihydro-2H-pyrrol-2-yl)pyridine.
Figure 4:
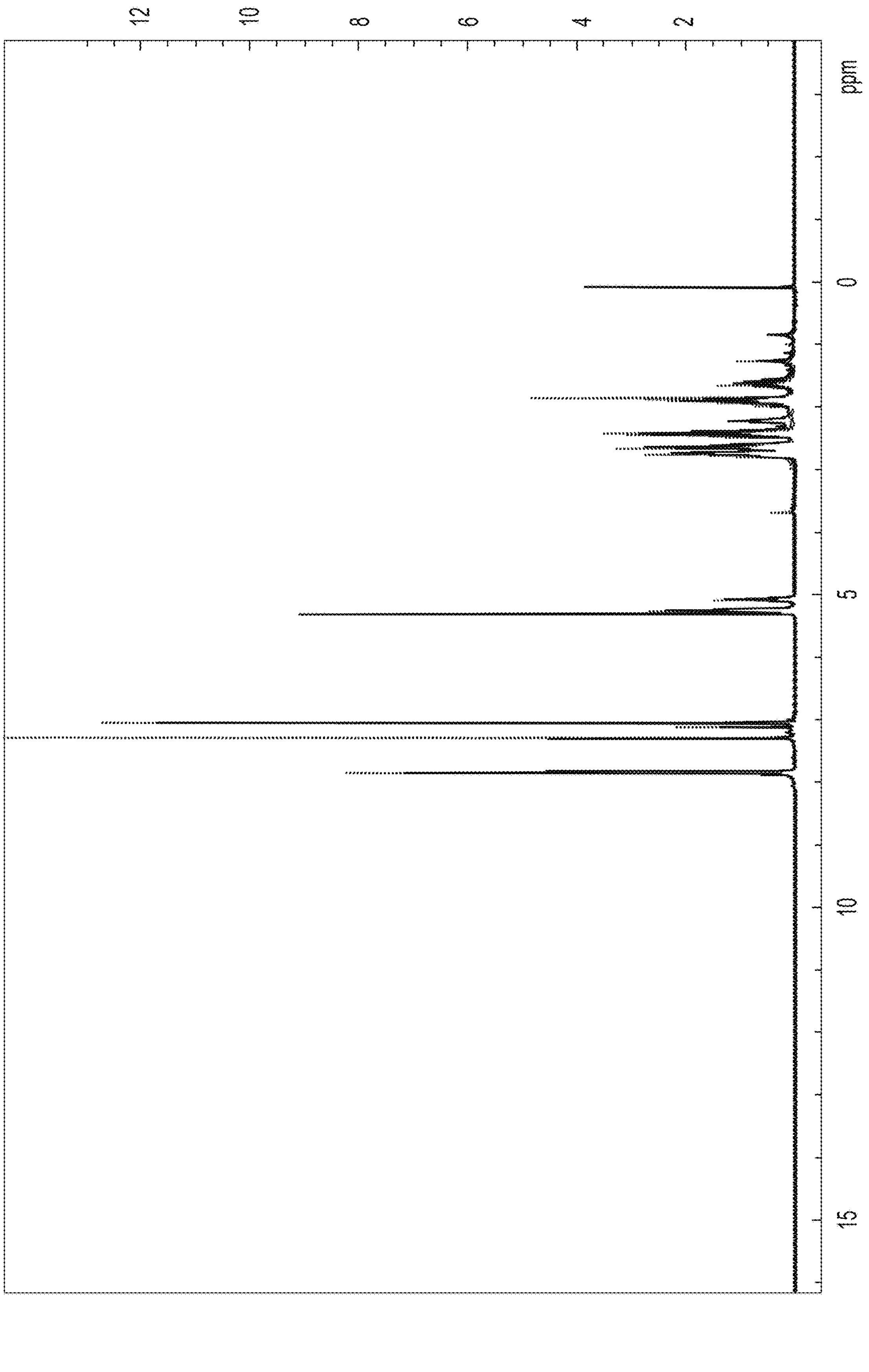
FIG. 4 shows $^1$H NMR spectra for two different lots of 2,4,6-Tri(3,4-dihydro-2H-pyrrol-2-yl)pyridine synthesized according to protocol set forth in Example 5 herein. The 1H NMR spectra confirmed the identity and purity of the 2,4,6-Tri(3,4-dihydro-2H-pyrrol-2-yl)pyridine.
Figure 5:
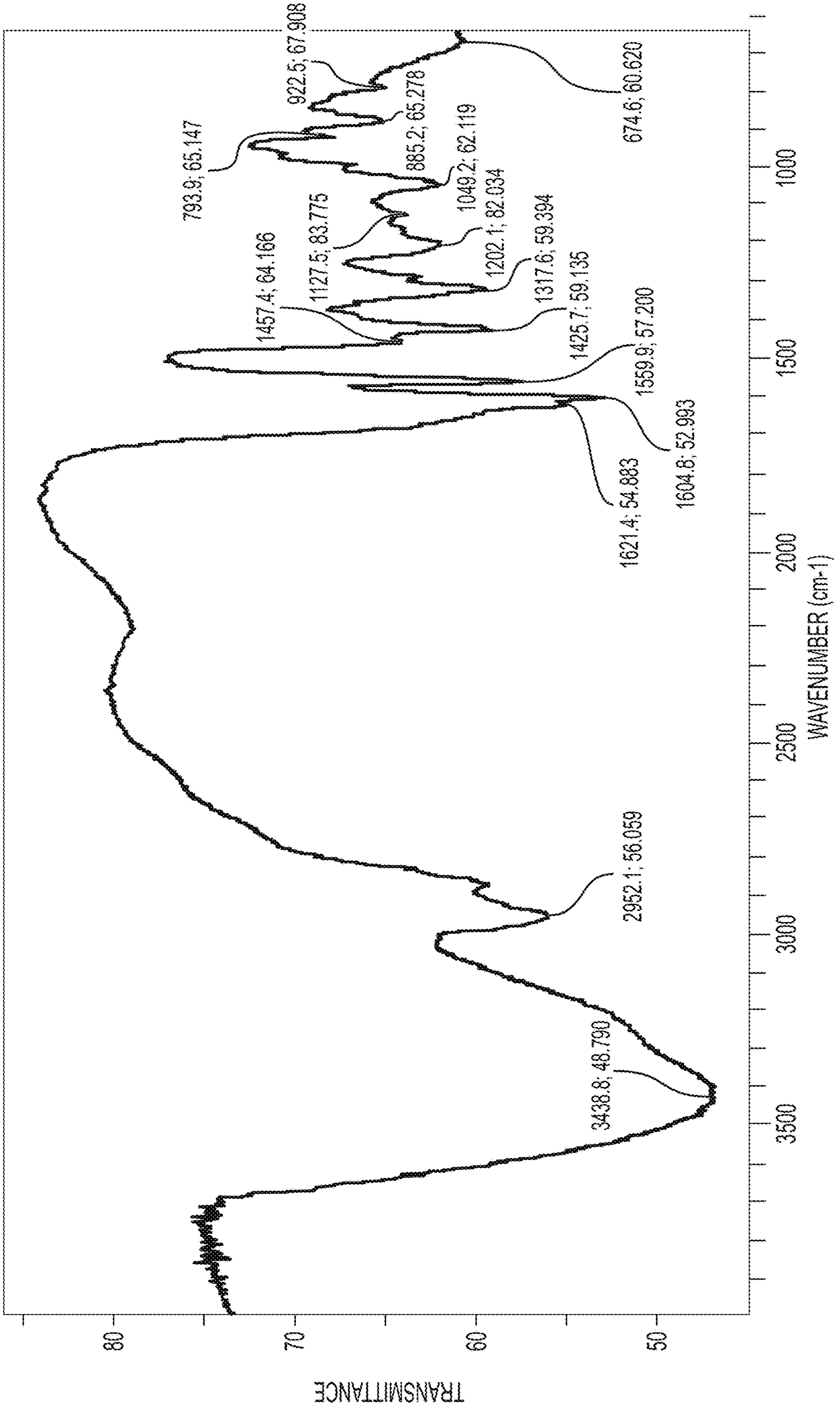
FIG. 5 shows IR (infrared) spectrum for an exemplary lot of 2,4,6-Tri(3,4-dihydro-2H-pyrrol-2-yl)pyridine synthesized according to protocol set forth in Example 5 herein. The IR spectra confirmed the identity and purity of the 2,4,6-Tri(3,4-dihydro-2H-pyrrol-2-yl)pyridine.
Figure 6:
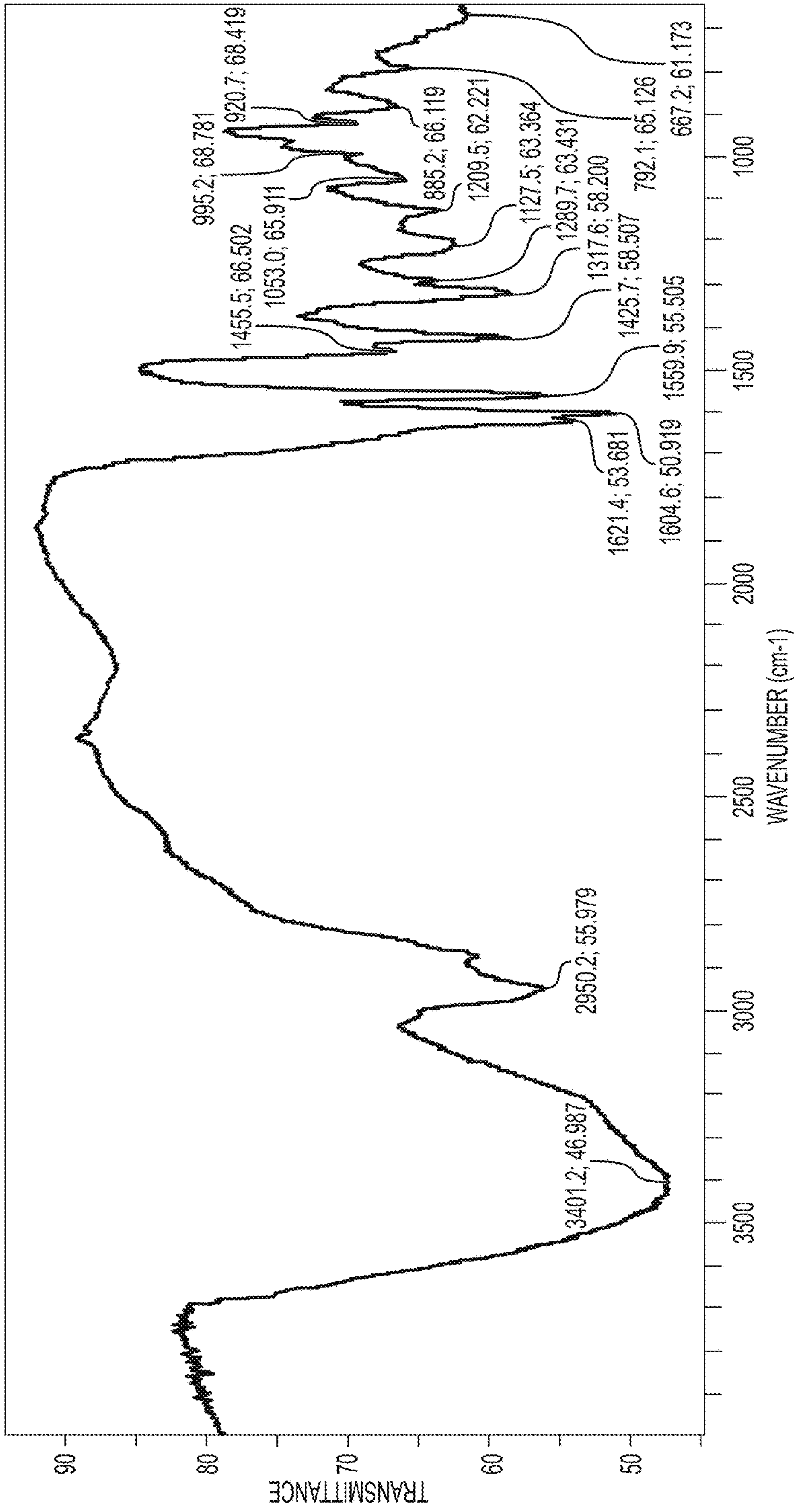
FIG. 6 shows IR spectrum for an exemplary lot of 2,4,6-Tri(3,4-dihydro-2H-pyrrol-2-yl)pyridine synthesized according to protocol set forth in Example 5 herein. The IR spectra confirmed the identity and purity of the 2,4,6-Tri(3,4-dihydro-2H-pyrrol-2-yl)pyridine.
Figure 7:
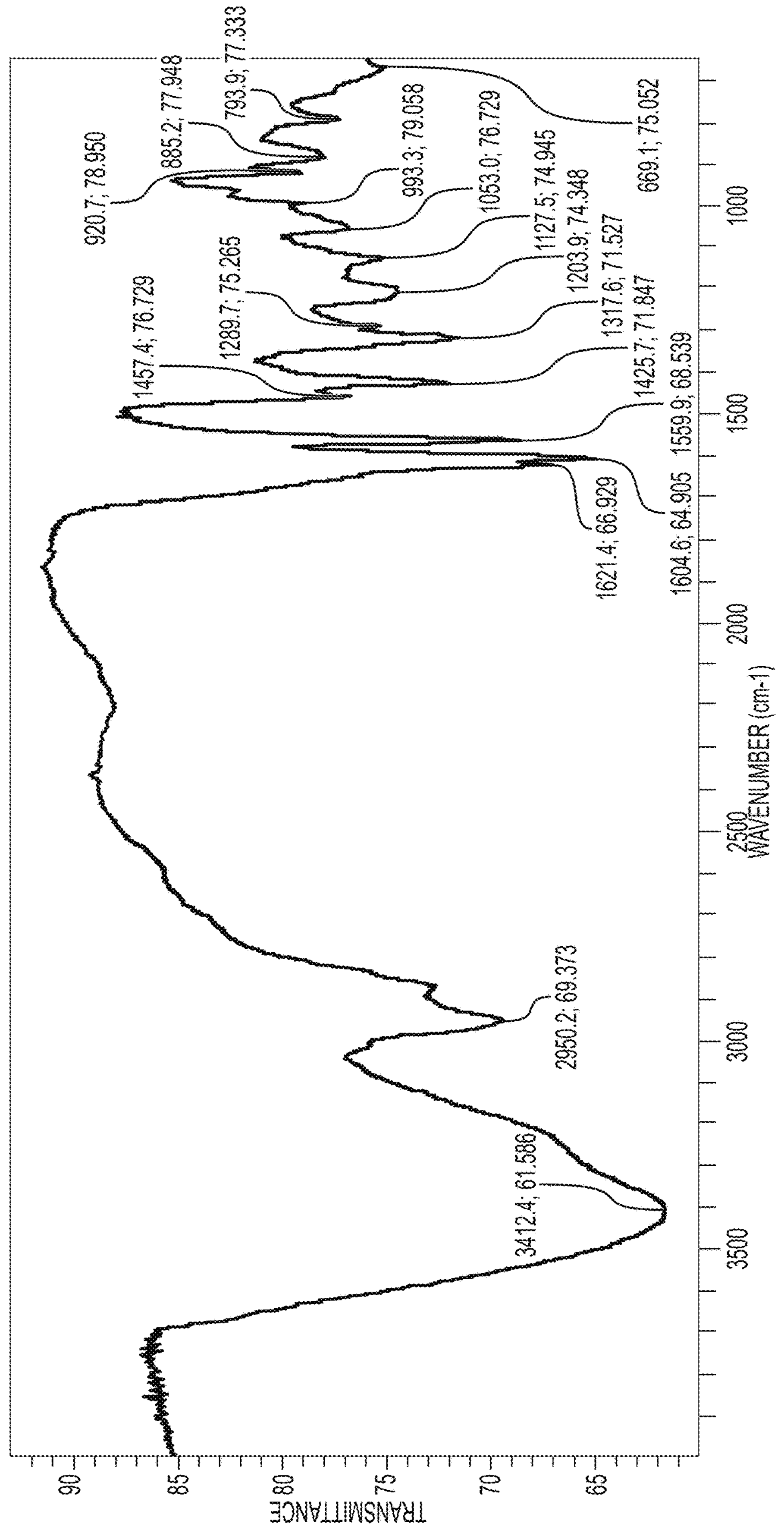
FIG. 7 shows IR spectrum for an exemplary lot of 2,4,6-Tri(3,4-dihydro-2H-pyrrol-2-yl)pyridine synthesized according to protocol set forth in Example 5 herein. The IR spectra confirmed the identity and purity of the 2,4,6-Tri(3,4-dihydro-2H-pyrrol-2-yl)pyridine.
Figure 8:
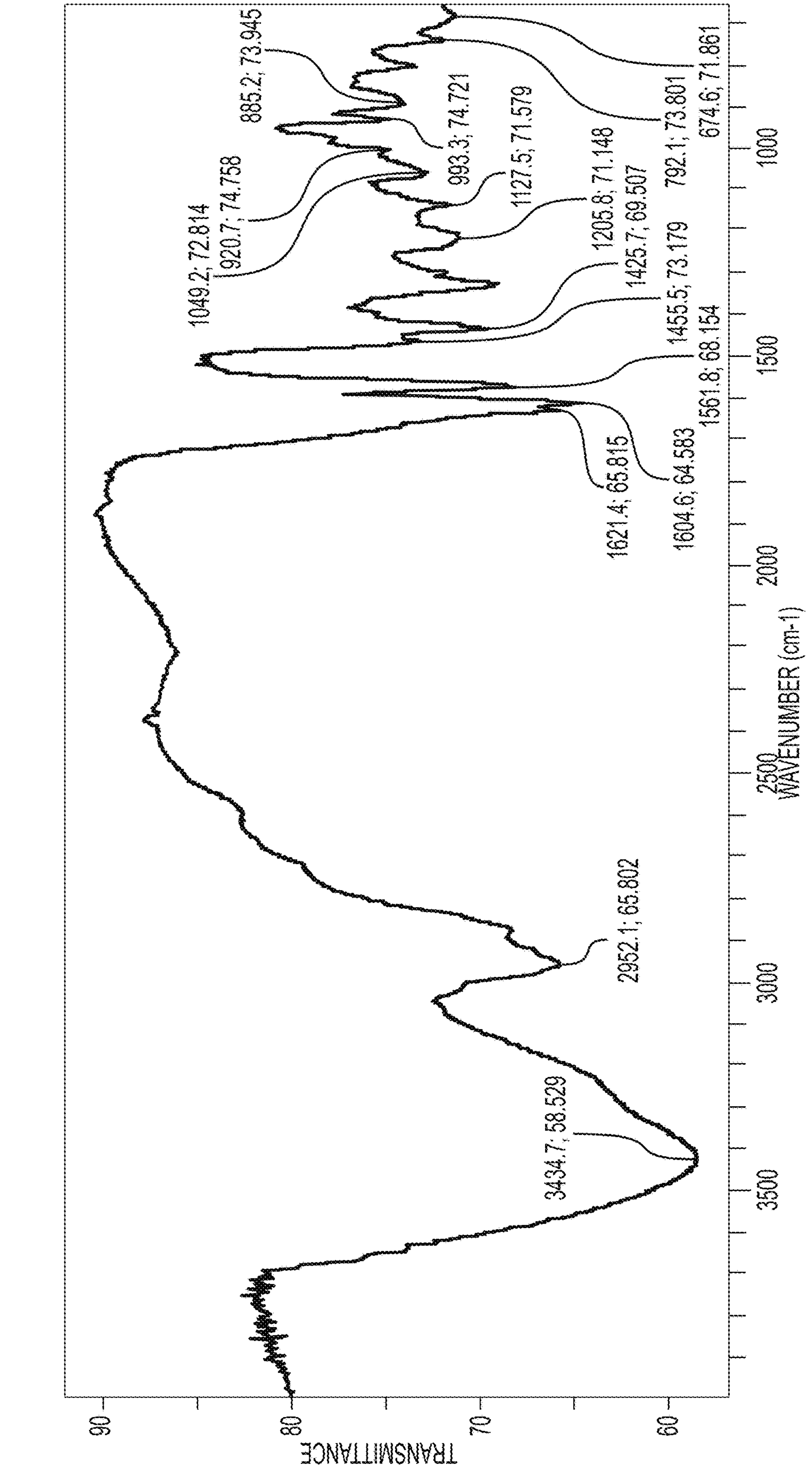
FIG. 8 shows IR spectrum for an exemplary lot of 2,4,6-Tri(3,4-dihydro-2H-pyrrol-2-yl)pyridine synthesized according to protocol set forth in Example 5 herein. The IR spectra confirmed the identity and purity of the 2,4,6-Tri(3,4-dihydro-2H-pyrrol-2-yl)pyridine.

The pharmaceutical compounds disclosed herein have anti-inflammatory activity, anti-cancer activity, and are useful for treating hemochromatosis. The compounds disclosed herein may also function as metal enzyme inhibitor, and may prevent enzymatic actions that create imbalances of cellular metals and telomere shortening. Furthermore, the compounds disclosed herein may prevent, reverse, or slow down processes associated with aging as shown in Examples 6 and 7 herein.

Hence, in some aspects, the present disclosure relates to a method of reducing or ameliorating reactivity, toxicity, or biodistribution of a metal in a subject in need thereof, wherein the method comprises administering to an individual in need thereof a compound or pharmaceutical composition disclosed herein. In some embodiments, the compound binds the metal. In some embodiments, the compound binds the metal at two or more attachment sites. In some embodiments, two or more compounds bind to the metal.

In some embodiments, a therapeutically effective amount of a compound herein is administered to the individual in need therefore, wherein the therapeutically effective amount reduces metal reactivity, toxicity, or ameliorates the biodistribution of the metal. In some embodiments, the therapeutically effective amount of a compound does not disturb normal and healthy metal status in the individual. In some embodiments, the compound is not cytotoxic to normal and healthy cells, tissues, or organs. Exemplary therapeutically effective amounts are disclosed elsewhere herein.

In some embodiments, a compound disclosed herein reduces the level of metal reactivity by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

In some embodiments, a compound disclosed herein reduces the cytotoxicity of a metal by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

In some embodiments, a compound disclosed herein ameliorates metal reactivity by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

In some embodiments, a compound disclosed herein ameliorates metal biodistribution by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

In some embodiments, a compound disclosed herein ameliorates or reduces metalloenzyme activity by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

The compounds disclosed herein may be designed to preferentially bind metals under certain cellular conditions or upon enzymatic activation. For example, the compounds may be modified to only bind metal under oxidative stress such as in the presence of hydrogen peroxide. Modified compounds activated by oxidative stress may be boronate based. Oxidative stress is associated with many disease such as the inflammatory, gastrointestinal, autoimmune or cancer diseases disclosed herein.

In some embodiments, the compound is targeted to an organ or tissue by modification of the compound. For example, incorporation of N-acetyl-galactosamine helps targeting hepatocytes.

In some embodiments, the compound alters the concentration or biodistribution of the metal in the subject.

In some embodiments, the metal is a transition metal.

In some embodiments, the transition metal comprises scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, and/or gold, preferably wherein the transition metal is iron, copper, and/or zinc.

In some embodiments, the metal is a trivalent metal ion, a bivalent metal ion, and/or a monovalent metal ion.

In some embodiments, subject suffers from a metal overload disease or condition.

In some embodiments, the metal overload disease or condition comprises iron, copper, or zinc overload diseases or conditions.

For example, a compound disclosed herein such as 2,4,6-Tri(3,4-dihydro-2H-pyrrol-2-yl)pyridine may help balance the levels of intracellular iron as well as iron in circulation in iron overload (IO) conditions. One IO condition is Hereditary Hemochromatosis (HH) caused by mutations in the iron storage protein Ferritin. Iron overload conditions also include secondary hemochromatosis which can occur in patients who have hemoglobinopathies (e.g., sickle cell disease, thalassemia, and sideroblastic anemias), congenital hemolytic anemias, and myelodysplasia.

Iron overload associated conditions can also include liver disease, rheumatoid arthritis or other inflammatory conditions, hyperthyroidism, or cancer such as Pancreatic cancer, colorectal cancer, lung cancer, T-cell lymphoma, and hepatocellular carcinoma. Excess iron deposition is also associated with inflammatory conditions, chronic kidney disease, rheumatoid arthritis, autoimmune disease, acute infections, cancer, anemia of chronic disease, type 2 diabetes, metabolic syndromes, atherosclerosis, fatty liver disease, anorexia, Grave's disease, arrhythmias, and chronic hepatitis C infection. In some embodiments, the iron overload condition or disease comprises a hemochromatosis disease or condition. In some embodiments, the iron overload condition or disease comprises a liver disease, inflammatory conditions, a chronic kidney disease, hyperthyroidism, anemia, a diabetes, a metabolic syndrome, Grave's disease, arrhythmias, and chronic hepatitis C infection, or a cancer.

In some embodiments, the inflammatory conditions comprise rheumatoid arthritis, autoimmune disease, acute infections, or atherosclerosis.

The compounds disclosed herein may also prevent or reverse absolute telomere length (ATL) shortening, which is a key molecular feature of cellular aging and DNA damage associated with chronic diseases and mortality. Indeed, telomere shortening has been discovered to be the primary cause of human aging. In particular, reduced ATL has been associated with almost all chronic diseases related to aging such as cancer, heart disease, diabetes, and autoimmune diseases.

Telomeres are the end part of the chromosomes, and serve to protect the DNA just like shoelace tips preserve a shoelace from unraveling. When the telomeres shorten to critical lengths, the DNA is no longer protected during replication, resulting DNA damage and chromosomal rearrangements, which in turn lead to senescence, apoptosis, or oncogenic transformation of somatic cells.

In another aspect, the present disclosure is related to a method of treating or preventing an iron overload conditions or diseases comprising administering to an individual in need thereof a pharmaceutical composition comprising a compound disclosed herein.

In another aspect, the present disclosure is related to a method of preventing or reversing telomere shortening, comprising administering to an individual in need thereof a pharmaceutical composition comprising a compound disclosed herein.

In another aspect, the present disclosure is related to a method of reversing or preventing a process, disease, or condition associated with aging, comprising administering to an individual in need thereof a pharmaceutical composition comprising a compound disclosed herein.

In some embodiments, administering of a pharmaceutical composition comprising a compound disclosed herein results in reduced VCAM-1 levels.

In one aspect, the present disclosure relates to a method of reducing VCAM-1 levels, wherein the method comprises administering to an individual in need thereof a pharmaceutical composition comprising a compound disclosed herein.

In some embodiments, the process associated with aging is hair loss, loss of vitality, or telomere shortening. As used herein the term "vitality" refers to vitality as defined by the World Health Organization (WHO): "the composite of all the physical and mental capacities that an individual can draw on at any point in time." Hence vitality comprises mental vitality, physical vitality, and/or a combination of both mental and physical vitality. Many measurements for mental vitality are known in the art including the 10-item Geriatric Depression Scale (GDS). Physical vitality can be measured by a number of different physical exercises such as hand grip strength (HGS), gait speed, knee-extensor strength, or sit-to-stand tests. In some embodiments, vitality comprises the biophysiological status of an individual and the capacity for maintaining homoeostasis in the face of usual daily exposures and of more extreme and unusual or unexpected challenges, such as injury or infection. In some embodiments, vitality is the amount of intrinsic capacity that can be retained, and could be seen as underlying an individual's vigor, stamina, and resilience to challenges. The main characteristics of vitality are hormonal function, energy metabolism, and cardiovascular function. Other characteristics of vitality are nutrition, body composition, depression status, fatigue, metabolism, immune system response, respiratory function, or muscle endurance.

Fatigue can include measurements of muscle endurance, assessment of self-perceived fatigue, daytime fatigue, etc. Metabolic fatigue can be measured by insulin sensitivity, glycosylated hemoglobin, serum albumin, fasting blood glucose, or the hormonal status of the hypothalamic-pituitary-adrenal axis. Body composition can be measured by anthropomethry, bodyweight, BMI, waist circumference, and muscle mass. Cardiovascular function can be measured by heart rate during physical activity, heart rate variability, oxygen saturation, orthostatic hypotension or response after recumbency, blood pressure, cardiovascular system health, or maximum oxygen consumption. Nutrition can be assess by measuring or evaluating appetite, weight loss, malnutrition, undernutrition, or the Mini Nutritional Assessment. Immune or stress response can be assessed by circulating biomarkers of inflammation, perceived immune status, oxygen saturation, or autonomic function. Other measurable characteristics of vitality are self-esteem assessment, mitochondrial function, sedentary behavior, sleep amount and quality, methylation clock, or electrolyte balance.

For example, a compound may have an anti-inflammatory activity capable of reducing the levels of an inflammation-inducing molecule. While not wanting to be bound by theory, it is believed that the disclosed compounds may have an anti-inflammatory activity capable of reducing the levels of substance P(SP), calcitonin gene-related peptide (CGRP), glutamate, or a combination thereof. A compound may have an anti-inflammatory activity capable of reducing the levels of SP, CGRP, glutamate, or a combination thereof released from a sensory neuron by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

Prostaglandins mediate a local inflammatory response and are involved in all inflammatory functions through action on prostaglandin receptors and mediate inflammatory signaling including chemotaxis (macrophages, neutrophils and eosinophils), vasodilation and algesia. However, the PG-mediated inflammatory response is self-limiting (resolving). The principle resolution factor is a prostaglandin called 15dPGJ2, which is an endogenous agonist of peroxisome proliferator-activator receptor-γ (PPAR-γ) signaling. PPAR-7 signaling pathway 1) induces apoptosis of macrophage M1 cells, thereby reducing the levels of Th1 pro-inflammatory cytokines and 2) promotes differentiation of monocytes into macrophage M2 cells. Macrophage M2 cells produce and release Th2 anti-inflammatory cytokines.

Compounds disclosed herein may have an anti-inflammatory activity capable of reducing the levels of an inflammation inducing prostaglandin. A compound may have an anti-inflammatory activity capable of reducing the levels of an inflammation inducing prostaglandin released from a sensory neuron by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. A compound may have an anti-inflammatory activity capable of reducing the levels of an inflammation inducing prostaglandin released from a sensory neuron in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

The peroxisome proliferator-activated receptors (PPARs) are a group of nuclear receptor proteins that function as transcription factors regulating the expression of genes. All PPARs are known to heterodimerize with the retinoid X receptor (RXR) and bind to specific regions on the DNA of target genes called peroxisome proliferator hormone response elements (PPREs). PPARs play essential roles in the regulation of cellular differentiation, development, and metabolism (carbohydrate, lipid, protein), and tumorigenesis of higher organisms. The family comprises three members, PPAR-α, PPAR-γ, and PPAR-δ (also known as PPAR-β). PPAR-α is expressed in liver, kidney, heart, muscle, adipose tissue, as well as other tissues. PPAR-δ is expressed in many tissues but markedly in brain, adipose tissue, and skin. PPAR-γ comprises three alternatively-spliced forms, each with a different expression pattern. PPAR-γ1 is expressed in virtually all tissues, including heart, muscle, colon, kidney, pancreas, and spleen. PPAR-γ2 is expressed mainly in adipose tissue. PPAR-γ3 is expressed in macrophages, large intestine, and white adipose tissue. Endogenous ligands for the PPARs include free fatty acids and eicosanoids. PPAR-γ is activated by PGD2 (a prostaglandin), whereas PPAR-α is activated by leukotriene B4.

A compound may have an anti-inflammatory activity capable of reducing the levels of IFN-γ, TNF-α, IL-12, or a combination thereof released from a Th1 cell and increasing the levels of IL-10 released from a Th2 cell. A compound may have an anti-inflammatory activity capable of reducing the levels of IFN-γ, TNF-α, IL-12, or a combination thereof released from a Th1 cell by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%, and capable of increasing the levels of IL-10 released from a Th2 cell by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

A compound may have an anti-inflammatory activity capable of stimulating some or all PPAR signaling pathways. It is contemplated that such a compound therefore may act as a PPAR pan-agonist or possibly as a selective PPAR agonist.

A compound may have an anti-inflammatory activity capable of modulating Th1 and Th2 cytokines. A compound may have an anti-inflammatory activity capable of reducing the levels of Interferon-γ (IFN-γ), tumor necrosis factor-α (TNF-α), interleukin-12 (IL-12), or a combination thereof released from a Th1 cell. A compound may have an anti-inflammatory activity capable of reducing the levels of inflammatory molecules released from a Th1 or Th2 cell by, e.g., at least 10%, at least 20%, at least 30%, at least 40%, at least 50%, at least 60%, at least 70%, at least 80%, or at least 90%. A compound may have an anti-inflammatory activity capable of reducing the levels of inflammatory molecules released from a Th1 or Th2 cell in a range from, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, or about 10% to about 90%.

For example, a compound may have an anti-inflammatory activity capable of reducing the levels of IFN-γ, TNF-α, IL-12, or a combination thereof released from a Th1 cell by, e.g., at least 10%, at least 20%, at least 30%, at least 40%, at least 50%, at least 60%, at least 70%, at least 80%, or at least 90%. A compound may have an anti-inflammatory activity capable of reducing the levels of IFN-γ, TNF-α, IL-12, or a combination thereof released from a Th1 cell in a range from, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, or about 10% to about 90%.

A compound such as 2,4,6-tris(3,4-dihydro-2H-pyrrol-2-yl)pyridine, and 2,4,6-tris(3,4-dihydro-2H-pyrrol-2-yl)pyridine with ethanol as carrier may have an anti-inflammatory activity capable of modulating inflammatory molecules. A compound may have an anti-inflammatory activity capable of reducing the levels of CD40, sIgG, sIL-10, HLA-DR, sIL-17A, CD38, sIL-6, sIL-17F, sIL-2. A compound may have an anti-inflammatory activity capable of reducing the levels of CD40, sIgG, sIL-10, HLA-DR, sIL-17A, CD38, sIL-6, sIL-17F, sIL-2 or a combination thereof at least 10%, at least 20%, at least 30%, at least 40%, at least 50%, at least 60%, at least 70%, at least 80%, or at least 90%. A compound may have an anti-inflammatory activity capable of reducing the levels of CD40, sIgG, sIL-10, HLA-DR, sIL-17A, CD38, sIL-6, sIL-17F, sIL-2 from about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, or about 10% to about 90%.

A compound may have an anti-inflammatory activity capable of reducing the levels of Eotaxin 3, MCP-1, VCAM-1, MIG, IL-6, and/or P-selectin. A compound may have an anti-inflammatory activity capable of reducing the levels of Eotaxin 3, MCP-1, VCAM-1, MIG, IL-6, P-selectin or a combination thereof at least 10%, at least 20%, at least 30%, at least 40%, at least 50%, at least 60%, at least 70%, at least 80%, or at least 90%. A compound may have an anti-inflammatory activity capable of reducing the levels of Eotaxin 3, MCP-1, VCAM-1, MIG, IL-6, and/or P-selectin from about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, or about 10% to about 90%.

A compound may have an anti-inflammatory activity capable of reducing the levels of Eotaxin 3, MCP-1, MIP-1α, I-TAC, MIG, IP-10, IL-6, VCAM-1, SAA, IL-1α, and P-selectin. A compound may have an anti-inflammatory activity capable of reducing the levels of Eotaxin 3, MCP-1, MIP-1α, I-TAC, MIG, IP-10, IL-6, VCAM-1, SAA, IL-1α, P-selectin or a combination thereof at least 10%, at least 20%, at least 30%, at least 40%, at least 50%, at least 60%, at least 70%, at least 80%, or at least 90%. A compound may have an anti-inflammatory activity capable of reducing the levels of Eotaxin 3, MCP-1, MIP-1α, I-TAC, MIG, IP-10, IL-6, VCAM-1, SAA, IL-1α, and/or P-selectin from about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, or about 10% to about 90%.

A compound may have an anti-inflammatory activity capable of increasing the levels of IL-10 released from a Th2 cell. A compound may have an anti-inflammatory activity capable of increasing the levels of IL-10 released from a Th2 cell by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

The compounds disclosed herein may also impact tissue remodeling activities by decreasing TIMP-1, Collagen IV, PAI-1, and/or Collagen III. A compound may have tissue remodeling activity capable of reducing the levels of TIMP-1, Collagen IV, PAI-1, and/or Collagen III or a combination thereof at least 10%, at least 20%, at least 30%, at least 40%, at least 50%, at least 60%, at least 70%, at least 80%, or at least 90%. A compound may have an tissue remodeling activity capable of reducing the levels of TIMP-1, Collagen IV, PAI-1, and/or Collagen III from about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, or about 10% to about 90%.

The compounds disclosed herein may also impact tissue remodeling activities by decreasing TIMP-1, Collagen IV, MMP-1, PAI-1, uPAR, αSMA, and/or MMP-9. A compound may have tissue remodeling activity capable of reducing the levels of TIMP-1, Collagen IV, MMP-1, PAI-1, uPAR, αSMA, and/or MMP-9 or a combination thereof at least 10%, at least 20%, at least 30%, at least 40%, at least 50%, at least 60%, at least 70%, at least 80%, or at least 90%. A compound may have an tissue remodeling activity capable of reducing the levels of TIMP-1, Collagen IV, MMP-1, PAI-1, uPAR, αSMA, and/or MMP-9 from about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, or about 10% to about 90%.

The compounds disclosed herein may also impact tissue remodeling activities by decreasing Collagen I, TIMP-2, TIMP-1, Collagen IV, tPA, Collagen III, αSMA, bFGF, MMP-1, PAI-1, Ker8/18, and/or MMP-9. A compound may have tissue remodeling activity capable of reducing the levels of Collagen I, TIMP-2, TIMP-1, Collagen IV, tPA, Collagen III, αSMA, bFGF, MMP-1, PAI-1, Ker8/18, and/or MMP-9 or a combination thereof at least 10%, at least 20%, at least 30%, at least 40%, at least 50%, at least 60%, at least 70%, at least 80%, or at least 90%. A compound may have an tissue remodeling activity capable of reducing the levels of Collagen I, TIMP-2, TIMP-1, Collagen IV, tPA, Collagen III, αSMA, bFGF, MMP-1, PAI-1, Ker8/18, and/or MMP-9 from about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, or about 10% to about 90%.

The compounds disclosed herein may impact hemostasis-related activities as demonstrated by decreased TM (thrombomodulin) and increased TF (Tissue Factor). The compounds disclosed herein may decrease TM by at least 10%, at least 20%, at least 30%, at least 40%, at least 50%, at least 60%, at least 70%, at least 80%, or at least 90%. The compounds disclosed herein may increase TF by at least 10%, at least 20%, at least 30%, at least 40%, at least 50%, at least 60%, at least 70%, at least 80%, or at least 90%. The compounds disclosed herein may have an hemostasis related activity capable of reducing the levels of TM by from about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, or about 10% to about 90%. The compounds disclosed herein may have an hemostasis related activity capable of increasing the levels of TF by from about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, or about 10% to about 90%.

Accordingly, 2,4,6-tris(3,4-dihydro-2H-pyrrol-2-yl)pyridine, and 2,4,6-tris(3,4-dihydro-2H-pyrrol-2-yl)pyridine with ethanol as carrier may be used in a method of treating a subject suffering from vascular inflammation diseases or conditions, Th1 type vascular inflammation diseases or conditions, Th2 type vascular inflammation disease or conditions, Th1 type inflammation, monocyte activation responses, conditions or diseases related to T cell dependent B cell proliferation, activation, and class switching in the germinal centers of secondary lymphoid organs, Th2 type lung inflammation diseases or conditions, Th1 type lung inflammation diseases or conditions, multiple fibrosis diseases or conditions, or inflammation related responses in fibrotic tissue, diseases or conditions related to macrophage activation responses.

In some embodiments, the subject suffers from chronic inflammatory diseases, vascular inflammation, restenosis, allergy, asthma, ulcerative colitis, atherosclerosis, rheumatoid arthritis, metabolic disease, organ transplantation related responses, psoriasis, Crohn's disease and inflammation caused hematological oncological diseases or conditions, pulmonary fibrosis, Chronic Obstructive Pulmonary Disease (COPD) exacerbations, sarcoidosis, pulmonary responses to respiratory infections, or Th1 type cutaneous inflammation responses to mechanical, chemical, or infectious agents.

In some embodiments, the Th1 type vascular inflammation diseases comprise chronic inflammatory diseases, vascular inflammation, or restenosis.

In some embodiments, wherein the Th2 type vascular inflammation diseases or conditions comprises allergy, asthma, or ulcerative colitis.

In some embodiments, Th1 type chronic inflammation and/or monocyte activation responses comprise atherosclerosis, restenosis, rheumatoid arthritis, or metabolic disease.

In some embodiments, the vascular inflammation diseases or conditions comprise organ transplantation related responses, rheumatoid arthritis, psoriasis, Crohn's disease and inflammation caused hematological oncological diseases or conditions.

In some embodiments, the conditions or diseases related to T cell dependent B cell proliferation, activation, and class switching in the germinal centers of secondary lymphoid organs comprises systemic lupus erythematosus (SLE), hematological oncology, autoimmune indications, asthma or allergy.

In some embodiments, the Th2 type lung inflammation diseases or conditions comprise asthma, pulmonary fibrosis, or Chronic Obstructive Pulmonary Disease (COPD) exacerbations.

In some embodiments, Th1 type lung inflammation diseases or conditions comprise sarcoidosis and pulmonary responses to respiratory infections.

In some embodiments, the Th1 type inflammation diseases or conditions comprise fibrosis, rheumatoid arthritis, dermatitis or psoriasis.

In some embodiments, the Th1 type inflammation diseases or conditions comprise Th1 type cutaneous inflammation responses to mechanical, chemical, or infectious agents.

In some embodiments, the diseases or conditions related to macrophage activation responses comprise atherosclerosis, restenosis, or rheumatoid arthritis.

A chronic inflammation symptom can be associated with a large, otherwise unrelated group of disorders which underlay a variety of diseases and disorders. The immune system is often involved with chronic inflammatory disorders, demonstrated in both allergic reactions and some myopathies, with many immune system disorders resulting in abnormal inflammation. Non-immune diseases with etiological origins in chronic inflammatory processes include cancer, atherosclerosis, and ischaemic heart disease. Non-limiting examples of disorders exhibiting chronic inflammation as a symptom include, without limitation, acne, acid reflux/heartburn, age related macular degeneration (AMD), allergy, allergic rhinitis, Alzheimer's disease, amyotrophic lateral sclerosis, anemia, appendicitis, arteritis, arthritis, asthma, atherosclerosis, autoimmune disorders, balanitis, blepharitis, bronchiolitis, bronchitis, a bullous pemphigoid, burn, bursitis, cancer, cardiac arrest, carditis, celiac disease, cellulitis, cervicitis, cholangitis, cholecystitis, chorioamnionitis, chronic obstructive pulmonary disease (COPD), cirrhosis, colitis, congestive heart failure, conjunctivitis, Crohn's disease, cyclophosphamide-induced cystitis, cystic fibrosis, cystitis, common cold, dacryoadenitis, dementia, dermatitis, dermatomyositis, diabetes, diabetic neuropathy, diabetic retinopathy, diabetic nephropathy, diabetic ulcer, digestive system disease, eczema, emphysema, encephalitis, endocarditis, endometritis, enteritis, enterocolitis, epicondylitis, epididymitis, fasciitis, fibromyalgia, fibrosis, fibrositis, gastritis, gastroenteritis, gingivitis, glomerulonephritis, glossitis, heart disease, heart valve dysfunction, hepatitis, hidradenitis suppurativa, Huntington's disease, hyperlipidemic pancreatitis, hypertension, ileitis, infection, inflammatory bowel disease, inflammatory cardiomegaly, inflammatory neuropathy, insulin resistance, interstitial cystitis, interstitial nephritis, iritis, ischemia, ischemic heart disease, keratitis, keratoconjunctivitis, laryngitis, lupus nephritis, mastitis, mastoiditis, meningitis, metabolic syndrome (syndrome X), a migraine, multiple sclerosis, myelitis, myocarditis, myositis, nephritis, non-alcoholic steatohepatitis, obesity, omphalitis, oophoritis, orchitis, osteochondritis, osteopenia, osteomyelitis, osteoporosis, osteitis, otitis, pancreatitis, Parkinson's disease, parotitis, pelvic inflammatory disease, pemphigus vularis, pericarditis, peritonitis, pharyngitis, phlebitis, pleuritis, pneumonitis, polycystic nephritis, proctitis, prostatitis, psoriasis, pulpitis, pyelonephritis, pylephlebitis, renal failure, reperfusion injury, retinitis, rheumatic fever, rhinitis, salpingitis, sarcoidosis, sialadenitis, sinusitis, spastic colon, stenosis, stomatitis, stroke, surgical complication, synovitis, tendonitis, tendinosis, tenosynovitis, thrombophlebitis, tonsillitis, trauma, traumatic brain injury, transplant rejection, trigonitis, tuberculosis, tumor, urethritis, ursitis, uveitis, vaginitis, vasculitis, and vulvitis.

In one aspect, the present disclosure relates to a method of treating a gastrointestinal disease or disorder, wherein the method comprises administering to an individual in need thereof a pharmaceutical composition comprising a compound disclosed herein. In some embodiments, the gastrointestinal disease or disorder is selected from the group consisting of achalasia, Barrett's oesophagus, colorectal cancer, gastric cancer, oesophageal cancer, coeliac disease, colitis, Crohn's disease, diverticulosis, diverticulitis, gastritis, inflammatory bowel disease, ulcerative colitis, irritable bowel syndrome, microscopic colitis, collagenous colitis, lymphocytic colitis, pancreatitis, reflux oesophagitis, and ulcerative colitis.

In another aspect, the present disclosure relates to a method of treating an autoimmune disease, wherein the method comprises administering to an individual in need thereof a pharmaceutical composition comprising a compound disclosed herein. In some embodiments, the autoimmune disease is selected from the group consisting of lupus erythematosus; Wiskott-Aldrich syndrome; autoimmune lymphoproliferative syndrome; myasthenia gravis; rheumatoid arthritis (RA); lupus nephritis; multiple sclerosis; systemic lupus erythematosis, subacute cutaneous lupus erythematosus, cutaneous lupus erythematosus including chilblain lupus erythematosus, chronic arthritis, Sjogren's syndrome, autoimmune nephritis, autoimmune vasculitis, autoimmune hepatitis, autoimmune carditis, autoimmune encephalitis, autoimmune mediated hematological disease, inflammatory chronic rhinosinusitis, colitis, celiac disease, inflammatory bowel disease, Barrett's esophagus, and/or inflammatory gastritis.

In another aspect, the present disclosure relates to a method of treating a cancer in a subject in need thereof, comprising administering a therapeutically effective amount of the compounds disclosed herein or the pharmaceutical composition disclosed herein to the subject in need.

In some embodiments, the cancer is selected from the group consisting of an adrenal gland tumor, an AIDS-associated cancer, an alveolar soft part sarcoma, an astrocytic tumor, bladder cancer, bone cancer, a brain and spinal cord cancer, a metastatic brain tumor, a breast cancer, a carotid body tumors, a cervical cancer, a chondrosarcoma, a chordoma, a chromophobe renal cell carcinoma, a clear cell carcinoma, a colon cancer, a colorectal cancer, a cutaneous benign fibrous histiocytoma, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder or bile duct cancer, gastric cancer, a gestational trophoblastic disease, a germ cell tumor, a head and neck cancer, hepatocellular carcinoma, an islet cell tumor, a Kaposi's Sarcoma, a kidney cancer, a leukemia, a lipoma/benign lipomatous tumor, a liposarcoma/malignant lipomatous tumor, a liver cancer, a lymphoma, a lung cancer, a medulloblastoma, a melanoma, a meningioma, a multiple endocrine neoplasia, a multiple myeloma, a myelodysplastic syndrome, a neuroblastoma, a neuroendocrine tumors, an ovarian cancer, a pancreatic cancer, a papillary thyroid carcinoma, a parathyroid tumor, a pediatric cancer, a peripheral nerve sheath tumor, a phaeochromocytoma, a pituitary tumor, a prostate cancer, a posterious uveal melanoma, a rare hematologic disorder, a renal metastatic cancer, a rhabdoid tumor, a rhabdomysarcoma, a sarcoma, a skin cancer, a soft-tissue sarcoma, a squamous cell cancer, a stomach cancer, a synovial sarcoma, a testicular cancer, a thymic carcinoma, a thymoma, a thyroid metastatic cancer, and a uterine cancer.

In some embodiments, the cancer is selected from the group consisting of colorectal cancer, hepatocellular carcinoma, glioma, kidney cancer, breast cancer, multiple myeloma, bladder cancer, neuroblastoma; sarcoma, non-Hodgkin's lymphoma, non-small cell lung cancer, ovarian cancer, pancreatic cancer, a rectal cancer, acute myeloid leukemia (AML), chronic myelogenous leukemia (CML), acute B lymphoblastic leukemia (B-ALL), chronic lymphocytic leukemia (CLL), hairy cell leukemia (HCL), blastic plasmacytoid dendritic cell neoplasm (BPDCN), non-Hodgkin's lymphomas (NHL), including mantel cell leukemia (MCL), and small lymphocytic lymphoma (SLL), Hodgkin's lymphoma, systemic mastocytosis, or Burkitt's lymphoma.

As used herein, "treatment" refers to clinical intervention in an attempt to alter the natural course of the subject or cell being treated, and may be performed for prophylactic purposes or during clinical pathology. Desirable therapeutic effects include prevention of onset or recurrence of disease, alleviation of symptoms, diminishment of any direct or indirect pathological consequences of the disease, decreasing the rate of disease progression, amelioration or slowing of the disease state, and remission or improved prognosis. In some embodiments, the development of a disease or disorder is delayed using a pharmaceutical composition of the invention.

"Inhibiting growth" of a tumor or cancer cells as used herein may refer to slowing the rate of tumor or cancer cell growth, or halting tumor or cancer cell growth entirely.

As used herein, "tumor" refers to the growth and proliferation of all neoplastic cells (malignant or benign), and all precancerous and cancerous cells and tissues. As referred to herein, the terms "cancer", "cancerous", "cell proliferative disorder", "proliferative disorder" and "tumor" are not mutually exclusive.

The terms "cancer" and "cancerous" refer to or describe the physiological condition in mammals that is typically characterized by unregulated cell growth/proliferation. Examples of cancer include, but are not limited to, carcinoma, lymphoma (such as Hodgkin's lymphoma and non-Hodgkin's lymphoma), blastoma, sarcoma, and leukemia. More specific examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia, and other lymphoproliferative disorders, as well as various types of head and neck cancer.

"Tumor regression" or "regression" of an tumor as used herein may refer to reducing the size or maximum size of a tumor. Tumor size can be determined by for example bioluminescence based assays.

Compounds

In one aspect, the present disclosure relates to a compound having a structure according to Formula Ia or Formula Ib set forth below:

Formula Ia

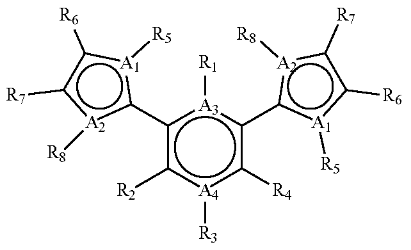

Formula Ia

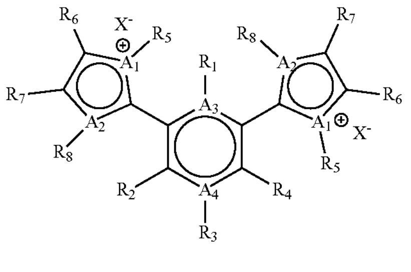

or a pharmaceutically acceptable ester or solvate thereof, wherein $X^-$ is an ion of an acid forming a pharmaceutically acceptable salt, where $A_1$, $A_2$, $A_3$, and $A_4$ are independently selected from nitrogen (N) or Carbon (C), wherein $R_1$, $R_2$, $R_3$, $R_4$, $R_5$, $R_6$, $R_7$, and $R_8$ are independently selected from the group consisting of nothing, H, OH, protected hydroxyl, alkyl, alkenyl, alkynyl, acyl, aryl, heteroaryl, cycloalkyl, and heterocycle; wherein $R_1$ is nothing if $A_3$ is N; wherein $R_3$ is nothing if $A_4$ is N; wherein the alkyl, alkenyl, alkynyl or acyl is optionally substituted with one or more substituents independently selected from the group consisting of halogen, —OH, alkyl, —O-alkyl, $NR^AR^B$, —S-alkyl, —SO-alkyl, —$SO_2$-alkyl, alkenyl, alkynyl, aryl, heteroaryl, cycloalkyl, and heterocycle; wherein $R^A$ and $R^B$ are each independently selected from hydrogen and $C_{1-4}$ alkyl; wherein the aryl or heteroaryl, whether alone or as part of a substituent group, is optionally substituted with one or more substituents independently selected from the group consisting of halogen, —OH, alkyl, —O-alkyl, —COOH, —C(O)—$C_{1-4}$ alkyl, —C(O)O—$C_{1-4}$ alkyl, $NR^CR^D$, —S-alkyl, —SO-alkyl and —$SO_2$-alkyl; wherein $R^C$ and $R^D$ are each independently selected from hydrogen and $C_{1-4}$ alkyl.

In some embodiments, $R_2$ and/or $R_4$ has the structure according to Formula IIa or Formula IIb:

Formula IIa

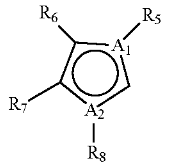

Formula IIb

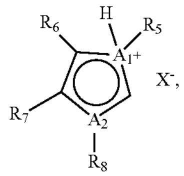

wherein $X^-$, $A_1$, $A_2$, $R_5$, $R_6$, $R_7$, and $R_8$ are defined as above.

In some embodiments, $A_1$ and $A_3$ are N, $A_4$ is C, and $R_3$ has the structure according to Formula IIa or Formula IIb.

In some embodiments, $A_2$ is C.

In some embodiments, $A_1$ is N, and/or $A_3$ and/or $A_4$ is N.

In some embodiments, $A_2$ is C.

In some embodiments, $R_2$ and $R_4$ have the structure according to Formula IIa or Formula IIb.

In some embodiments, the compound has a structure selected from the group consisting of:

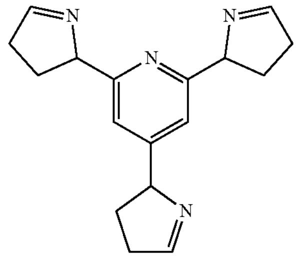

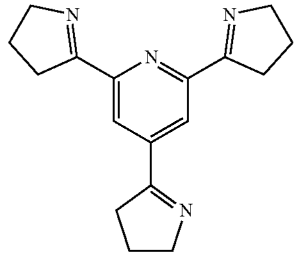

-continued

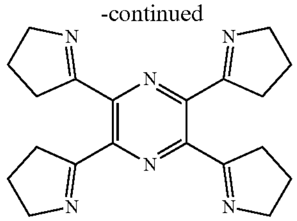

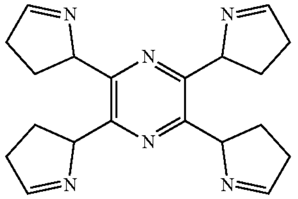

and

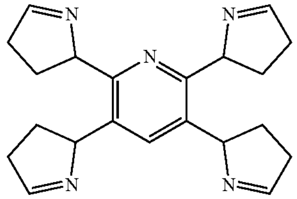

or a pharmaceutically acceptable salt, ester or solvate thereof.

According to one aspect of the present disclosure, an anti-inflammatory compound has the structure:

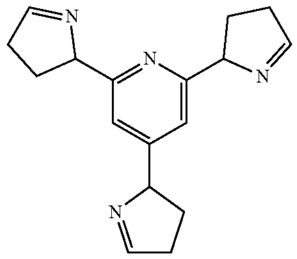 [SMILES: C1=NC(c2cc(C3CCC=N3)nc(C3CCC=N3)c2)CC1]

or a pharmaceutically acceptable salt, ester or solvate thereof.

In one aspect, the present disclosure relates to a compound having the structure:

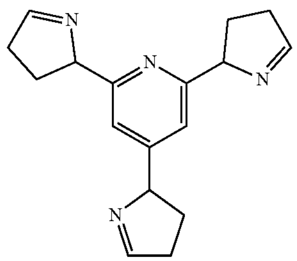

2,4,6-tris(3,4-dihydro-2H-pyrrol-2-yl)pyridine or a pharmaceutically acceptable salt, ester, or solvate thereof.

In some embodiments, the present disclosure relates to a compound having a structure according to Formula IIIa or Formula IIIb set forth below:

Formulat IIIa

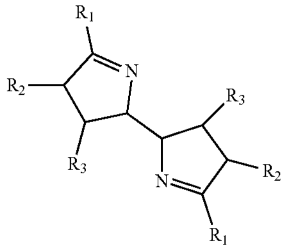

Formula IIIb

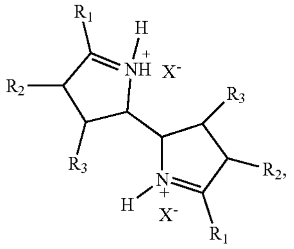

or a pharmaceutically acceptable ester or solvate thereof, wherein $X^-$ is an ion of an acid forming a pharmaceutically acceptable salt, wherein $R_1$, $R_2$, and $R_3$ are independently selected from the group consisting of H, OH, protected hydroxyl, alkyl, alkenyl, alkynyl, acyl, aryl, heteroaryl, cycloalkyl, and heterocycle; wherein the alkyl, alkenyl, alkynyl or acyl is optionally substituted with one or more substituents independently selected from the group consisting of halogen, —OH, alkyl, —O-alkyl, $NR^AR^B$, —S-alkyl, —SO-alkyl, —$SO_2$-alkyl, alkenyl, alkynyl, aryl, heteroaryl, cycloalkyl, and heterocycle; wherein $R^A$ and $R^B$ are each independently selected from hydrogen and $C_{1-4}$ alkyl; wherein the aryl or heteroaryl, whether alone or as part of a substituent group, is optionally substituted with one or more substituents independently selected from the group consisting of halogen, —OH, alkyl, —O-alkyl, —COOH, —C(O)—$C_{1-4}$ alkyl, —C(O)O—$C_{1-4}$ alkyl, $NR^CR^D$, —S-alkyl, —SO-alkyl and —$SO_2$-alkyl; wherein $R^C$ and $R^D$ are each independently selected from hydrogen and $C_{1-4}$ alkyl.

In some embodiments, the compound has the following structure:

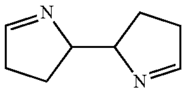

, or a pharmaceutically acceptable salt, ester or solvate thereof.

In some embodiments, the present disclosure relates to a compound having a structure according to Formula IVa or Formula IVb set forth below:

Formula IVa

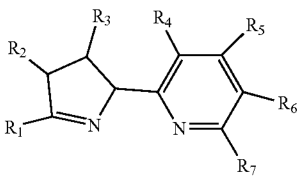

-continued

Formula IVb

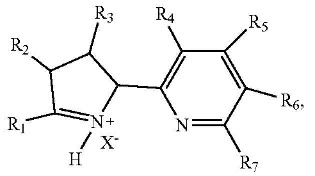

or a pharmaceutically acceptable ester or solvate thereof, wherein $X^-$ is an ion of an acid forming a pharmaceutically acceptable salt, wherein $R_1$, $R_2$, $R_3$, $R_4$, $R_5$, $R_6$, and $R_7$ are independently selected from the group consisting of H, OH, protected hydroxyl, alkyl, alkenyl, alkynyl, acyl, aryl, heteroaryl, cycloalkyl, and heterocycle; wherein the alkyl, alkenyl, alkynyl or acyl is optionally substituted with one or more substituents independently selected from the group consisting of halogen, —OH, alkyl, —O-alkyl, $NR^AR^B$, —S-alkyl, —SO-alkyl, —$SO_2$-alkyl, alkenyl, alkynyl, aryl, heteroaryl, cycloalkyl, and heterocycle; wherein $R^A$ and $R^B$ are each independently selected from hydrogen and $C_{1-4}$ alkyl; wherein the aryl or heteroaryl, whether alone or as part of a substituent group, is optionally substituted with one or more substituents independently selected from the group consisting of halogen, —OH, alkyl, —O-alkyl, —COOH, —C(O)—$C_{1-4}$ alkyl, —C(O)O—$C_{1-4}$ alkyl, $NR^CR^D$, —S-alkyl, —SO-alkyl and —$SO_2$-alkyl; wherein $R^C$ and $R^D$ are each independently selected from hydrogen and $C_{1-4}$ alkyl.

In some embodiments, the compound has the following structure:

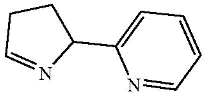 [SMILES: C1=NC(c2ccccn2)CC1]

or a pharmaceutically acceptable salt, ester or solvate thereof.

In another aspect, the present disclosure relates to a compound having a structure according to Formula Va or Formula Vb set forth below:

Formula Va

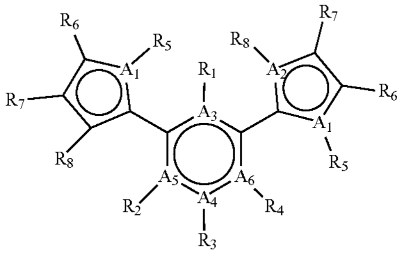

-continued

Formula Vb

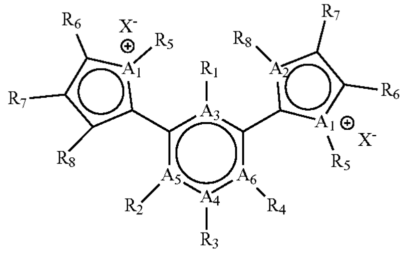

or a pharmaceutically acceptable ester or solvate thereof, wherein $X^-$ is an ion of an acid forming a pharmaceutically acceptable salt, where $A_1$, $A_2$, $A_3$, $A_4$, $A_5$, and $A_6$ are independently selected from nitrogen (N) or Carbon (C), wherein $R_1$, $R_2$, $R_3$, $R_4$, $R_5$, $R_6$, $R_7$, and $R_8$ are independently selected from the group consisting of nothing, H, OH, protected hydroxyl, alkyl, alkenyl, alkynyl, acyl, aryl, heteroaryl, cycloalkyl, and heterocycle; wherein $R_1$ is nothing if $A_3$ is N; wherein $R_3$ is nothing if $A_4$ is N; wherein the alkyl, alkenyl, alkynyl or acyl is optionally substituted with one or more substituents independently selected from the group consisting of halogen, —OH, alkyl, —O-alkyl, $NR^AR^B$, —S-alkyl, —SO-alkyl, —$SO_2$-alkyl, alkenyl, alkynyl, aryl, heteroaryl, cycloalkyl, and heterocycle; wherein $R^A$ and $R^B$ are each independently selected from hydrogen and $C_{1-4}$ alkyl; wherein the aryl or heteroaryl, whether alone or as part of a substituent group, is optionally substituted with one or more substituents independently selected from the group consisting of halogen, —OH, alkyl, —O-alkyl, —COOH, —C(O)—$C_{1-4}$ alkyl, —C(O)O—$C_{1-4}$ alkyl, $NR^CR^D$, —S-alkyl, —SO-alkyl and —$SO_2$-alkyl; wherein $R^C$ and $R^D$ are each independently selected from hydrogen and $C_{1-4}$ alkyl. In some embodiments, $R_2$ and/or $R_4$ has the structure according to Formula IIa or Formula IIb, and wherein $X^-$, $A_1$, $A_2$, $R_5$, $R_6$, $R_7$, and $R_8$ are defined as above. In some embodiments, A1 and A3 are N, A4, A5, and A6 are C, and $R_3$ has the structure according to Formula IIa or Formula IIb. In some embodiments, A1 and A3 are N, A4 is C, A5 or A6 is N and $R_3$ has the structure according to Formula IIa or Formula IIb. In some embodiments, $A_1$, $A_3$, and $A_4$ are N, $A_5$ and $A_6$ are C, and $R_3$ has the structure according to Formula IIa or Formula IIb. In some embodiments, $A_2$ is C. In some embodiments, $A_1$ is N, and/or $A_3$ and/or $A_4$ is N. In some embodiments, $R_2$ and $R_4$ have the structure according to Formula IIa or Formula IIb.

In some embodiments, the compound according to formula Va or Vb has the structure:

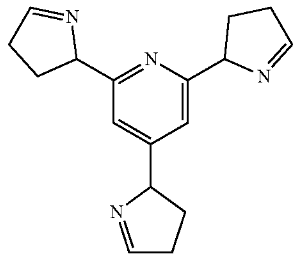 [SMILES: C1=NC(c2cc(C3CCC=N3)nc(C3CCC=N3)c2)CC1]

or a pharmaceutically acceptable salt, ester or solvate thereof.

In some embodiments, the compound according to formula Va or Vb has a structure selected from the group consisting of:

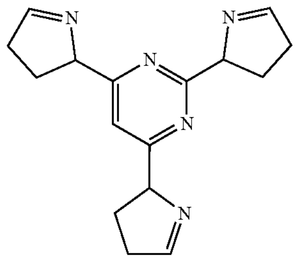

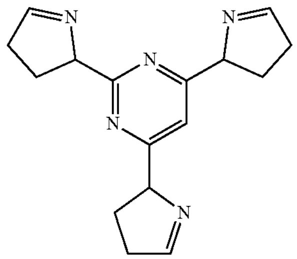

or a pharmaceutically acceptable salt, ester or solvate thereof.

In some embodiments, the compound according to formula Va or Vb has the structure:

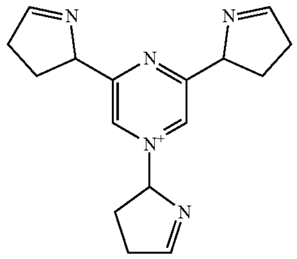 [SMILES: C1=NC(c2c[n+](C3CCC=N3)cc(C3CCC=N3)n2)CC1]

or a pharmaceutically acceptable salt, ester or solvate thereof.

In some embodiments, the compound according to formula Va or Vb has a structure selected from the group consisting of:

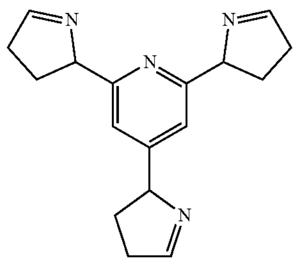

-continued

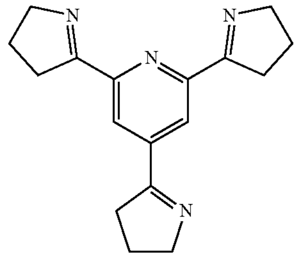

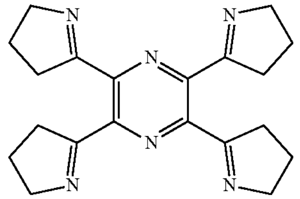

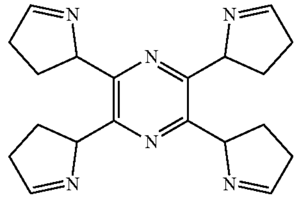

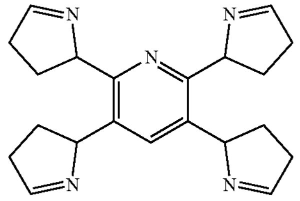

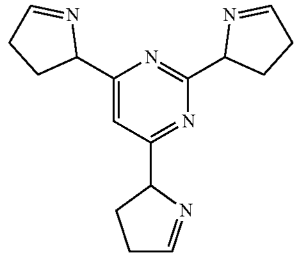

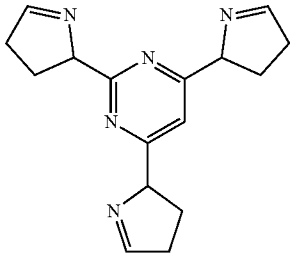

and

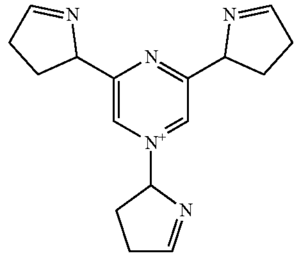 [SMILES: C1=NC(c2c[n+](C3CCC=N3)cc(C3CCC=N3)n2)CC1]

or a pharmaceutically acceptable salt, ester or solvate thereof.

In some embodiments, the compound according to formula Va or Vb has a structure selected from the group consisting of:

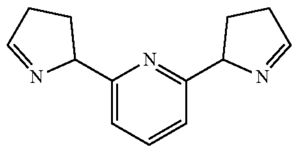

and

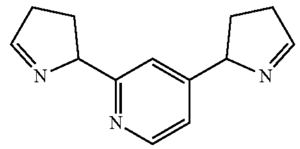

or a pharmaceutically acceptable salt, ester or solvate thereof.

In another aspect, the present disclosure relates to a compound having a structure according to Formula VIa, Formula VIb or Formula VIc set forth below:

Formula VIa

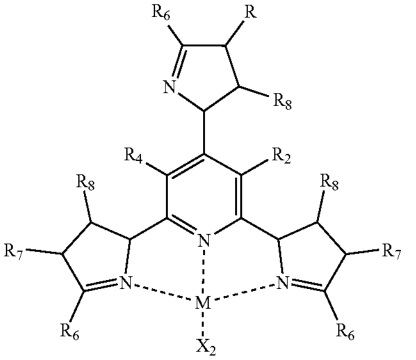

Formula VIb

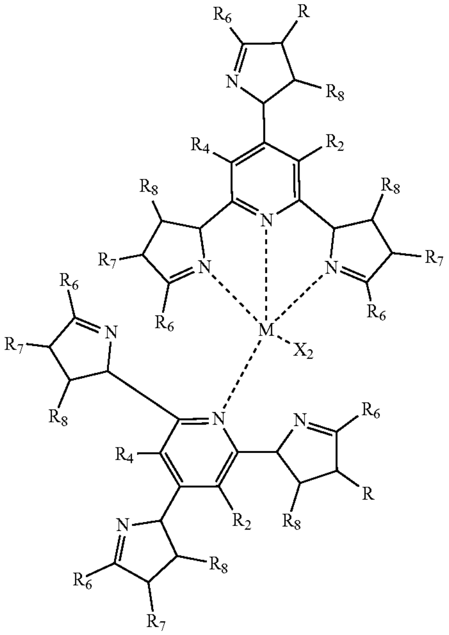

-continued

Formula VIc

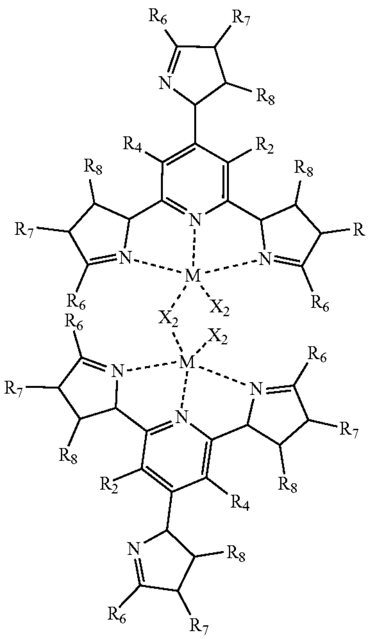

wherein each $R_2$, $R_4$, $R_6$ $R_7$, and $R_8$ is independently as previously defined, each $X_2$ is independently an ion of an acid forming a pharmaceutically acceptable salt, and each M is independently a transition metal selected from the group consisting of scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, and gold. Multivalent transition metals may be present in any of their respective valences.

In some examples, M is zinc. In other examples, M is silver such as $Ag^+$ or $Ag^{2+}$. In some examples, each $X_2$ is Br. In other examples, each $X_2$ is Cl.

In another aspect, the present disclosure relates to a compound having a structure according to Formula VII set forth below:

Formula VII

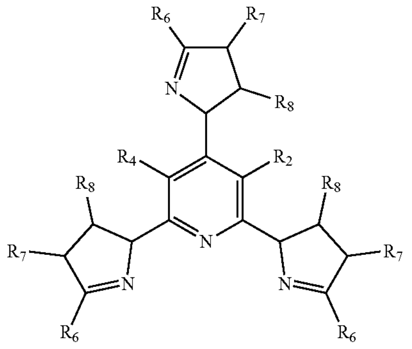

wherein $R_2$ and $R_4$ are independently H, halogen or a calcium ion chelator group, with the proviso that $R_2$ and $R_4$ are not both hydrogen; and each $R_6$, $R_7$ and $R_8$ is independently as previously defined;

or a pharmaceutically acceptable salt, ester or solvate thereof.

In some examples of compounds of Formula VII, $R_2$ and $R_4$ are each independently H, F, a residue of carboxylic acid (—COOH), carboxylate (—COO—), hydroxyl (—OH), or amine (—$NH_2$), with the proviso that $R_2$ and $R_4$ are not both hydrogen.

While not wanting to be bound by theory, it is believed that the presence of a calcium ion chelator group, such as carboxylate (—COO—), hydroxyl (—OH), or amine (—$NH_2$), may enhance the inhibitory effect on Store-Operated Calcium Entry (SOCE) via inhibition of Calcium Release-Activated Calcium (CRAC) channels as well as currents carried by the channel-kinase Transient Receptor Potential Melastatin 7 (TRPM7). TRPM7 is a bifunctional molecule that acts as both a channel and a kinase. The kinase domain activates downstream target proteins that affect cell proliferation, inflammatory responses, and vascular contraction. TRPM7 significantly impacts viral replication by regulating the pH level within the cell, particularly in the endosomal compartment, where many enveloped viruses require acidic conditions to fuse with the host cell membrane and initiate infection. TRPM7 activity is crucial for maintaining the necessary acidic pH in endosomes, thus facilitating viral entry and replication for viruses that rely on low pH for fusion. See C. A. Doyle et al., "Endosomal fusion of pH-dependent enveloped viruses requires ion channel TRPM7," *Nature Communications* 2024 15:8479.

TRPM7 kinase activity induces amyloid-O degradation to reverse synaptic and cognitive deficits in mouse models of Alzheimer's disease. TRPM7 affects many aspects of the body, including the brain, heart, and immune system. TRPM7 expression is decreased in Alzheimer's disease (AD) and Parkinson's disease. See Y. Sun et al., "TRPM7 and its role in neurodegenerative diseases," *Channels* 9:5, 253-261; September/October 2015. TRPM7 also is involved in regulating synaptic density and learning and memory. TRPM7 protects against inflammation and fibrosis in the cardiovascular system. TRPM7 plays a role in hypertension. TRPM7 also is involved in autoimmune diseases such as rheumatoid arthritis, multiple sclerosis, and diabetes. TRPM7 is important for neutrophil recruitment during inflammation. TRPM7 is involved in vascular regulation. TRPM7 regulates breathing during sleep in obesity. TRPM7 is involved in tumor progression. TRPM7 channel-kinase also may affect telomeres by modifying histone phosphorylation, which can impact DNA damage and cell senescence.

In some embodiments, a compound according to Formula VII has a structure selected from the group consisting of:

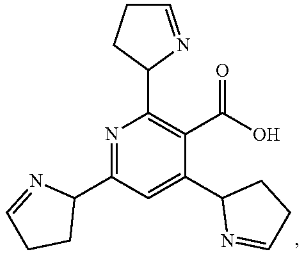
,

-continued

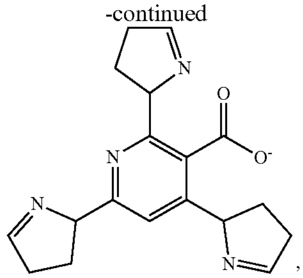
,

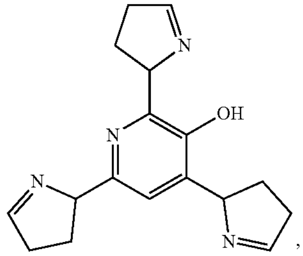
,

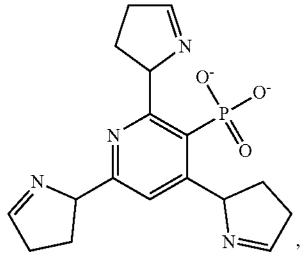
,

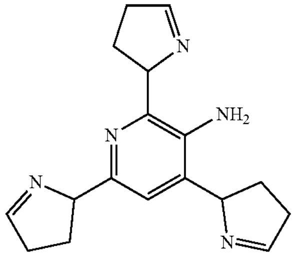
and

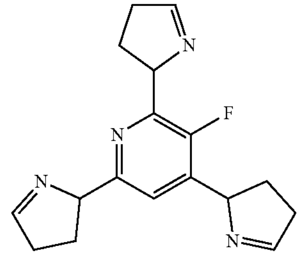

or a pharmaceutically acceptable salt, ester or solvate thereof.

Pharmaceutical Compositions

A pharmaceutical composition may include a pharmaceutically acceptable carrier that facilitates processing of an active ingredient into pharmaceutically acceptable compositions. As used herein, the term "pharmacologically acceptable carrier" is synonymous with "pharmacological carrier" and means any carrier that has substantially no long term or permanent detrimental effect when administered and encompasses terms such as "pharmacologically acceptable vehicle," "stabilizer," "diluent," "additive," "auxiliary" or "excipient." Pharmaceutically acceptable carriers are generally safe, non-toxic, and include excipients that are acceptable for veterinary use as well as for human pharmaceutical use. Such a carrier generally is mixed with an active compound or permitted to dilute or enclose the active compound and can be a solid, semi-solid, or liquid agent. It is understood that the active ingredients can be soluble or can be delivered as a suspension in the desired carrier or diluent. Any of a variety of pharmaceutically acceptable carriers can be used including, without limitation, aqueous media such as, e.g., water, saline, glycine, hyaluronic acid and the like; solid carriers such as, e.g., mannitol, lactose, starch, magnesium stearate, sodium saccharin, talcum, cellulose, glucose, sucrose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in Pharmaceutical Dosage Forms and Drug Delivery Systems (Howard C. Ansel et al., eds., Lippincott Williams & Wilkins Publishers, 7th ed. 1999); REMINGTON: THE SCIENCE AND PRACTICE OF PHARMACY (Alfonso R. Gennaro ed., Lippincott, Williams & Wilkins, 20th ed. 2000); Goodman & Gilman's The Pharmacological Basis of Therapeutics (Joel G. Hardman et al., eds., McGraw-Hill Professional, 10th ed. 2001); and Handbook of Pharmaceutical Excipients (Raymond C. Rowe et al., APhA Publications, 4th edition 2003). These protocols are routine procedures and any modifications are well within the scope of one skilled in the art and from the teaching herein.

In various embodiments, the present invention provides a kit for treating, preventing, reducing the severity of and/or slowing the progression of the conditions or diseases described herein in a subject. The kit is an assemblage of materials or components, including at least one of the compounds disclosed herein. Thus, in some embodiments the kit contains a composition including a drug delivery molecule complexed with a therapeutic compound, as described above. The exact nature of the components configured in the inventive kit depends on its intended purpose. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals. Instructions for use may be included in the kit. "Instructions for use" typically include a tangible expression describing the technique to be employed in using the components of the kit to affect a desired outcome. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art. The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components.

Compounds intended for administration to humans or other mammals generally should have very high purity. Purity refers to the ratio of a compound's mass to the total sample mass following any purification steps. Usually, the level of purity is at least about 95%, more usually at least about 96%, about 97%, about 98%, or higher. For example, the level of purity may be about 98.5%, 99.0%, 99.1%, 99.2%, 99.3%, 99.4%, 99.5%, 99.6%, 99.7%, 99.8%, 99.9%, or higher.

Compound described herein that exist in more than one optical isomer form (enantiomer) may be provided either as racemic mixture or by isolating one of the enantiomers, the latter case in which purity as described above may refer to enantiomeric purity. The present disclosure is meant to include all possible optical isomeric forms or enantiomers of the disclosed compounds, the compositions containing mixtures of such enantiomers and enantiomeric pure forms or racemic mixtures, or enantiomerically enriched mixtures, or (when more than a single chiral center is present), diastereomerically pure compounds, or diastereomeric mixtures in any relative proportions.

Enantiomers may be prepared or isolated using for examples chiral synthesis from a suitable optically pure precursor or resolution of the racemate (or the racemate of a salt or derivative) using, for example, chiral high pressure liquid chromatography (HPLC). "Enantiomers" are a pair of stereoisomers that are non-superimposable mirror images of each other. A 1:1 mixture of a pair of enantiomers is a "racemic" mixture. A mixture of enantiomers at a ratio other than 1:1 is a "scalemic" mixture. "Diastereoisomers" are stereoisomers that have at least two asymmetric atoms or a chirality axe, but which are not mirror-images of each other. A "tautomer" refers to a proton shift from one atom of a molecule to another atom of the same molecule. The present disclosure includes tautomers of any compounds provided herein.

"Isolated optical isomer" means a compound which has been substantially purified from the corresponding optical isomer(s) of the same formula. Preferably, the isolated isomer is at least about 80%, more preferably at least 90% pure, even more preferably at least 98% pure, most preferably at least about 99% pure, by weight. Compounds of the present invention are provided in any of these degrees of enantiomeric purity, e.g., a racemic mixture of enantiomers (50% enantiomerically pure), or 60% enantiomerically pure, 70% enantiomerically pure, 80% enantiomerically pure, or 90% enantiomerically pure, or 98% enantiomerically pure, or 99+% enantiomerically pure.

A "solvate" is formed by the interaction of a solvent and a compound. Solvates of salts of the compounds provided herein are also provided. Hydrates of the compounds provided herein are also provided.

A "prodrug" is a biologically inactive derivative of a drug that upon administration to the human body is converted to the biologically active parent drug according to some chemical or enzymatic pathway.

The compounds described herein may be prepared synthetically using techniques such as those described in M. ELLIS, "PART I: THE TOTAL SYNTHESIS OF MYOSMINE AND APOFERROROSAMINE, PART II: STUDIES ON THE POTENTIAL OF ISOXAZOLES AS GENERAL SYNTHETIC INTERMEDIATES," (1971) Diss., Rice University, (hdl.handle.net/1911/14718), with appropriate modifications to reagents to obtain the disclosed structures as will be apparent to persons skilled in the art with the aid of no more than routine experimentation.

In some aspects, a compound may be converted into a pharmaceutically acceptable salts using techniques well known to persons skilled in the art. For example, salts such as sodium and potassium salts may be prepared by treating the compound with a suitable sodium or potassium base, such as sodium hydroxide or potassium hydroxide, respectively. Esters and ethers of the compound may be prepared as described, e.g., in Advanced Organic Chemistry, 1992, 4th Edition, J. March, John Wiley & Sons, or J. Med. Chemistry, 1992, 35, 145-151.

Compositions as described herein may be administered orally, nasally, topically, subcutaneously, intramuscularly, intravenously, or by other modes of administration known to persons skilled in the art.

A pharmaceutical composition may optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and means for adjusting pH can be used to prepare a pharmaceutical composition disclosed herein, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate, a stabilized oxy chloro composition and chelants, such as, e.g., DTPA or DTPA-bisamide, calcium DTPA, and CaNaDTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition.

Examples of auxiliaries and/or excipients that may be mentioned are cremophor, poloxamer, benzalkonium chloride, sodium lauryl sulfate, dextrose, glycerin, magnesium stearate, polyethylene glycol, starch, dextrin, lactose, cellulose, carboxymethylcellulose sodium, talc, agar-agar, mineral oil, animal oil, vegetable oil, organic and mineral waxes, paraffin, gels, propylene glycol, benzyl alcohol, dimethylacetamide, ethanol, polyglycols, tween 80, solutol HS 15, and water. It is also possible to administer the active substances as such, without vehicles or diluents, in a suitable form, for example, in capsules.

A pharmaceutical composition may comprise a therapeutic compound in an amount sufficient to allow customary administration to an individual. A unit dose form may have, e.g., at least 5 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, or at least 100 mg of a therapeutic compound. In other aspects, a unit dose form may have, e.g., at least 200 mg, at least 300 mg, at least 400 mg, at least 500 mg, at least 600 mg, at least 700 mg, at least 800 mg, at least 900 mg, at least 1,000 mg, at least 1,100 mg, at least 1,200 mg, at least 1,300 mg, at least 1,400 mg, or at least 1,500 mg of a therapeutic compound. In yet other aspects of this embodiment, a pharmaceutical composition disclosed herein may include, e.g., about 5 mg to about 100 mg, about 10 mg to about 100 mg, about 50 mg to about 150 mg, about 100 mg to about 250 mg, about 150 mg to about 350 mg, about 250 mg to about 500 mg, about 350 mg to about 600 mg, about 500 mg to about 750 mg, about 600 mg to about 900 mg, about 750 mg to about 1,000 mg, about 850 mg to about 1,200 mg, or about 1,000 mg to about 1,500 mg of a therapeutic compound. In still other aspects of this embodiment, a pharmaceutical composition disclosed herein may include, e.g., about 10 mg to about 250 mg, about 10 mg to about 500 mg, about 10 mg to about 750 mg, about 10 mg to about 1,000 mg, about 10 mg to about 1,500 mg, about 50 mg to about 250 mg, about 50 mg to about 500 mg, about 50 mg to about 750 mg, about 50 mg to about 1,000 mg, about 50 mg to about 1,500 mg, about 100 mg to about 250 mg, about 100 mg to about 500 mg, about 100 mg to about 750 mg, about 100 mg to about 1,000 mg, about 100 mg to about 1,500 mg, about 200 mg to about 500 mg, about 200 mg to about 750 mg, about 200 mg to about 1,000 mg, about 200 mg to about 1,500 mg, about 5 mg to about 1,500 mg, about 5 mg to about 1,000 mg, or about 5 mg to about 250 mg of a therapeutic compound.

Pharmaceutical compositions as described herein may include a pharmaceutically acceptable solvent. A solvent is a liquid, solid, or gas that dissolves another solid, liquid, or gaseous (the solute), resulting in a solution. Solvents useful in the pharmaceutical compositions include, without limitation, a pharmaceutically acceptable polar aprotic solvent, a pharmaceutically acceptable polar protic solvent and a pharmaceutically acceptable non-polar solvent. A pharmaceutically acceptable polar aprotic solvent includes, without limitation, dichloromethane (DCM), tetrahydrofuran (THF), ethyl acetate, acetone, dimethylformamide (DMF), acetonitrile (MeCN), dimethyl sulfoxide (DMSO). A pharmaceutically acceptable polar protic solvent includes, without limitation, acetic acid, formic acid, ethanol, n-butanol, 1-butanol, 2-butanol, isobutanol, sec-butanol, tert-butanol, n-propanol, isopropanol, 1,2 propan-diol, methanol, glycerol, and water. A pharmaceutically acceptable non-polar solvent includes, without limitation, pentane, cyclopentane, hexane, cyclohexane, benzene, toluene, 1,4-dioxane, chloroform, n-methyl-pyrrolidone (NMP), and diethyl ether.

The method of administration as well as the dosage range which are suitable in a specific case depend on the species to be treated and on the state of the respective condition or disease, and may be optimized using techniques known in the art. Most often, the daily dose of active compound in a patient may range from 0.0005 mg to 15 mg per kg, or from 0.001 mg to 7.5 mg per kg. A therapeutically effective amount of a therapeutic compound disclosed herein may generally be in the range of about 0.001 mg/kg/day to about 100 mg/kg/day. An effective amount may be, e.g., at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day. In some examples, an effective amount of a therapeutic compound may be in the range of about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day. In other examples, an effective amount of a therapeutic compound disclosed herein may be in the range of, e.g., about 0.01 mg/kg/day to about 10 mg/kg/day, about 0.01 mg/kg/day to about 15 mg/kg/day, about 0.01 mg/kg/day to about 20 mg/kg/day, about 0.01 mg/kg/day to about 25 mg/kg/day, about 0.01 mg/kg/day to about 30 mg/kg/day, about 0.01 mg/kg/day to about 35 mg/kg/day, about 0.01 mg/kg/day to about 40 mg/kg/day, about 0.01 mg/kg/day to about 45 mg/kg/day, about 0.01 mg/kg/day to about 50 mg/kg/day, about 0.01 mg/kg/day to about 75 mg/kg/day, or about 0.01 mg/kg/day to about 100 mg/kg/day.

Dosing can be single dosage or cumulative (serial dosing), and can be readily determined by one skilled in the art. For instance, treatment may comprise a one-time administration of an effective dose of a pharmaceutical composition as disclosed herein. Alternatively, treatment may comprise multiple administrations of an effective dose of a pharmaceutical composition carried out over a range of time periods, such as, e.g., once daily, twice daily, trice daily, once every few days, or once weekly. The timing of administration can vary from individual to individual, depending upon such factors as the severity of an individual's symptoms. For example, an effective dose of a pharmaceutical composition disclosed herein can be administered to an individual once daily for an indefinite period of time, or until the individual no longer requires therapy. A person of ordinary skill in the art will recognize that the condition of the individual can be monitored throughout the course of treatment and that the effective amount of a pharmaceutical composition disclosed herein that is administered can be adjusted accordingly.

Pharmaceutical compositions may contain any conventional non-toxic pharmaceutically acceptable carriers, adjuvants or vehicles. In some cases, the pH of the formulation may be adjusted with acceptable pharmaceutical or food grade acids, bases or buffers to enhance the stability of the formulated composition or its delivery form.

Liquid dosage forms for oral administration include acceptable pharmaceutical or food grade emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylsulfoxide (DMSO) dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, lozenges, pills, powders, and granules. In such solid dosage forms, the active compound is mixed with at least one inert, acceptable pharmaceutical or food grade excipient or carrier such as sodium citrate or dicalcium phosphate and/or a) fillers or extenders such as starches, lactose, sucrose, glucose, mannitol, and silicic acid, b) binders such as carboxymethylcellulose, alginates, gelatin, polyvinylpyrrolidone, sucrose and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as cetyl alcohol and glycerol monostearate, h) absorbents such as kaolin and bentonite clay, i) lubricants such as talc, calcium stearate, magnesium stearate, solid polyethylene glycols, sodium lauryl sulfate, and mixtures thereof, and j) sweetening, flavoring, perfuming agents, and mixtures thereof. In the case of capsules, lozenges, tablets and pills, the dosage form may also comprise buffering agents.

The solid dosage forms of tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract or, optionally, in a delayed or extended manner. Examples of embedding compositions which can be used include polymeric substances and waxes. Tablet formulations for extended release are also described in U.S. Pat. No. 5,942,244.

Compositions may contain a compound as disclosed herein, alone or with other therapeutic compound(s). A therapeutic compound is a compound that provides pharmacological activity or other direct effect in the diagnosis, cure, mitigation, treatment, or prevention of disease, or to affect the structure or any function of the body of man or animals. A therapeutic compound disclosed herein may be used in the form of a pharmaceutically acceptable salt, solvate, or solvate of a salt, e.g., a hydrochloride. Additionally, therapeutic compound disclosed herein may be provided as racemates, or as individual enantiomers, including an R- or S-enantiomer. Thus, the therapeutic compound disclosed herein may comprise an R-enantiomer only, a S-enantiomer only, or a combination of both an R-enantiomer and a S-enantiomer of a therapeutic compound. In some aspects, the therapeutic compound may have anti-inflammatory activity, such as a non-steroidal anti-inflammatory drug (NSAID). NSAIDs are a large group of therapeutic compounds with analgesic, anti-inflammatory, and anti-pyretic properties. NSAIDs reduce inflammation by blocking cyclooxygenase. NSAIDs include, without limitation, aceclofenac, acemetacin, actarit, alcofenac, alminoprofen, amfenac, aloxipirin, aminophenazone, antraphenine, aspirin, azapropazone, benorilate, benoxaprofen, benzydamine, butibufen, celecoxib, chlorthenoxacin, choline salicylate, clometacin, dexketoprofen, diclofenac, diflunisal, emorfazone, epirizole; etodolac, etoricoxib, feclobuzone, felbinac, fenbufen, fenclofenac, flurbiprofen, glafenine, hydroxylethyl salicylate, ibuprofen, indometacin, indoprofen, ketoprofen, ketorolac, lactyl phenetidin, loxoprofen, lumiracoxib, mefenamic acid, meloxicam, metamizole, metiazinic acid, mofebutazone, mofezolac, nabumetone, naproxen, nifenazone, niflumic acid, oxametacin, phenacetin, pipebuzone, pranoprofen, propyphenazone, proquazone, protizinic acid, rofecoxib, salicylamide, salsalate, sulindac, suprofen, tiaramide, tinoridine, tolfenamic acid, valdecoxib, and zomepirac.

NSAIDs may be classified based on their chemical structure or mechanism of action. Non-limiting examples of NSAIDs include a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclooxygenase (COX) inhibitor, a selective cyclooxygenase-1 (COX-1) inhibitor, and a selective cyclooxygenase-2 (COX-2) inhibitor. An NSAID may be a profen. Examples of a suitable salicylate derivative NSAID include, without limitation, acetylsalicylic acid (aspirin), diflunisal, and salsalate. Examples of a suitable p-amino phenol derivative NSAID include, without limitation, paracetamol and phenacetin. Examples of a suitable propionic acid derivative NSAID include, without limitation, alminoprofen, benoxaprofen, dexketoprofen, fenoprofen, flurbiprofen, ibuprofen, indoprofen, ketoprofen, loxoprofen, naproxen, oxaprozin, pranoprofen, and suprofen. Examples of a suitable acetic acid derivative NSAID include, without limitation, aceclofenac, acemetacin, actarit, alcofenac, amfenac, clometacin, diclofenac, etodolac, felbinac, fenclofenac, indometacin, ketorolac, metiazinic acid, mofezolac, nabumetone, naproxen, oxametacin, sulindac, and zomepirac. Examples of a suitable enolic acid (oxicam) derivative NSAID include, without limitation, droxicam, isoxicam, lornoxicam, meloxicam, piroxicam, and tenoxicam. Examples of a suitable fenamic acid derivative NSAID include, without limitation, flufenamic acid, mefenamic acid, meclofenamic acid, and tolfenamic acid. Examples of suitable selective COX-2 inhibitors include, without limitation, celecoxib, etoricoxib, firocoxib, lumiracoxib, meloxicam, parecoxib, rofecoxib, and valdecoxib.

In some examples, compounds described herein may be co-administered with therapeutic compounds that have an inhibitory effect on Store-Operated Calcium Entry (SOCE) via inhibition of Calcium Release-Activated Calcium (CRAC) channels as well as currents carried by the channel-kinase TRPM7. Non-limiting examples of such compounds include acidic cannabinoids such as cannabigerolic acid (CBGA). Such co-therapies may be particularly beneficial for treating diseases in which TRPM7 is known to play an important role, such as cancer, stroke, and kidney disease.

In some examples, compounds and compositions as described herein may be administered to individuals to prevent formation of metal oxides. In other examples, the compounds may be used to prevent formation of metal oxides in industrial applications such as in surface treatments including descaling, pickling, and removing surface deposits and corrosion products.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed subject-matter, because the scope of the present technology is limited only by the claims. Unless otherwise defined, all technical and scientific terms used herein have the same meaning as commonly understood by one of ordinary skill in the art to which this present technology belongs. If there is an apparent discrepancy between the usage of a term in the art and its definition provided herein, the definition provided within the specification shall prevail.

As used in this specification and the appended claims, the singular forms "a," "an" and "the" include plural referents unless the content clearly dictates otherwise. For example, reference to "a cell" includes a combination of two or more cells, and the like.

As used herein, the term "approximately" or "about" in reference to a value or parameter are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value). As used herein, reference to "approximately" or "about" a value or parameter includes (and describes) embodiments that are directed to that value or parameter. For example, description referring to "about X" includes description of "X".

As used herein, the term "or" means "and/or." The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the present technology.

The terms "individual (individual)", "subject", or "patient" are used interchangeably herein. In some embodiments the patient or subject is a vertebrate. The term subjects may be a human or a veterinary subject. In certain embodiments, the vertebrate is a mammal. The term "mammal" for therapeutic purposes refers to any animal classified as a mammal, including humans, domestic and farm animals, and zoo, sports, or pet animals, such as dogs, horses, cats, cattle, etc. In certain embodiments, the mammal is a human. In certain embodiments, the vertebrate is a non-mammal such as birds, reptiles or amphibians. Hence, the subject or patient may include, but is not limited to, farm animals (such as cattle), laboratory animals (such as mice, rats, pigs, primates, guinea pigs, rabbits, etc), sport animals, domestic animals or pets (such as cats, dogs, and horses). In certain embodiments, the subject or patient is human. In some embodiments, the mammal comprises primates, dogs, horses, cats, cattle, or pigs. In some embodiments, the subject comprises a non-human animal. In some embodiments, the non-human animal is a bird or a reptile. In some embodiments, the non-human animal is a chicken.

While the invention has been described with respect to specific examples, those skilled in the art will appreciate that there are numerous variations and permutations of the above described systems and techniques that fall within the spirit and scope of the invention as set forth in the appended claims.

WORKING EXAMPLES

Example 1: BioMAP® Systems

BioMAP® systems were used to predicts safety, efficacy and function of test agents in models of human tissue and disease biology of the vasculature, skin, lung, and inflammatory tissues.

BioMAP® panels consist of human primary cell-based systems designed to model different aspects of the human body in an in vitro format. BioMAP® systems are constructed with one or more primary cell types from healthy human donors, with stimuli (such as cytokines or growth factors) added to capture relevant signaling networks that naturally occur in human tissue or pathological conditions. Vascular biology is modeled in both a Th1 (3C system) and a Th2 (4H system) inflammatory environment, as well as in a Th1 inflammatory state specific to arterial smooth muscle cells (CASM3C system). Additional systems recapitulate aspects of the systemic immune response including monocyte-driven Th1 inflammation (LPS system) or T cell stimulation (SAg system), chronic Th1 inflammation driven by macrophage activation (Mphg system) and the T cell-dependent activation of B cells that occurs in germinal centers (BT system). The BE3C system (Th1) and the BF4T system (Th2) represent airway inflammation of the lung, while the MyoF system models myofibroblast-lung tissue remodeling. Lastly, skin biology is addressed in the KF3CT system modeling Th1 cutaneous inflammation and the HDF3CGF system modeling wound healing. A subset of 8 of these BioMAP systems has previously been used in the U.S. Environmental Protection Agency (EPA)'s ToxCast™ program to characterize environmental chemicals, define mechanisms of toxicity and to develop predictive signatures of toxicity.

The diseases and conditions modeled by the above cellular systems are shown in Table 1 below.

TABLE 1 overview of disease models

| System name | Modeled Diseases and conditions |
|---|---|
| 3C | Th1 type vascular inflammation diseases or conditions such as chronic inflammatory diseases, vascular inflammation, and restenosis. |
| 4H | Th2 type vascular inflammation diseases or conditions such as allergy, asthma and ulcerative colitis. |
| LPS | Diseases and conditions related to Th1 type chronic inflammation and monocyte activation responses such as atherosclerosis, restenosis, rheumatoid arthritis, and metabolic disease. |
| SAg | Diseases and conditions related to Th1 type chronic inflammation and T cell effector responses in the context of the vascular endothelium. In particular, inflammation driven conditions such as organ transplantation related responses, rheumatoid arthritis, psoriasis, Crohn's disease and hematological oncology. |
| BT | Diseases and conditions related to T cell dependent B cell proliferation, activation, and class switching in the germinal centers of secondary lymphoid organs, and related conditions such as systemic lupus erythematosus (SLE), hematological oncology, autoimmune indications, asthma and allergy. |
| BF4T | Th2 type lung inflammation such as asthma, pulmonary fibrosis, and Chronic Obstructive Pulmonary Disease (COPD) exacerbations. |
| BE3C | Th1 type lung inflammation such as sarcoidosis and pulmonary responses to respiratory infections. |
| CASM3C | Th1 type vascular inflammation such as chronic inflammatory diseases, vascular inflammation, and restenosis. |
| HDF3CGF | Th1 type inflammation such as fibrosis, rheumatoid arthritis, and psoriasis. HDF3CGF is also a model for stromal biology in tumors. |
| KF3CT | Th1 type cutaneous inflammation responses to mechanical, chemical, or infectious agents, and psoriasis and dermatitis. |
| MyoF | Multiple fibrosis diseases or inflammation related responses in fibrotic tissue. |

TABLE 1-continued

| overview of disease models | |
|---|---|
| System name | Modeled Diseases and conditions |
| /Mphg | Th1 type chronic inflammation and macrophage activation responses such as atherosclerosis, restenosis, rheumatoid arthritis, and other chronic inflammatory diseases. |

Table 2 provides further description of the above described markers and associated BioMAP® systems.

TABLE 2

Markers identified in BioMAP ® profile of the test agents.

| Marker | System name | Description/full name | Alternative name |
|---|---|---|---|
| Eotaxin 3 | 4H | chemokine | CCL26 |
| MCP-1 | 4H | chemoattractant | CCL2 |
| MIP-1α | | Macrophage Inflammatory Proteins (MIP) | |
| I-TAC | BE3C | Interferon-inducible T call alpha chemoattractant | CXCL11 |
| VCAM-1 | /Mphg | Vascular Cell Adhesion Molecule 1 | CD106 |
| SAA | CASM3C | Serum Amyloid A | |
| MIG | 3C | Monokine induced by gamma interferon | CXCL9 |
| IP-10 | KF3CT | Interferon gamma inducible protein 10 | CXCL10 |
| IL-6 | CASM3C | Interleukin-6 | |
| IL-lα | BE3C | Interleukin-1 alpha | |
| P-selectin | 4H | Cell-adhesion molecule | CD62P |
| sPGE2 | LPS | Prostaglandin E2 | |
| STNFα | LPS | Tumor necrosis factor alpha | |
| IL-8 | LPS | Interleukin-8 | CXCL8 |
| CD40 | LPS | Cell surface adhesion molecule | |
| SIL-10 | /Mphg | Interleukin-10 | |
| slgG | BT | Secreted immunoglobulin G | |
| HLA-DR | CASM3C | Cell surface heterodimer involved in antigen presentation | |
| SIL-17A | BT | Interleukin 17A | |
| CD38 | SAg | T cell activation marker | |
| SIL-17F | BT | Interleukin 17F | |
| SIL-2 | BT | Interleukin 2 | |
| CD69 | SAg | Cell surface activation antigen | |
| TIMP-1 | HDF3CGF | Tissue inhibitor of matrix metallprotease-7 | |
| Collagen I | HDF3CGF/ MyoF | Fibrillar collagen of skin, bone, tendons and other connective tissue. | |
| Collagen IV | MyoF | Major structural component of basal lamina. | |
| Collagen III | HDF3CGF/ MyoF | Extensible collage in skin, lung, and vascular system. | |
| MMP-1 | MyoF/BE3C | Matrix-metalloproteinase 1 | |
| PAI-1 | MyoF | Plasminogen activator inhibitor-1 | |
| uPAR | 3C | Urokinase plasminogen activator receptor | CD87 |
| αSMA | MyoF | Alpha-smooth muscle actin | |
| bFGF | MyoF | Basic fibroblast growth factor | |
| Ker8/18 | BF4T/BE3C | Keratin 8/18 | |
| MMP-9 | BF4T/BE3C | Matrix-metalloproteinase 9 | |
| TM | LPS | TM is thrombomodulin | |
| TF | LPS | TF is Tissue Factor | |
| LDLR | BE3C | low-density lipoprotein receptor | |

Each test agent generates a signature BioMAP® profile that is created from the changes in protein biomarker readouts within individual system environments. Biomarker readouts (7-17 per system) are selected for therapeutic and biological relevance, are predictive for disease outcomes or specific drug effects and are validated using agents with known mechanism of action (MoA). Each readout is measured quantitatively by immune-based methods that detect protein (e.g., ELISA) or functional assays that measure proliferation and viability. BioMAP® readouts are diverse and include cell surface receptors, cytokines, chemokines, matrix molecules and enzymes. In total, the Diversity PLUS panel contains 148 biomarker readouts that capture biological changes that occur within the physiological context of the particular BioMAP® system.

Using custom-designed software containing data mining tools, a BioMAP® profile can be compared against a proprietary reference database of >4,000 BioMAP® profiles of bioactive agents (biologics, approved drugs, chemicals and experimental agents) to classify and identify the most similar profiles. This robust data platform allows rapid evaluation and interpretation of BioMAP® profiles by performing the unbiased mathematical identification of similar activities. Specific BioMAP® activities have been correlated to in vivo biology, and multiparameter BioMAP® profiles have been used to distinguish compounds based on MoA and target selectivity and can provide a predictive signature for in vivo toxicological outcomes (e.g., vascular toxicity, developmental toxicity, etc.) across diverse physiological systems.

Human primary cells in BioMAP® systems are used at early passage (passage 4 or earlier) to minimize adaptation to cell culture conditions and preserve physiological signaling responses. All cells are from a pool of multiple donors (n=2-6), commercially purchased and handled according to the recommendations of the manufacturers. Human blood derived CD14+ monocytes are differentiated into macrophages in vitro before being added to the Mphg system. Abbreviations are used as follows: Human umbilical vein endothelial cells (HUVEC), Peripheral blood mononuclear cells (PBMC), Human neonatal dermal fibroblasts (HDFn), B cell receptor (BCR), T cell receptor (TCR) and Toll-like receptor (TLR). Cell types and stimuli used in each system are as follows: 3C system [HUVEC+(IL-1β, TNFα and IFNγ)], 4H system [HUVEC+(IL-4 and histamine)], LPS system [PBMC and HUVEC+LPS (TLR4 ligand)], SAg system [PBMC and HUVEC+TCR ligands], BT system [CD19+B cells and PBMC+(α-IgM and TCR ligands)], BF4T system [bronchial epithelial cells and HDFn+(TNFα and IL-4)], BE3C system [bronchial epithelial cells+(IL-1β, TNFα and IFNγ)], CASM3C system [coronary artery smooth muscle cells+(IL-1β, TNFα and IFNγ)], HDF3CGF system [HDFn+(IL-1β, TNFα, IFNγ, EGF, bFGF and PDGF-BB)], KF3CT system [keratinocytes and HDFn+(IL-1β, TNFα, IFNγ and TGFβ)], MyoF system [differentiated lung myofibroblasts+(TNFα and TGFβ)] and 1 Mphg system [HUVEC and M1 macrophages+Zymosan (TLR2 ligand)]. Systems are derived from either single cell types or co-culture systems. Adherent cell types are cultured in 96 or 384-well plates until confluence, followed by the addition of PBMC (Sag and LPS systems). The BT system consists of $CD19^+$ B cells co-cultured with PBMC and stimulated with a BCR activator and low levels of TCR stimulation. Test agents prepared in either DMSO (small molecules; final concentration≤0.1%) or PBS (biologics) are added at the indicated concentrations 1-hr before stimulation, and remain in culture for 24-hrs or as otherwise indicated (48-hrs, MyoF system; 72-hrs, BT system (soluble readouts); 168-hrs, BT system (secreted IgG)). Each plate contains drug controls (e.g., legacy control test agent colchicine at 1.1 μM), negative controls (e.g., non-stimulated conditions) and vehicle controls (e.g., 0.1% DMSO) appropriate for each system. Direct ELISA is used to measure biomarker levels of cell-associated and cell membrane targets. Soluble factors from supernatants are quantified using either HTRF® detection, bead-based multiplex immunoassay or capture ELISA. Overt adverse effects of test agents on cell proliferation and viability (cytotoxicity) are detected by sulforhodamine B (SRB) staining, for adherent cells, and alamarBlue® reduction for cells in suspension. For proliferation assays, individual cell types are cultured at subconfluence and measured at time points optimized for each system (48-hrs: 3C and CASM3C systems; 72-hrs: BT and HDF3CGF systems; 96-hrs: SAg system). Cytotoxicity for adherent cells is measured by SRB (24-hrs: 3C, 4H, LPS, SAg, BF4T, BE3C, CASM3C, HDF3CGF, KF3CT, and/Mphg systems; 48-hrs: MyoF system), and by alamarBlue staining for cells in suspension (24-hrs: SAg system; 42-hrs: BT system) at the time points indicated.

Data Analysis is performed by dividing the measurements of the test agent by the average of control samples (at least 6 vehicle controls from the same plate) to generate a ratio that is then $\log_{10}$ transformed. Significance prediction envelopes are calculated using historical vehicle control data at a 95% confidence interval.

Biomarker activities are annotated when 2 or more consecutive concentrations change in the same direction relative to vehicle controls, are outside of the significance envelope and have at least one concentration with an effect size>20% ($|\log_{10}$ ratio$|>0.1$). Biomarker key activities are described as modulated if these activities increase in some systems, but decrease in others. Cytotoxic conditions are noted when total protein levels decrease by more than 50% ($\log_{10}$ ratio of SRB or alamarBlue levels<−0.3) and are indicated by a thin black arrow above the X-axis. A compound is considered to have broad cytotoxicity when cytotoxicity is detected in 3 or more systems. Concentrations of test agents with detectable broad cytotoxicity are excluded from biomarker activity annotation and downstream benchmarking, similarity search and cluster analysis. Antiproliferative effects are defined by an SRB or alamarBlue® $\log_{10}$ ratio value<−0.1 from cells plated at a lower density and are indicated by grey arrows above the X-axis. Cytotoxicity and antiproliferative arrows only require one concentration to meet the indicated threshold for profile annotation.

Example 2: Analysis of Test Agent 2: 2,4,6-tris(3,4-dihydro-2H-pyrrol-2-yl)pyridine A BioMAP® profile was generated for 2,4,6-tris(3,4-dihydro-2H-pyrrol-2-yl)pyridine as described in Example 1.

2,4,6-tris(3,4-dihydro-2H-pyrrol-2-yl)pyridine was found to be not cytotoxic at the concentrations tested in this study. 2,4,6-tris(3,4-dihydro-2H-pyrrol-2-yl)pyridine was found to be antiproliferative to human primary endothelial cells (100 μM, 33 μM, 11 μM), T cells (100 μM, 33 μM), B cells (100 μM, 33 μM, 11 μM), and fibroblasts (100 μM).

2,4,6-tris(3,4-dihydro-2H-pyrrol-2-yl)pyridine was found to impact inflammation-related activities as demonstrated by decreased Eotaxin 3, MCP-1, VCAM-1, SAA, I-TAC, MIG, IL-6, and P-selectin; increased sPGE2; and modulated sTNFα, IL-8. 2,4,6-tris(3,4-dihydro-2H-pyrrol-2-yl)pyridine was found to impact immunomodulatory activities as demonstrated by decreased CD40, sIgG, sIL-10, HLA-DR, sIL-17A, CD38, sIL-6, sIL-17F, and sIL-2; and increased CD69. 2,4,6-tris(3,4-dihydro-2H-pyrrol-2-yl)pyridine was found to impact tissue remodeling activities as demonstrated by decreased TIMP-1, Collagen IV, PAI-1, and Collagen III. 2,4,6-tris(3,4-dihydro-2H-pyrrol-2-yl)pyridine was found to impact hemostasis-related activities as demonstrated by decreased TM; and increased TF. In addition, 2,4,6-tris(3,4-dihydro-2H-pyrrol-2-yl)pyridine was found to decrease LDLR.

See Table 2 for further description of these markers and associated BioMAP® systems.

Example 3: Analysis of Test Agent 3: 2,4,6-tris(3,4-dihydro-2H-pyrrol-2-yl)pyridine with Ethanol as Carrier A BioMAP® profile was generated for 2,4,6-tris(3,4-dihydro-2H-pyrrol-2-yl)pyridine with ethanol as carrier as described in Example 1.

2,4,6-tris(3,4-dihydro-2H-pyrrol-2-yl)pyridine with ethanol as carrier was found to not be cytotoxic at the concentrations tested in this study.

2,4,6-tris(3,4-dihydro-2H-pyrrol-2-yl)pyridine with ethanol as carrier was found to be antiproliferative to human primary B cells (200 μM, 67 μM, 22 μM, 7.4 μM), T cells (200 μM, 67 μM, 22 μM, 7.4 μM), endothelial cells (200 μM, 67 μM, 22 μM, 7.4 μM), and fibroblasts (22 μM, 7.4 μM).

2,4,6-tris(3,4-dihydro-2H-pyrrol-2-yl)pyridine with ethanol as carrier was found to impact inflammation-related activities as demonstrated by decreased Eotaxin 3, MCP-1, MIP-1α, I-TAC, MIG, IP-10, IL-6, VCAM-1, SAA, IL-1α, and P-selectin; increased sPGE2; modulated IL-8, and sTNFα. 2,4,6-tris(3,4-dihydro-2H-pyrrol-2-yl)pyridine with ethanol as carrier was found to impact immunomodulatory activities as demonstrated by decreased CD40, sIgG, sIL-17A, sIL-6, sIL-17F, sIL-2, sIL-10, HLA-DR, and CD38; and increased CD69. 2,4,6-tris(3,4-dihydro-2H-pyrrol-2-yl)pyridine with ethanol as carrier was found to impact tissue remodeling activities as demonstrated by decreased Collagen I, TIMP-2, TIMP-1, Collagen IV, tPA, Collagen III, αSMA, bFGF, MMP-1, PAI-1, Ker8/18, and MMP-9; and increased uPAR. 2,4,6-tris(3,4-dihydro-2H-pyrrol-2-yl)pyridine with ethanol as carrier was found to impact hemostasis-related activities as demonstrated by decreased TM; and increased TF. 2,4,6-tris(3,4-dihydro-2H-pyrrol-2-yl)pyridine with ethanol as carrier was found to decrease VEGFR2.

See Table 2 for further description of these markers and associated BioMAP® systems.

Example 4: Synthesis of 2,4,6-tris(3,4-dihydro-2H-pyrrol-2-yl)pyridine
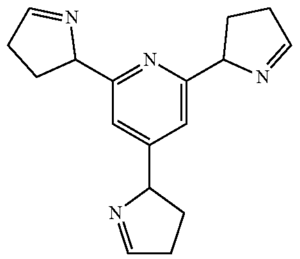 [SMILES: C1=NC(c2cc(C3CCC=N3)nc(C3CCC=N3)c2)CC1]
The synthesis of 2,4,6-tris(3,4-dihydro-2H-pyrrol-2-yl) pyridine was performed according to the following synthetic scheme I:
Synthesis Scheme I
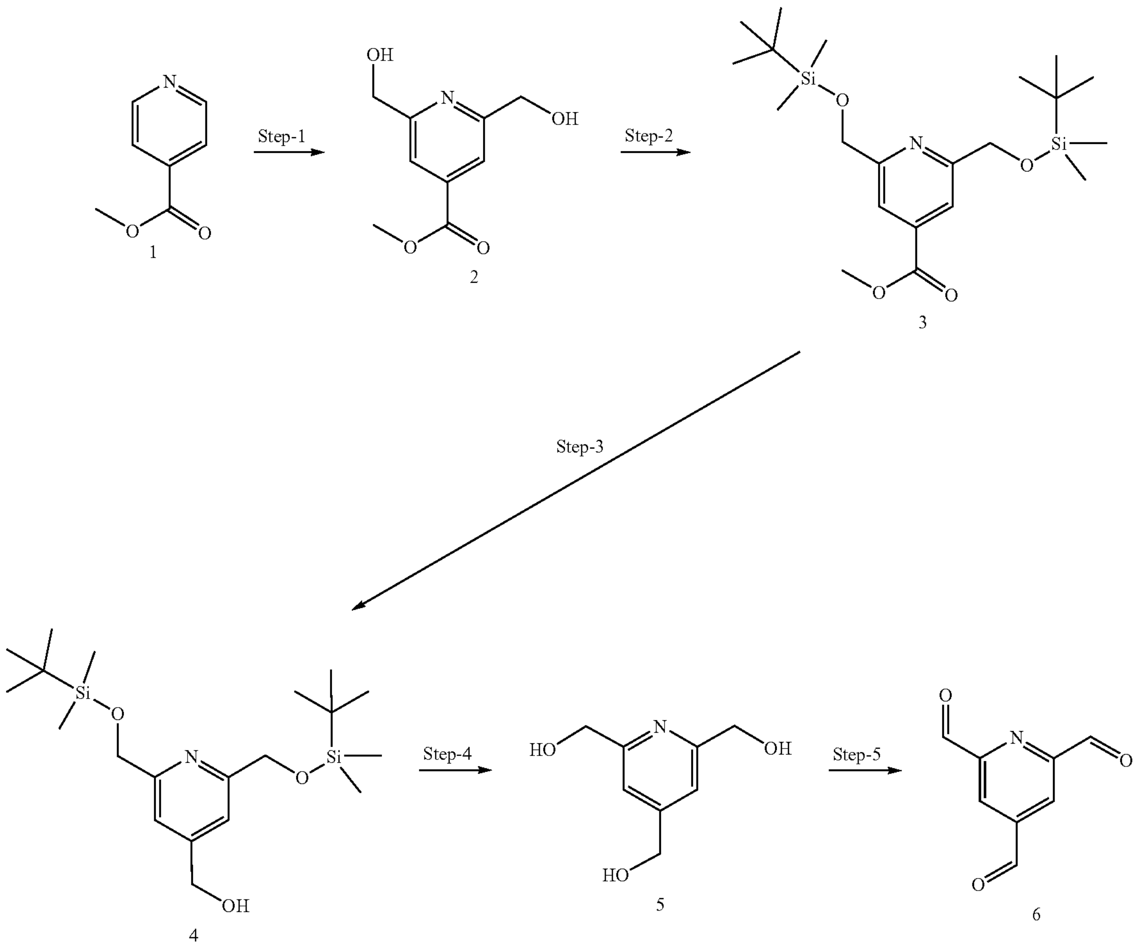

-continued

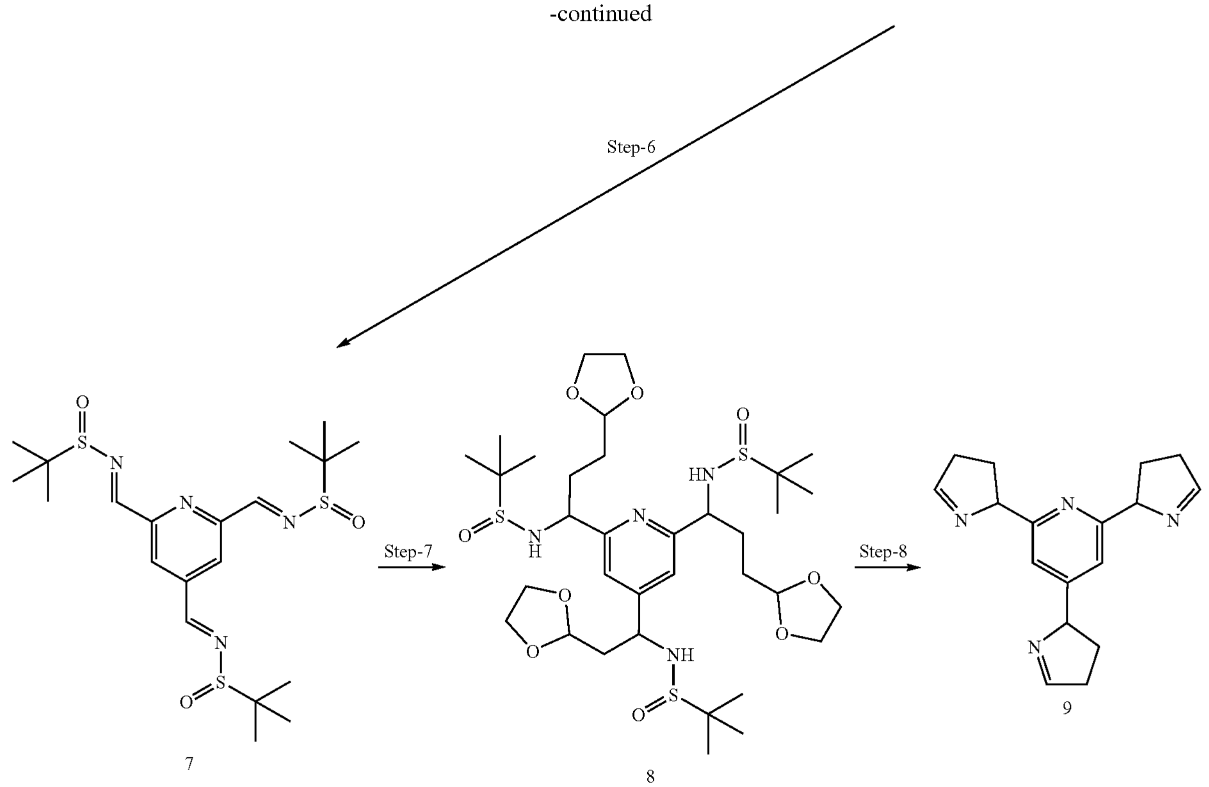

7 8 9

Step 3 in the above synthesis scheme I was performed by using sodium borohydride (NaBH4 (10.0 eq) and Methanol at 0° to room temperature (RT) for about 16 hours. The resulting compound 4 was isolated by using silica gel column chromatography. The yield was about 95%, resulting in 34 g of compound 4 from 38 g of compound 3. Formation of compound 4 was matched with authentic.

Step 4 in synthesis scheme I was performed by using 6N hydrogen chloride (HCl) at 0° to RT, and compound 5 was isolated by using silica gel column chromatography. The yield of this reaction was about 66%, resulting in 9.6 g of compound 5. Formation of compound 5 was matched with authentic.

Step 5 in synthesis scheme I was performed by using Dess-Martin periodinane (4.5 eq) and dichloromethane (DCM) at RT for 16 hours. This reaction yielded 8.4 g of crude compound 6, which was not purified before next step. Formation of compound 6 was matched with authentic.

Step 6 in synthesis scheme I was performed by using (S)-(−)-2-Methyl-2-propanesulfinamide (3.2 eq), para-Toluene Sulfonic Acid (PTSA) (0.3 eq). This reaction yielded 95% or 24 g. Compound 7 was matched with authentic and isolated by using silica gel column chromatography.

Step 7 in synthesis scheme I was performed by using 2-(2-Bromoethyl)-1,3-dioxolane (10 eq), magnesium (Mg) (13 eq), Iodine (catalytic), and tetrahydrofuran (THF) (50 V) at −20° C. for 2 hours. Next, the reaction was continued with THF (10V) at 0° for 16 hours. The yield was 37% and resulted in 15 g of compound 8. Formation of compound 8 was confirmed by LCMS and HNMR. Compound 8 was isolated by using silica gel column chromatography followed by reverse phase column chromatography in 15 g scale with 99% (20.7%+78.3%) LCMS purity. The splitting observed in LC is likely due to isomer formation.

Step 8 in synthesis scheme I was performed by using 10% $H_2SO_4$ (10 V), and DCM (5 V) at 0-5° C. for 6 hours. The yield was 92%, resulting in 7.0 g of compound 9. Formation of compound 9 was confirmed by LCMS and NMR. Compound 9 was isolated in 7 g scale with 95.6% (59.4%+36.2%) HPLC purity. Compound 9 was confirmed to be 2,4,6-tris(3,4-dihydro-2H-pyrrol-2-yl)pyridine. Physical characteristics of compound 9 includes pale brown color, low melting point, and foamy solid.

Example 5: Synthesis of 2,4,6-tris(3,4-dihydro-2H-pyrrol-2-yl)pyridine

The synthesis of 2,4,6-tris(3,4-dihydro-2H-pyrrol-2-yl)pyridine was performed according to the following synthesis scheme II:

Synthesis scheme II

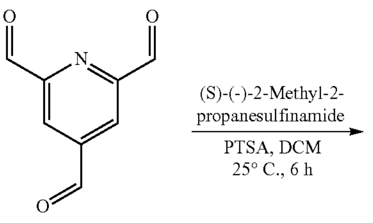

6

-continued

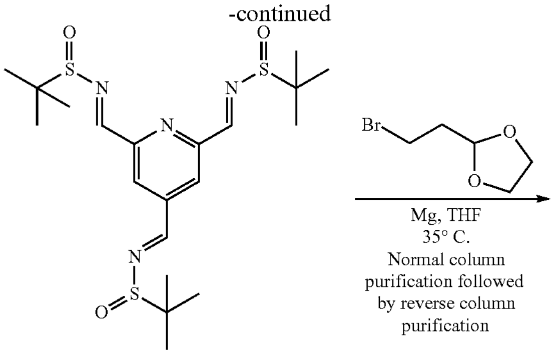

7

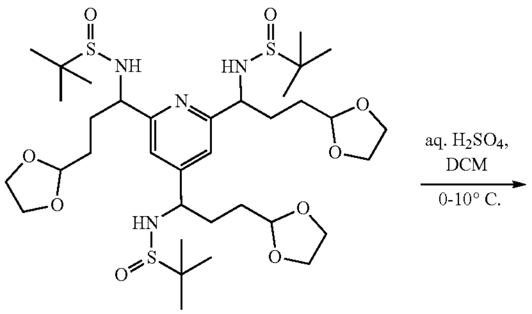

8

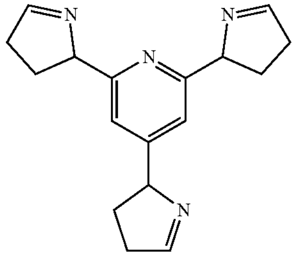

Trisomine
(9)

Steps 1-5 in synthesis scheme II were performed as in Example 4 to generate Compound 6.

Compound 6 in synthesis scheme II was reacted with (S)-(−)-2-Methyl-2-propanesulfinamide, para-Toluene Sulfonic Acid (PTSA), and dichloromethane (DCM) at 25° C. for 6 hours to generated compound 7.

Next, according to synthesis scheme II, compound 7 was reacted with 2-(2-Bromoethyl)-1,3-dioxolane, magnesium (Mg), and tetrahydrofuran (THF) at 35° C., followed by normal column purification and then reverse column purification to generate compound 8.

HPLC (high performance liquid chromatography) purification of compound 8 resulted in a major peak (500 mg, 71% purity) and a minor peak (500 mg, 81% purity). Both purified peaks were used for the final reaction separately.

Finally, according to synthesis scheme II, compound 8 (both peaks) was subjected to $H_2SO_4$ and DCM at 0-10° C. to yield 2,4,6-tris(3,4-dihydro-2H-pyrrol-2-yl)pyridine (Trisomine).

1H NMR (proton nuclear magnetic resonance) was used to determine the structure and purity of the synthesized of 2,4,6-tris(3,4-dihydro-2H-pyrrol-2-yl)pyridine. Overlay of 1H NMR spectra for different lots of 2,4,6-tris(3,4-dihydro-2H-pyrrol-2-yl)pyridine produced according the above synthesis are shown in FIGS. 1 to 4, which shows consistent synthesis of the Trisomine.

Figure 9:
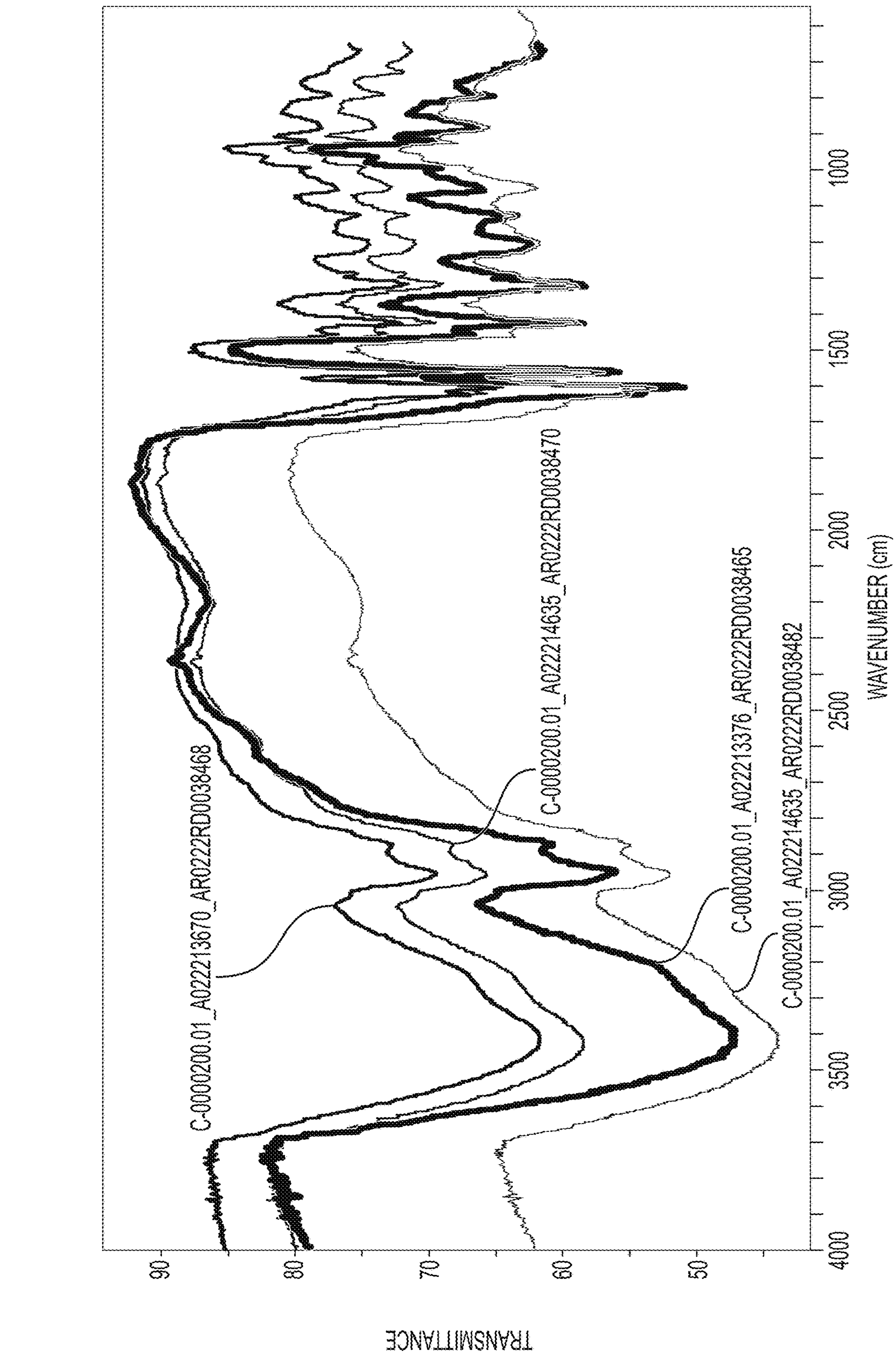
FIG. 9 shows an overlay of the IR spectra shown in FIGS. 5-8.

Infrared (IR) spectroscopy was also used to confirm the identity of the synthesized of 2,4,6-tris(3,4-dihydro-2H-pyrrol-2-yl)pyridine. FIGS. 5-8 show IR spectrum for different lots of synthesized of 2,4,6-tris(3,4-dihydro-2H-pyrrol-2-yl)pyridine, and FIG. 9 shows the overlay of these spectra. The overlay in FIG. 9 shows that the IR spectrum is similar for all the lots.

Figure 10:
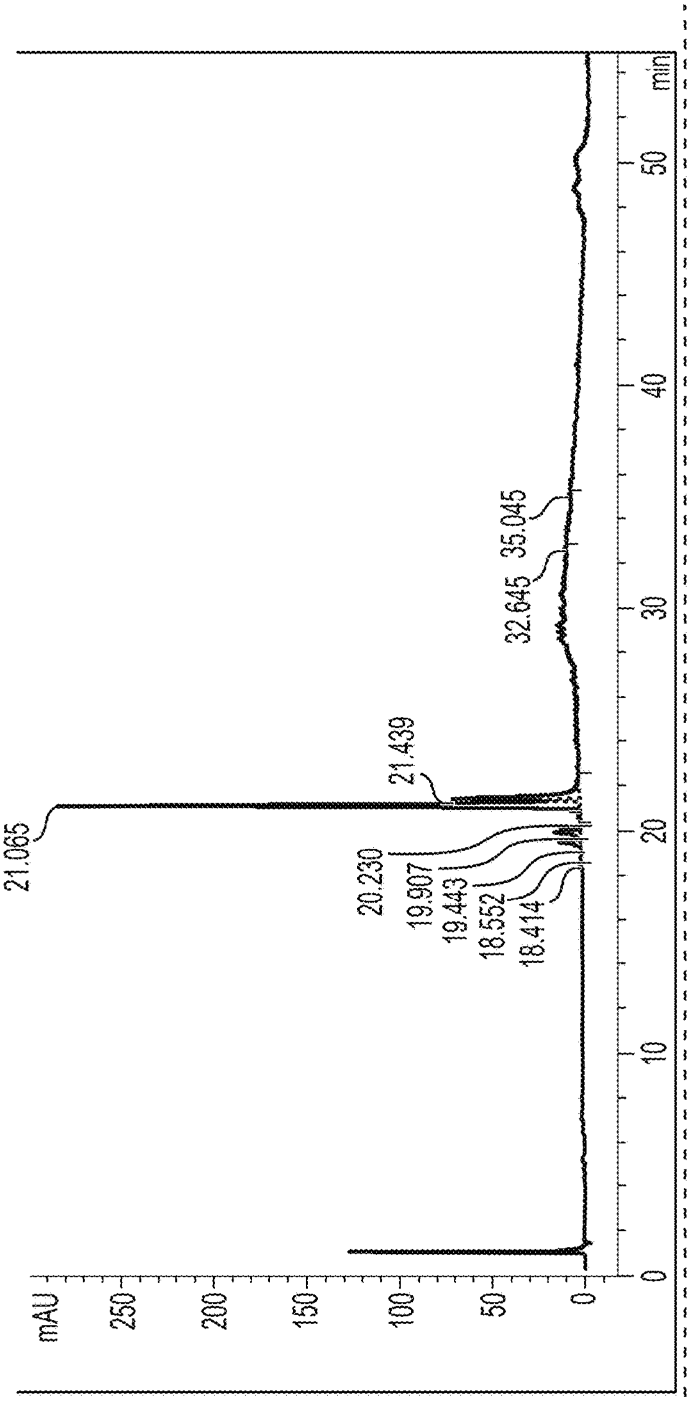
FIG. 10 shows the results of long run liquid chromatography mass spectrometry (LC-MS) analysis of the 2,4,6-Tri(3,4-dihydro-2H-pyrrol-2-yl)pyridine synthesized according to protocol set forth in Example 5 herein. The results LC-MS further confirmed that both the major and minor peaks from the HPLC of compound 8 produced 2,4,6-Tri(3,4-dihydro-2H-pyrrol-2-yl)pyridine.
Figure 11:
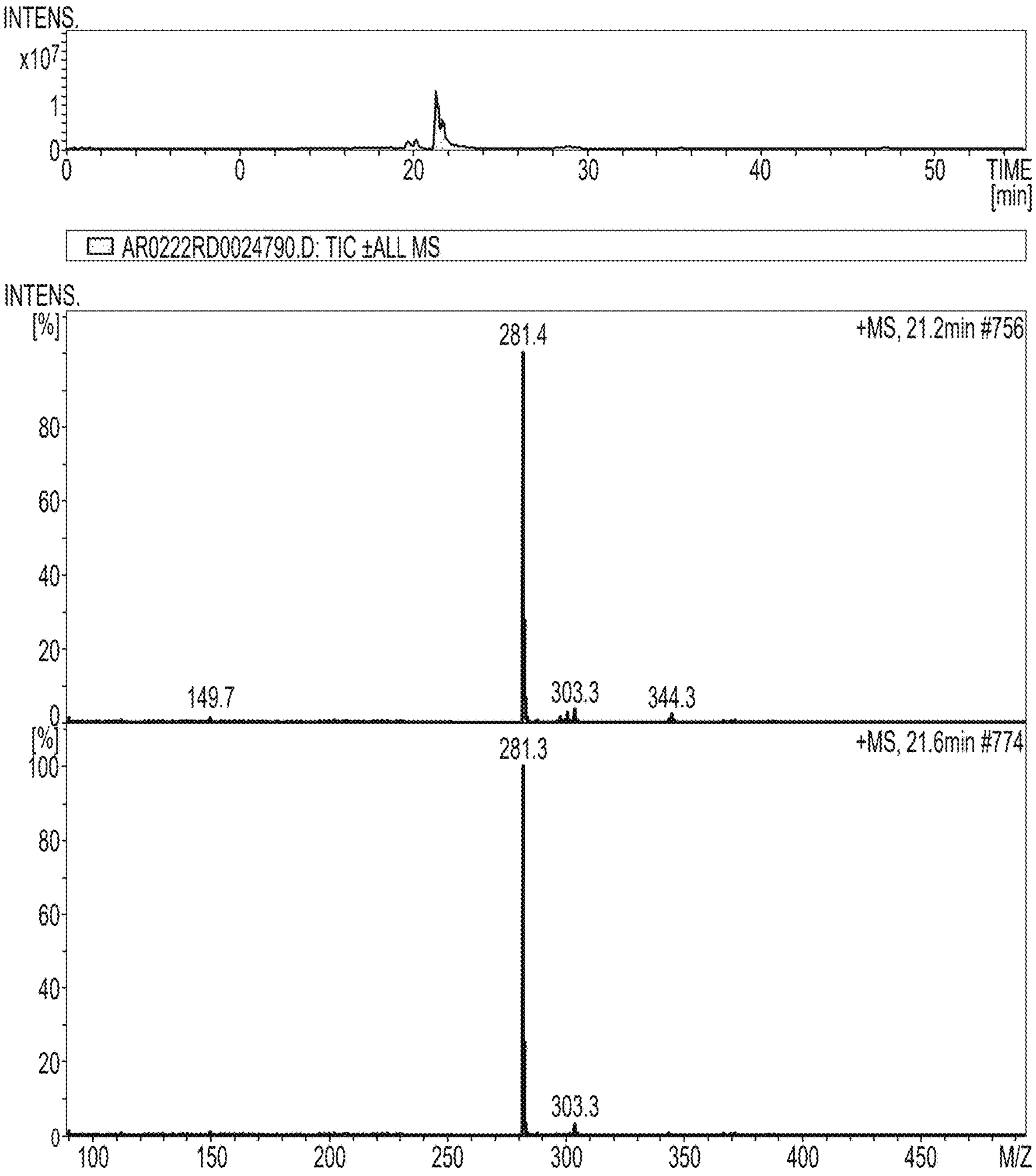
FIG. 11 shows the results of long run liquid chromatography mass spectrometry analysis of the 2,4,6-Tri(3,4-dihydro-2H-pyrrol-2-yl)pyridine synthesized according to protocol set forth in Example 5 herein. The [M+H]+ from LCMS analysis for both the peaks from the HPLC purification corresponds to the product mass [LC-MS calc. for C17H21N4 [M+H]+ m/z:281.3, found: 281.3].

Long run liquid chromatograph mass spectrometry (LC-MS) was carried out to confirm that both peaks from the HPLC correspond to 2,4,6-tris(3,4-dihydro-2H-pyrrol-2-yl) pyridine as shown in FIGS. 10 and 11.

Figure 12:
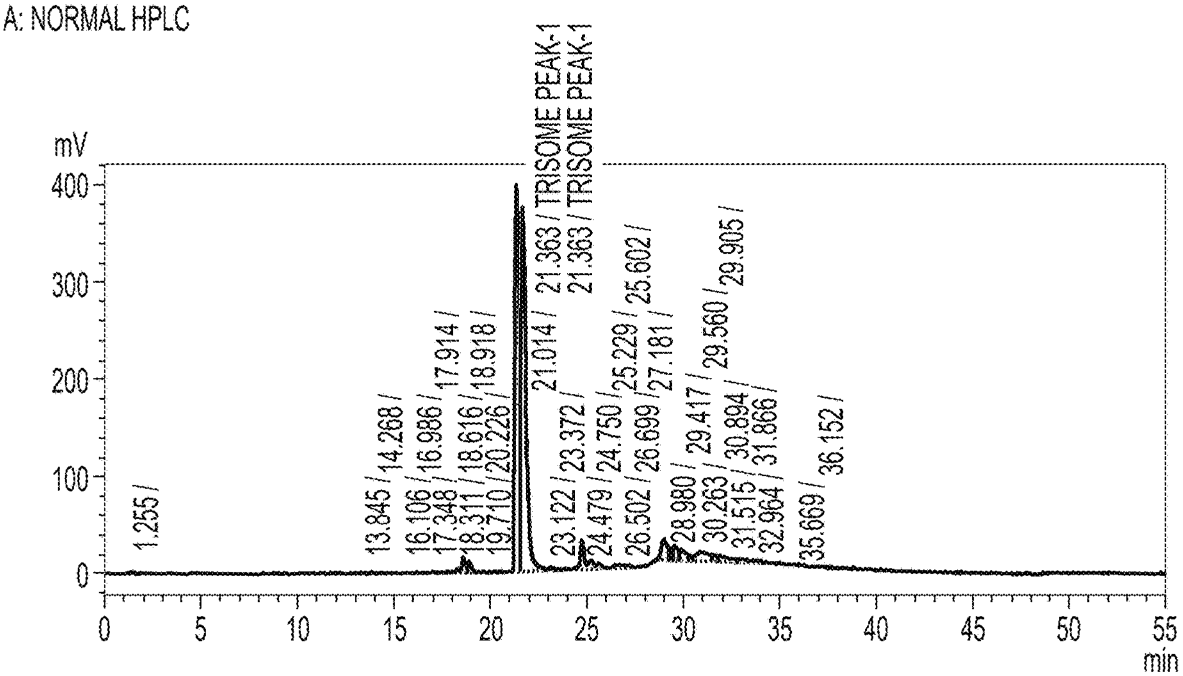
FIG. 12 shows normal HPLC (A) and chiral HPLC (B) of the same lot of synthesized 2,4,6-Tri(3,4-dihydro-2H-pyrrol-2-yl)pyridine.
Figure 12:
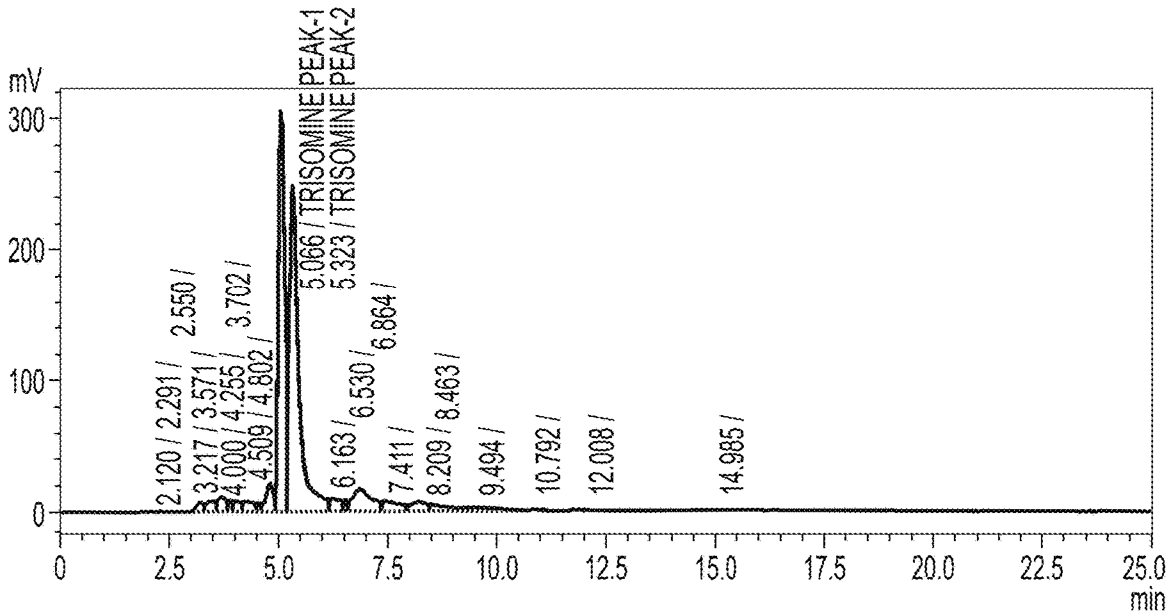

Chiral HPLC was also performed, which observed two peaks similar to the regular HPLC as illustrated by one lot of the synthesized 2,4,6-tris(3,4-dihydro-2H-pyrrol-2-yl) pyridine in FIG. 12. The peak tables below shows the data plotted in FIG. 12.

TABLE 3

Peak table showing data for regular HPLC corresponding to FIG. 12 (A).
Peak Table
Detector A Channel 1 260 nm

| Peak # | Ret. Time (min) | RRT | Height | Area | Area % | Name |
|---|---|---|---|---|---|---|
| 1 | 1.225 | 0.057 | 1165 | 3959 | 0.025 | |
| 2 | 13.845 | 0.648 | 1231 | 16784 | 0.106 | |
| 3 | 14.268 | 0.668 | 628 | 7669 | 0.048 | |
| 4 | 16.106 | 0.754 | 1153 | 12970 | 0.082 | |
| 5 | 16.986 | 0.795 | 1301 | 16372 | 0.103 | |
| 6 | 17.348 | 0.812 | 969 | 21197 | 0.134 | |
| 7 | 17.914 | 0.839 | 1474 | 34544 | 0.218 | |
| 8 | 18.311 | 0.857 | 3719 | 44875 | 0.283 | |
| 9 | 18.616 | 0.871 | 15139 | 197698 | 1.248 | |
| 10 | 18.918 | 0.886 | 10745 | 153977 | 0.972 | |
| 11 | 19.710 | 0.923 | 778 | 11576 | 0.073 | |
| 12 | 20.226 | 0.947 | 1238 | 18071 | 0.114 | |
| 13 | 21.014 | 0.984 | 756 | 16257 | 0.103 | |
| 14 | 21.362 | 1.000 | 397496 | 5637578 | 35.589 | trisomine peak-1 |
| 15 | 21.678 | 1.015 | 374295 | 6457444 | 40.765 | trisomine peak-2 |
| 16 | 23.122 | 1.082 | 2543 | 47237 | 0.298 | |
| 17 | 23.372 | 1.094 | 1590 | 20735 | 0.131 | |
| 18 | 24.479 | 1.146 | 1398 | 16145 | 0.102 | |
| 19 | 24.750 | 1.159 | 29970 | 374038 | 2.361 | |
| 20 | 25.229 | 1.181 | 8506 | 163607 | 1.033 | |
| 21 | 25.602 | 1.198 | 5218 | 98248 | 0.620 | |
| 22 | 26.502 | 1.241 | 2708 | 51930 | 0.328 | |
| 23 | 26.699 | 1.250 | 2967 | 64346 | 0.406 | |
| 24 | 27.181 | 1.272 | 2466 | 41301 | 0.261 | |
| 25 | 28.980 | 1.357 | 20968 | 494030 | 3.119 | |
| 26 | 29.417 | 1.377 | 12674 | 118804 | 0.750 | |
| 27 | 29.560 | 1.384 | 15148 | 249312 | 1.574 | |
| 28 | 29.905 | 1.400 | 10777 | 258200 | 1.630 | |
| 29 | 30.263 | 1.417 | 6082 | 58334 | 0.368 | |
| 30 | 30.894 | 1.446 | 9532 | 459729 | 2.902 | |
| 31 | 31.515 | 1.475 | 6893 | 125527 | 0.792 | |
| 32 | 31.866 | 1.492 | 6626 | 251969 | 1.591 | |
| 33 | 32.964 | 1.543 | 2792 | 249870 | 1.577 | |
| 34 | 35.663 | 1.669 | 1147 | 21747 | 0.137 | |
| 35 | 36.152 | 1.692 | 1193 | 24519 | 0.155 | |
| Total | | | 963286 | 15840595 | 100.000 | |

TABLE 4

Peak table showing data for chiral HPLC corresponding to FIG. 12 (B).
Peak Table
Detector A Channel 1 260 nm

| Peak # | Ret. Time (min) | RRT | Height | Area | Area % | Name |
|---|---|---|---|---|---|---|
| 1 | 2.120 | 0.418 | 185 | 1088 | 0.012 | |
| 2 | 2.291 | 0.462 | 369 | 5157 | 0.055 | |
| 3 | 2.550 | 0.503 | 155 | 1406 | 0.015 | |
| 4 | 3.217 | 0.635 | 6713 | 83471 | 0.893 | |
| 5 | 3.571 | 0.705 | 8214 | 116629 | 1.248 | |
| 6 | 3.702 | 0.731 | 11005 | 153915 | 1.647 | |
| 7 | 3.854 | 0.761 | 8468 | 61790 | 0.661 | |
| 8 | 4.000 | 0.790 | 8059 | 92258 | 0.987 | |
| 9 | 4.255 | 0.840 | 7440 | 132353 | 1.416 | |
| 10 | 4.506 | 0.889 | 6171 | 45574 | 0.488 | |
| 11 | 4.802 | 0.948 | 21133 | 264873 | 2.834 | |
| 12 | 5.066 | 1.000 | 305107 | 3088191 | 33.036 | trisomine peak-1 |
| 13 | 5.323 | 1.051 | 247430 | 3644403 | 38.987 | trisomine peak-2 |
| 14 | 6.163 | 1.216 | 9119 | 165625 | 1.772 | |
| 15 | 6.530 | 1.289 | 8291 | 66190 | 0.708 | |
| 16 | 6.864 | 1.355 | 16886 | 516462 | 5.525 | |
| 17 | 7.411 | 1.463 | 7604 | 212732 | 2.276 | |
| 18 | 8.209 | 1.620 | 7092 | 184425 | 1.973 | |
| 19 | 8.463 | 1.670 | 5035 | 170960 | 1.829 | |
| 20 | 9.494 | 1.874 | 2221 | 147199 | 1.575 | |
| 21 | 10.792 | 2.130 | 1276 | 78914 | 0.844 | |
| 22 | 12.008 | 2.370 | 890 | 86140 | 0.921 | |
| 23 | 14.985 | 2.958 | 364 | 28071 | 0.300 | |
| Total | | | 689221 | 9347826 | 100.000 | |

Figure 13:
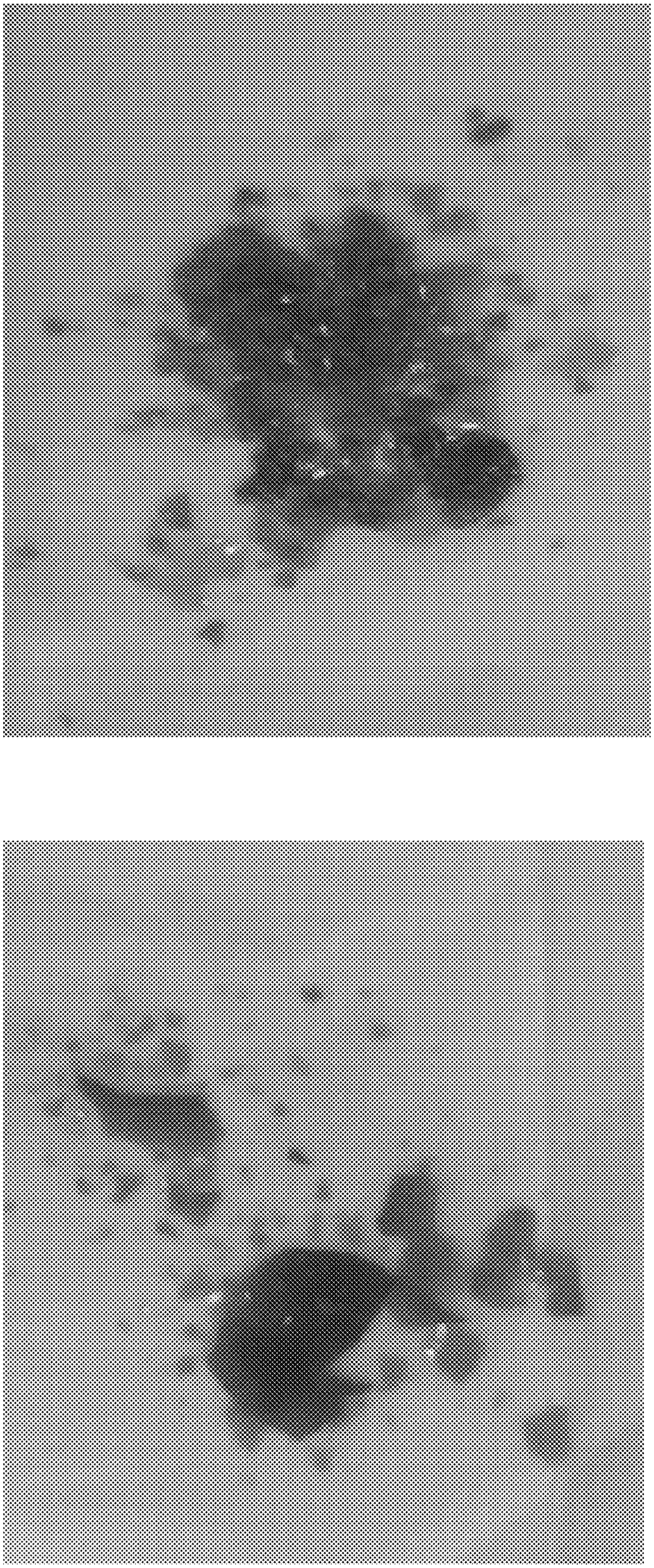
FIG. 13 shows pictures of crystals of synthesized 2,4,6-Tri(3,4-dihydro-2H-pyrrol-2-yl)pyridine from both HPLC peaks.

FIG. 13 shows an image of the resulting Trisomine obtained from peak 1 (or major peak) and peak 2 (or minor peak) isolated compound 8.

In summary, this example showed successful synthesis and purification of 2,4,6-tris(3,4-dihydro-2H-pyrrol-2-yl) pyridine.

Figure 14:
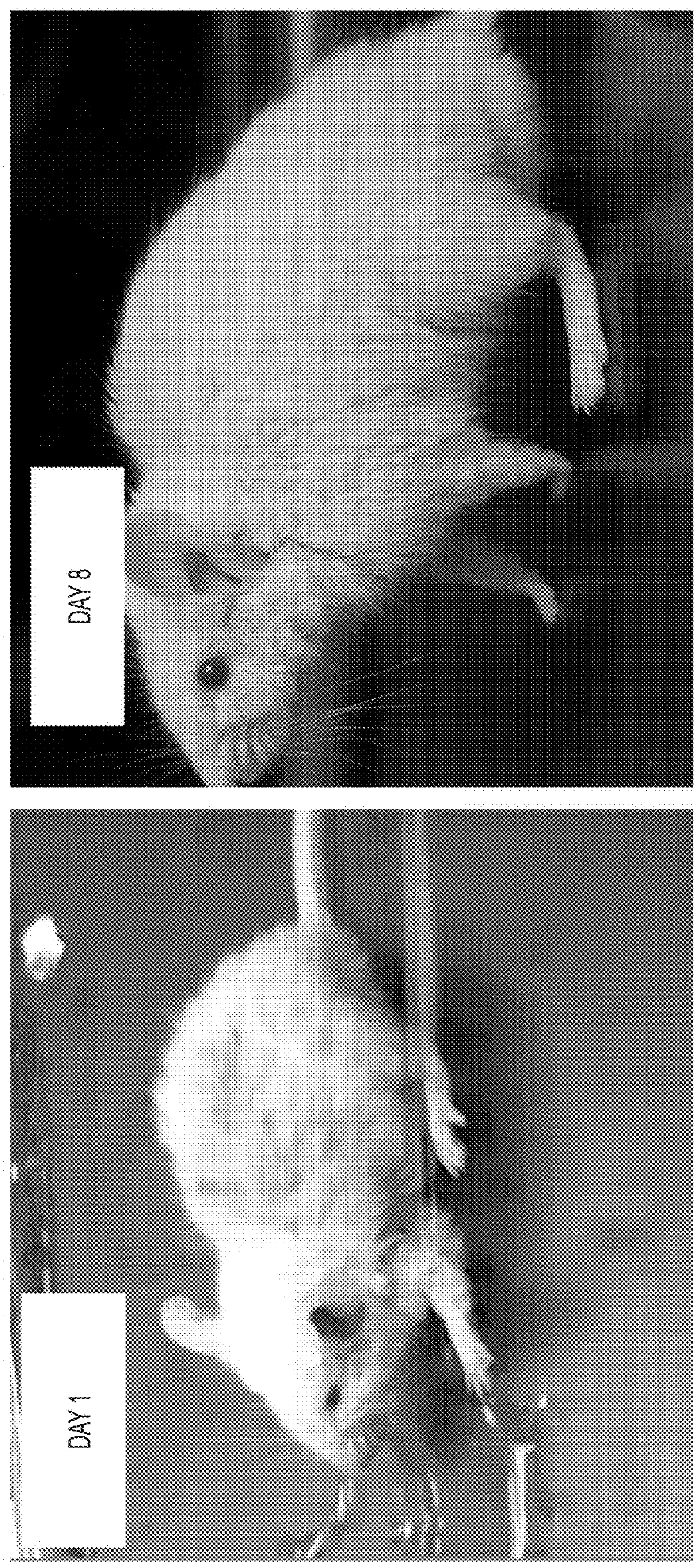
FIG. 14 shows picture of an old mouse treated with 10 mg/day 2,4,6-Tri(3,4-dihydro-2H-pyrrol-2-yl)pyridine at day 8 compared with day 1.

Example 6: Method of Treating, Reversing, Retarding or Preventing Aging Process of a Subject Example 6 showed reduced hair loss and increased vitality in aging mice. The method comprises administering a therapeutically effective amount of 2,4,6-tris(3,4-dihydro-2H-pyrrol-2-yl)pyridine to old mice. 12 month old mice were given 10 mg/day of 2,4,6-tris(3,4-dihydro-2H-pyrrol-2-yl)pyridine. The experiment was performed on 20 mice. At day 10, the mice's outward characteristics of aging (hair loss, low energy, low vitality) were reversed, such that the treated mice had full, thick hair, improved vitality, and were very energetic as evidence by FIG. 14.

Accordingly, this Example evidenced that 2,4,6-tris(3,4-dihydro-2H-pyrrol-2-yl)pyridine administration can treat, reverse, retard, or prevent the aging process of a subject.

Figure 15:
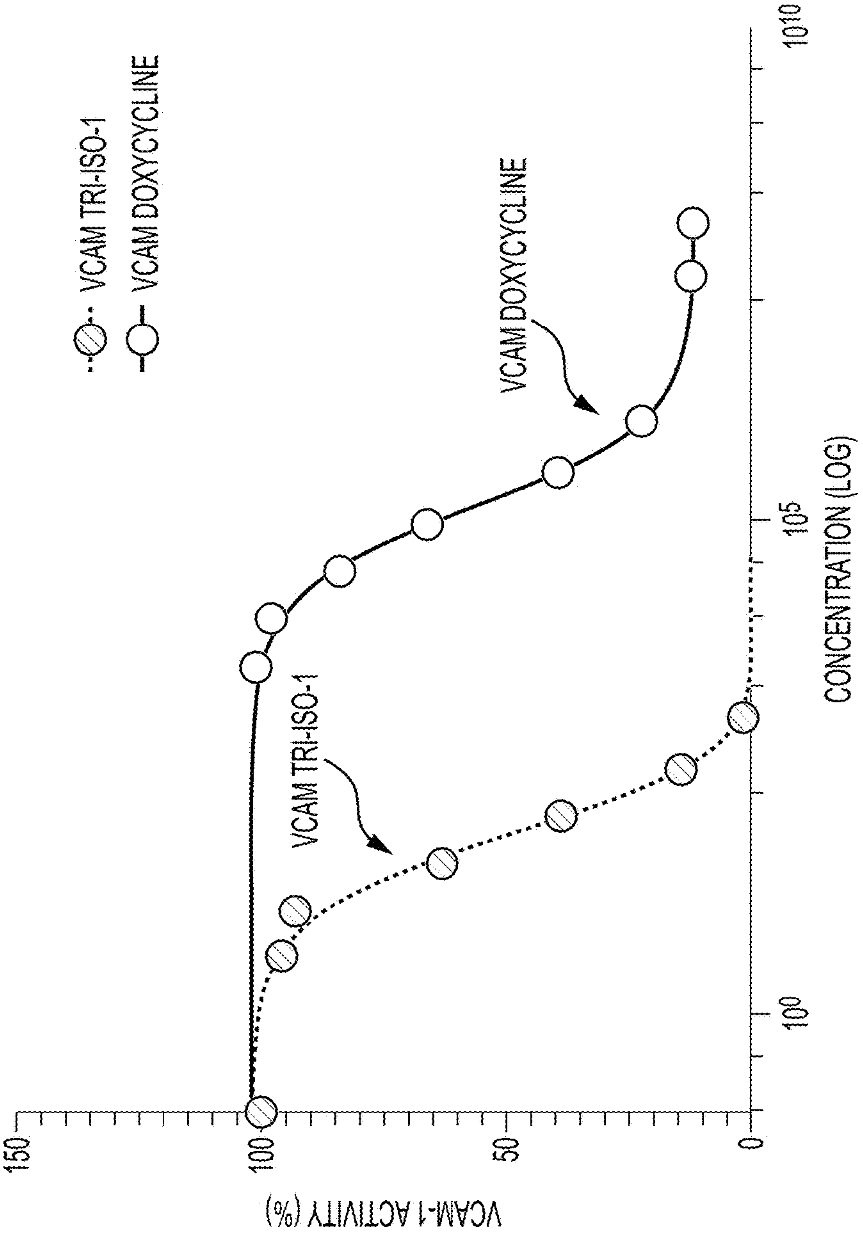
FIG. 15 shows inhibition of VCAM activity by 2,4,6-Tri(3,4-dihydro-2H-pyrrol-2-yl)pyridine (Tri-Iso-1) compared to doxycycline.

Example 7: 2,4,6-tris(3,4-dihydro-2H-pyrrol-2-yl)pyridine can Reduce VCAM-1 Levels 2,4,6-tris(3,4-dihydro-2H-pyrrol-2-yl)pyridine is 2000 times more potent at decreasing VCAM-1 levels than doxycycline as shown in FIG. 15. VCAM-1 is a key cell adhesion molecule involved in inflammation that is closely implicated in various immunological disorders (including rheumatoid arthritis and asthma), aging and cancer. Doxycycline is an antibiotic that also has anti-inflammatory effects, leading to its FDA approval for periodontal inflammation and the inflammatory skin condition called rosacea.

This example evidenced that 2,4,6-tris(3,4-dihydro-2H-pyrrol-2-yl)pyridine is an effective anti-inflammation agent and can treat immunological disorders (including rheumatoid arthritis and asthma), aging and cancer.

Example 8: Synthesis of 2,4,6-tris(3,4-dihydro-2H-pyrrol-2-yl)pyridine

This example provides an exemplary scheme for synthesizing 2,4,6-Tri(3,4-dihydro-2H-pyrrol-2-yl)pyridine/Trisomine.

In this example, Trisomine was synthesized in a four steps synthetic protocol shown in synthetic scheme III below. Trimethyl pyridine oxidized with $SeO_2$ to get 2,4,6-pyridine tricarbaldehyde intermediate. 2,4,6-Pyridine tricarbaldehyde was then treated with S-(−)-2-methyl-2-propanesulfinamide to get an Stage 1 product. Grignard reaction was performed with the Stage 1 and 2-(2-bromoethyl)-1,3-dioxolane to get Stage 2 product. Stage 2 was treated with $H_2SO_4$ to get the trisomine.

The synthesis scheme III for trisomine according to this example is as follows:

Synthesis Scheme III

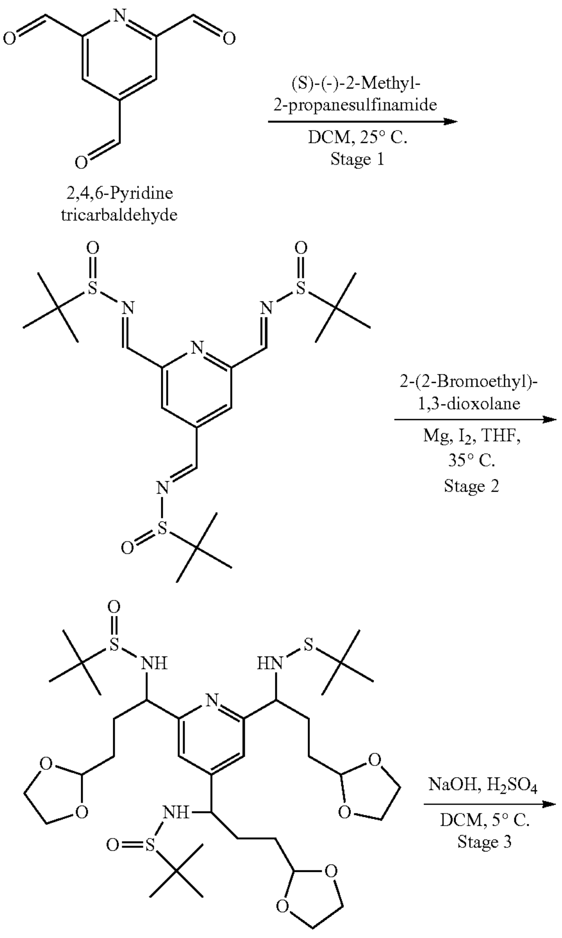

-continued

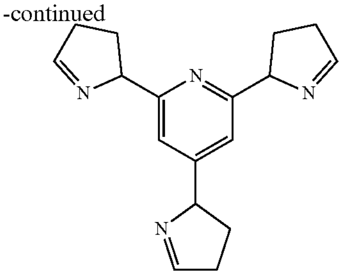

Trisomine

The 2,4,6-pyridine tricarbaldehyde (RSM) was synthesized as follows:

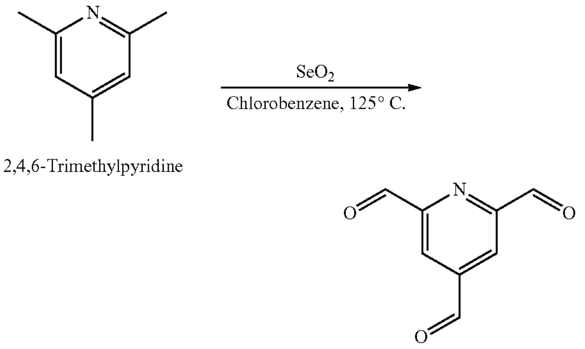

2,4,6-Trimethylpyridine 2,4,6-Pyridine tricarbaldehyde

Representative synthetic protocol 2,4,6-pyridine tricarbaldehyde was performed by adding selenium dioxide (4.12 kg, 4.5 eq.) to a stirred solution of 2,4,6-trimethyl pyridine (1.0 kg, 1.0 eq.) in chlorobenzene (10.0 L, 10.0 vol.) at 25 to 30° C.

Figure 16:
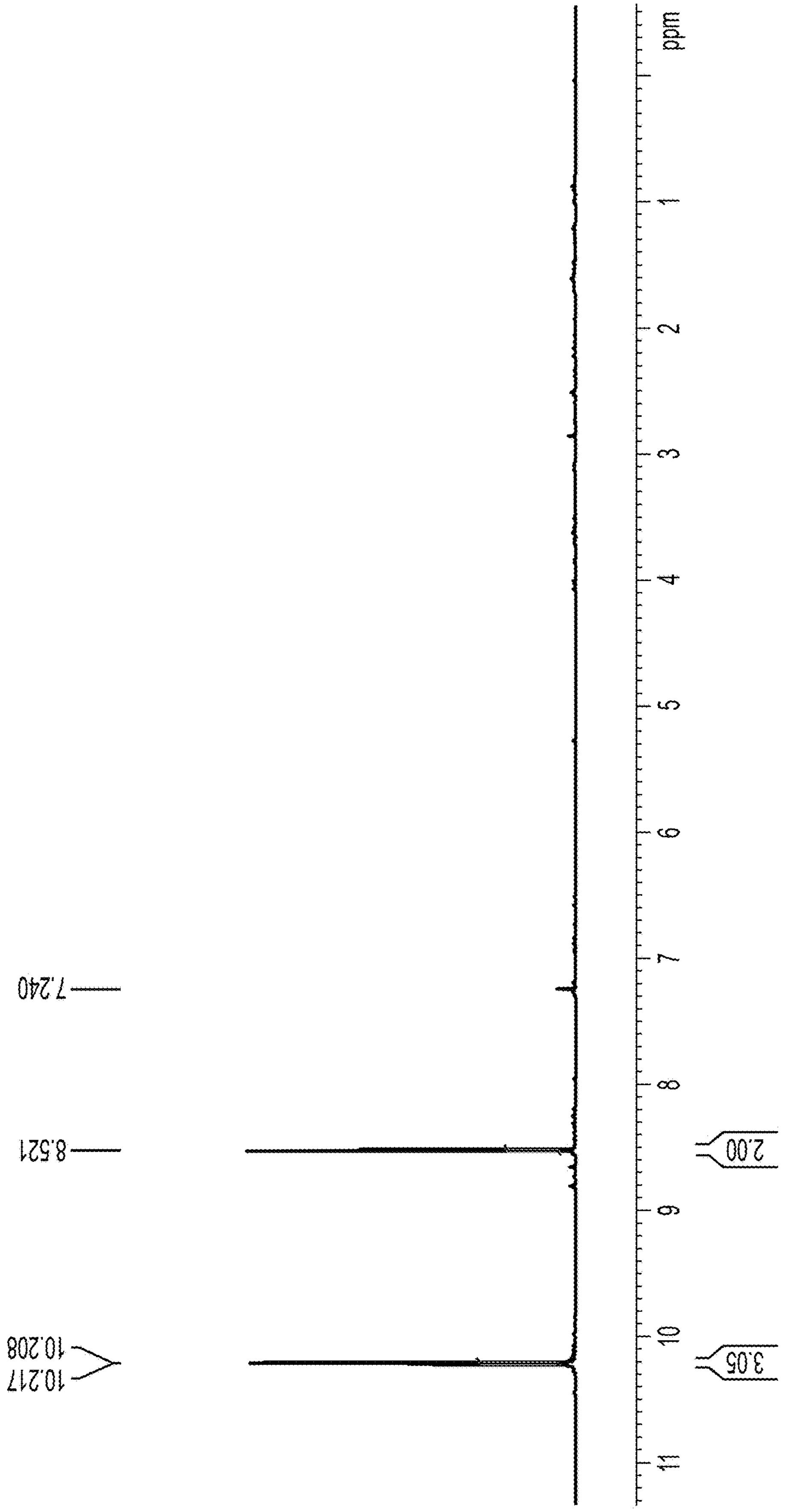
FIG. 16 shows $^1$H NMR spectrum of 2,4,6-pyridine tricarbaldehyde (CDCl3, 400 MHz) in synthesis scheme III of 2,4,6-Tri(3,4-dihydro-2H-pyrrol-2-yl)pyridine in Example 8.
Figure 17:
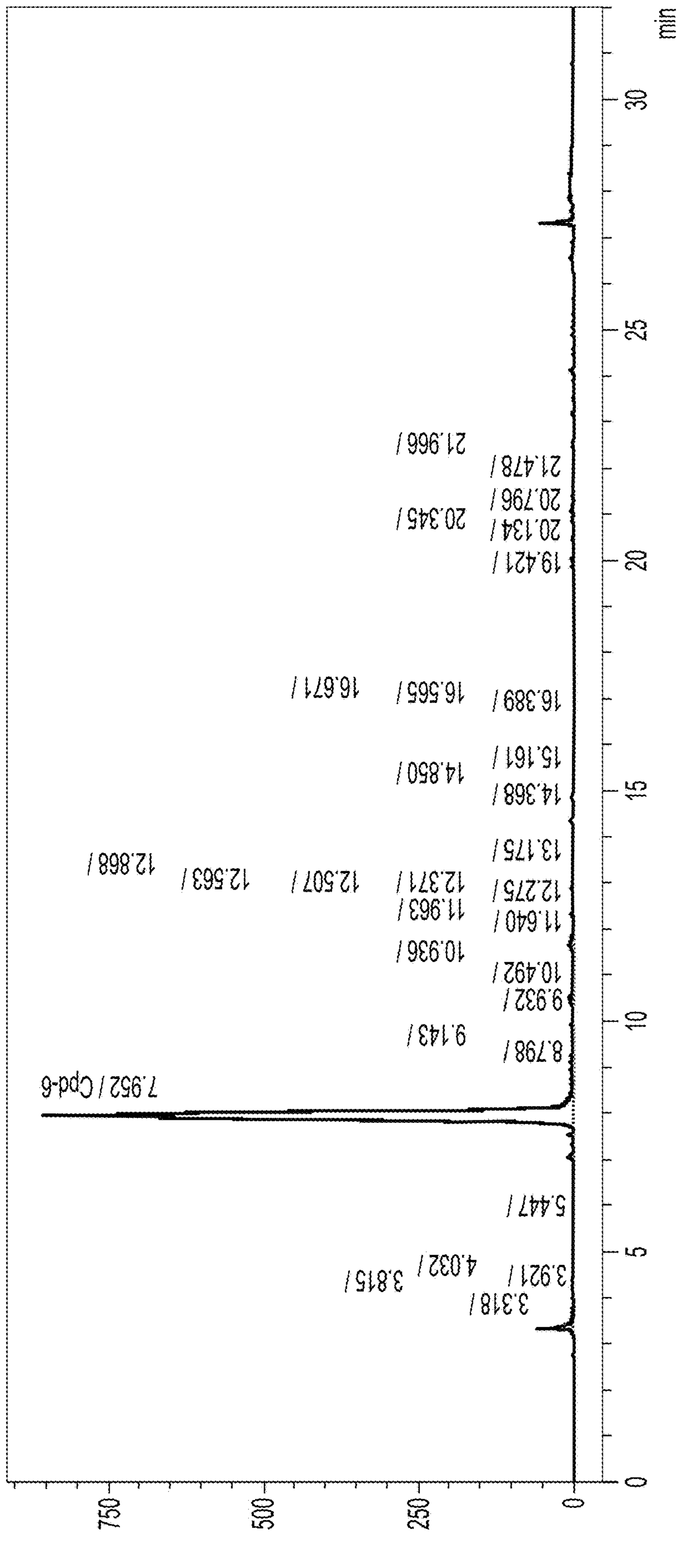
FIG. 17 shows HPLC chromatogram of 2,4,6-pyridine tricarbaldehyde.

Reaction was mass gradually heated to 125±5° C. and stirred for 8 hours at 125±5° C. Progress of the reaction was monitored by TLC (5% MeOH in DCM). After completion of the reaction, reaction mass was filtered through celite bed, bed washed with chlorobenzene (1.0 L, 1.0 vol.). Filtrate was concentrated to completely and dried at 45±5° C. under reduced pressure to get brown solid. Output: 97.3 g, 7.2%. The structure was confirmed by using $^1H$ NMR: (400 MHz, CDCl3): δ 10.21 (s, 1H), δ 10.20 (s, 2H), 8.52 (s, 2H) as shown in FIG. 16. Purity was measured by using HPLC: 90.6 (% area) as shown in FIG. 17 and Table 5 below.

TABLE 5

HPLC results of synthesized 2,4,6-pyridine tricarbaldehyde.
Peak Table
Detector A Channel 2 280 nm

| Peak # | Ret. Time (min) | RRT | Height | Area | Area % | Name |
|---|---|---|---|---|---|---|
| 1 | 3.318 | 0.417 | 62034 | 359576 | 3.679 | |
| 2 | 3.815 | 0.480 | 272 | 1052 | 0.011 | |
| 3 | 3.921 | 0.493 | 345 | 3031 | 0.031 | |
| 4 | 4.052 | 0.510 | 315 | 2940 | 0.030 | |
| 5 | 5.447 | 0.685 | 920 | 21838 | 0.215 | |
| 6 | 7.952 | 1.000 | 853854 | 8859733 | 90.650 | Cpd-6 |
| 7 | 8.798 | 1.106 | 787 | 9542 | 0.098 | |
| 8 | 9.143 | 1.150 | 338 | 2245 | 0.023 | |
| 9 | 9.932 | 1.249 | 5375 | 44682 | 0.457 | |
| 10 | 10.492 | 1.319 | 8357 | 110676 | 1.132 | |
| 11 | 10.936 | 1.375 | 279 | 2351 | 0.024 | |
| 12 | 11.610 | 1.464 | 7243 | 96897 | 0.991 | |
| 13 | 11.963 | 1.504 | 477 | 2846 | 0.029 | |
| 14 | 12.275 | 1.544 | 2446 | 26329 | 0.269 | |
| 15 | 12.371 | 1.556 | 1766 | 8338 | 0.085 | |
| 16 | 12.507 | 1.573 | 1271 | 7118 | 0.073 | |
| 17 | 12.563 | 1.580 | 1106 | 8122 | 0.083 | |
| 18 | 12.868 | 1.618 | 2922 | 30218 | 0.309 | |
| 19 | 13.175 | 1.657 | 343 | 4036 | 0.041 | |
| 20 | 14.368 | 1.807 | 4571 | 57489 | 0.588 | |
| 21 | 14.850 | 1.868 | 3866 | 52494 | 0.537 | |
| 22 | 15.161 | 1.907 | 800 | 3105 | 0.032 | |
| 23 | 16.389 | 2.061 | 866 | 5596 | 0.057 | |
| 24 | 16.565 | 2.083 | 2698 | 20302 | 0.208 | |
| 25 | 16.671 | 2.096 | 1520 | 12172 | 0.125 | |
| 26 | 19.421 | 2.442 | 1323 | 8004 | 0.082 | |
| 27 | 20.134 | 2.532 | 580 | 4051 | 0.041 | |
| 28 | 20.345 | 2.558 | 168 | 857 | 0.009 | |
| 29 | 20.796 | 2.615 | 425 | 2462 | 0.025 | |
| 30 | 21.478 | 2.701 | 181 | 1720 | 0.018 | |
| 31 | 21.966 | 2.762 | 595 | 4568 | 0.047 | |
| Total | | | 968244 | 9773591 | 100.000 | |

Figure 18:
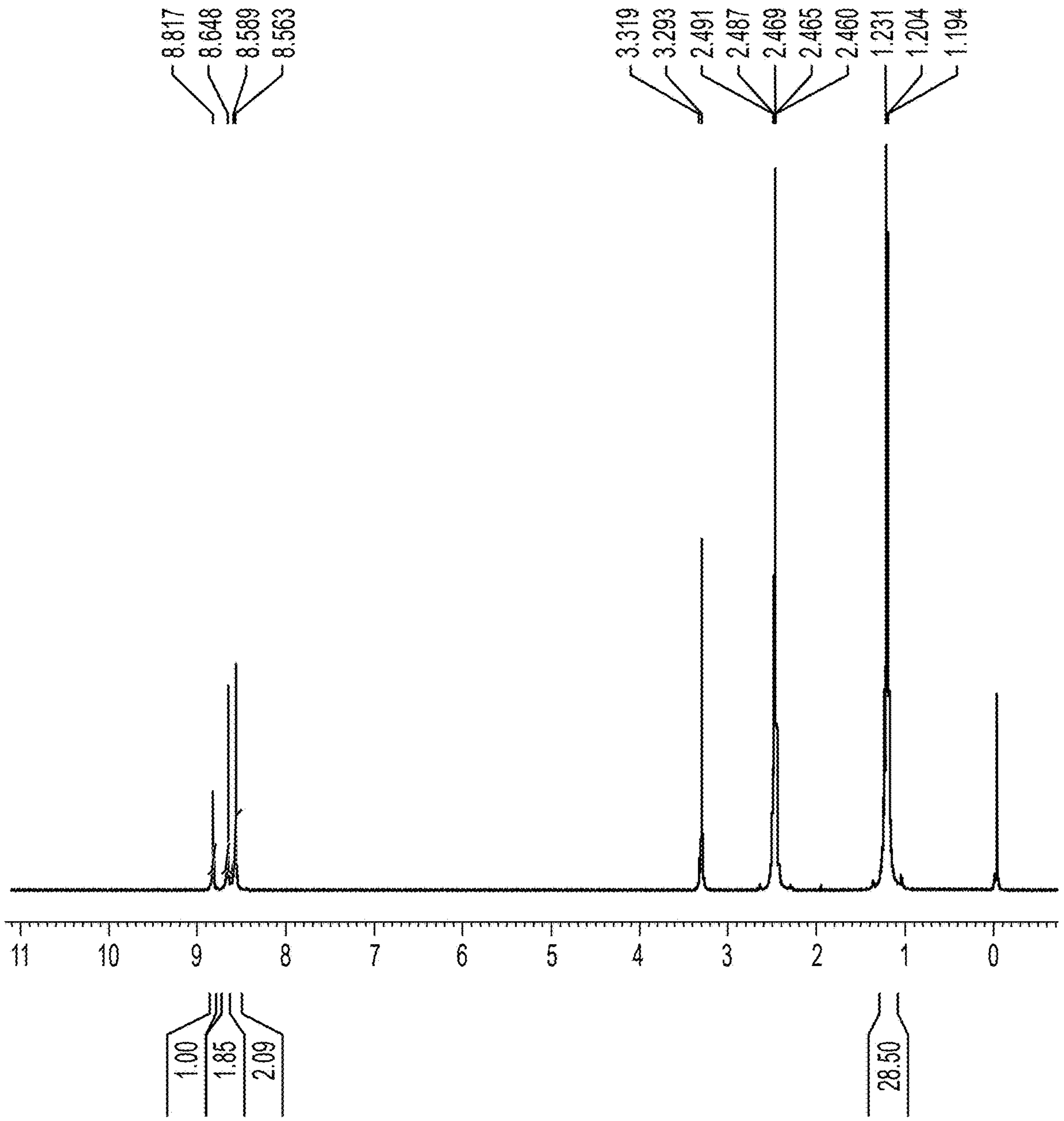
FIG. 18 shows $^1$H NMR spectrum of Stage 1 (DMSO, 400 MHz) in synthesis scheme III of 2,4,6-Tri(3,4-dihydro-2H-pyrrol-2-yl)pyridine in Example 8.
Figure 19:
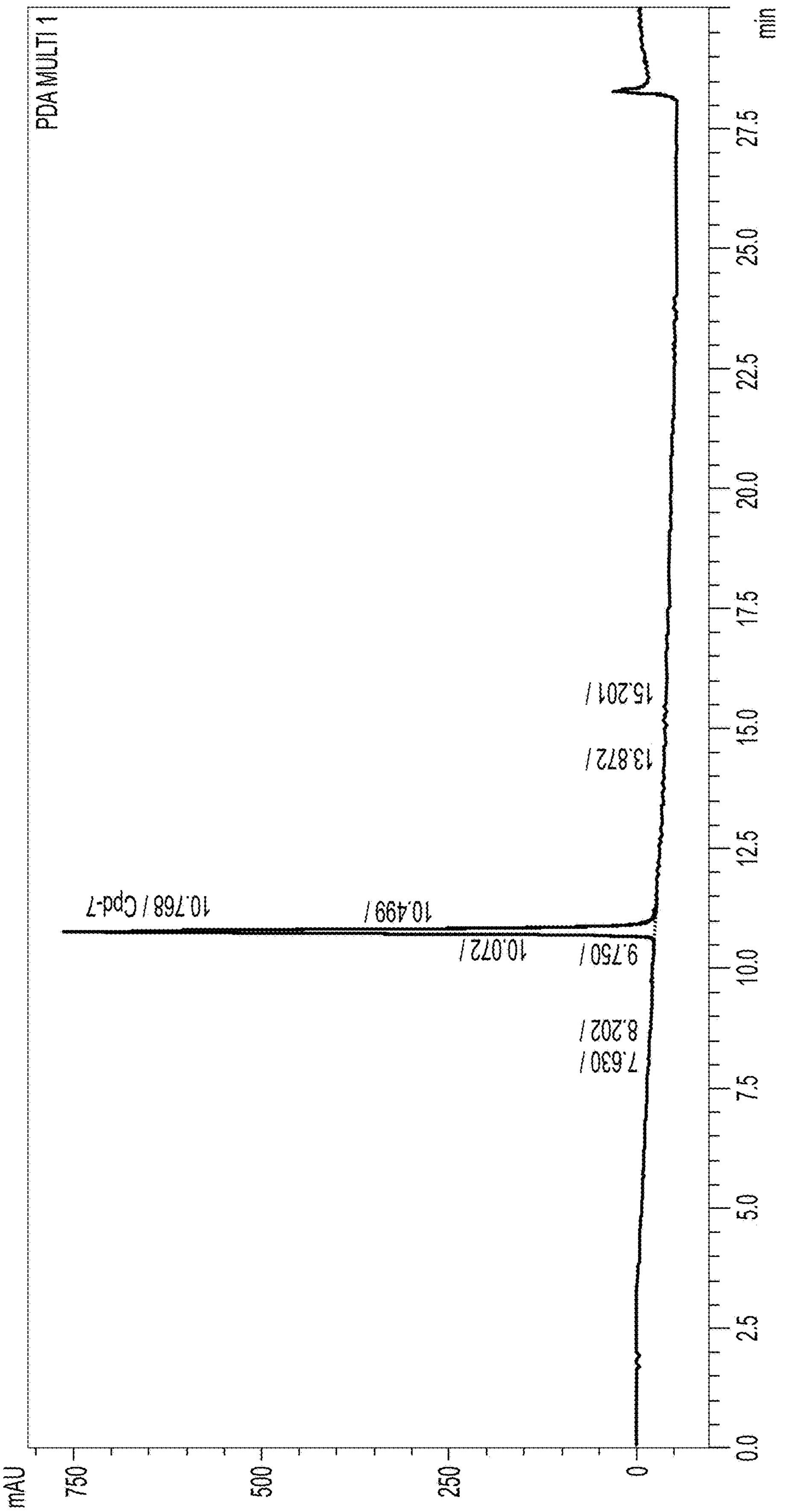
FIG. 19 shows HPLC chromatogram of the Stage 1 product in synthesis scheme III of 2,4,6-Tri(3,4-dihydro-2H-pyrrol-2-yl)pyridine in Example 8.

Stage 1 of Synthesis Scheme III was Performed as Follows:

Charged 2,4,6-pyridine tricarbaldehyde (120.0 g, 1.0 eq.) and DCM (2.4 L, 20.0 vol.) into the reactor at 25±5° C. and cooled to 0-5°. Charged S-(−)-2-methyl-2-propanesulfinamide (276.4 g, 3.1 eq.) and PTSA (38.0 g, 0.3 eq.) at 0° C. Allowed the reaction mass to 25±5° C. and stirred for 20 hours at 25±5° C. Reaction progress was monitored by TLC (10% MeOH in DCM). After completion of reaction, the reaction mass was concentrated completely and diluted with EtOAc (1.8 L, 15.0 vol.). To the diluted mass charged sat. sodium bicarbonate solution (1.2 L, 10.0 vol) and stirred for 10 minutes. The layers was allowed to separate and aqueous layer was washed with EtOAc (360.0 mL, 3.0 vol). The combined organic layer was washed with 10% aq. sodium chloride solution (1.2 L, 10.0 vol.). Added charcoal (2% w/w) to the above organic layer and slurried for 2 hours at 25±5° C. Filtered through celite bed, bed washed with ethyl acetate (240.0 mL, 2.0 vol.). Filtrate was concentrated completely under reduced pressure at 45° C. To this hexane (1.2 L, 10.0 vol.) was charged and continued stirring for 30 minutes at 25±5° C. Solid was filtered and washed with hexane (360.0 mL, 3.0 vol.). Solid was unloaded and dried under reduced pressure for 2 hours at 45° C. to get pale yellow solid. Output in stage 1: 238.8 g, 68.6%. $^1H$ NMR was used to confirm the structure: $^1H$ NMR (400 MHz, DMSO): δ 8.81 (s, 1H), 8.64 (s, 2H), 8.58 (s, 2H), 1.23-1.19 (m, 27H) as shown in FIG. 18. HPLC was used to evaluate purity: 98.9 (% area) as shown in FIG. 19 and Table 6 below.

TABLE 6

HPLC determination of purity of Stage 1 product in synthesis scheme III:
Peak Table
PDA CH1 220 nm

| Peak # | Ret. Time (min) | RRT | Height | Area | Area % | Name |
|---|---|---|---|---|---|---|
| 1 | 7.630 | 0.709 | 883 | 5019 | 0.096 | |
| 2 | 8.202 | 0.762 | 481 | 2509 | 0.048 | |
| 3 | 9.750 | 0.905 | 1689 | 12020 | 0.230 | |
| 4 | 10.072 | 0.935 | 776 | 3865 | 0.074 | |
| 5 | 10.499 | 0.975 | 1322 | 8150 | 0.156 | |
| 6 | 10.768 | 1.000 | 788937 | 5178475 | 98.948 | Cpd-7 |
| 7 | 13.872 | 1.288 | 842 | 5809 | 0.111 | |
| 8 | 15.201 | 1.412 | 2478 | 17701 | 0.338 | |
| Total | | | 797409 | 5233548 | 100.000 | |

Figure 20:
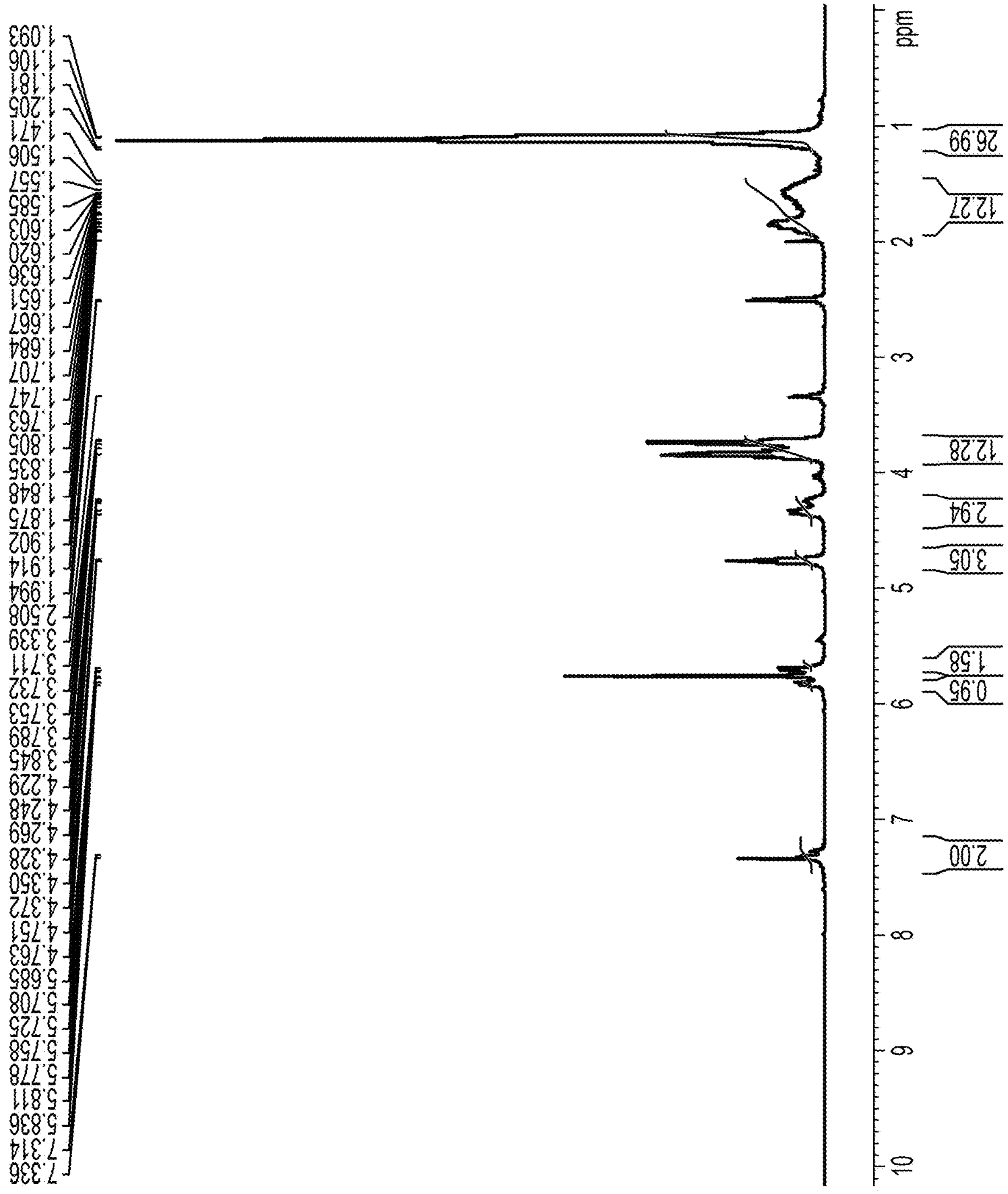
FIG. 20 shows $^1$H NMR spectrum of Stage 2 product in synthesis scheme III of 2,4,6-Tri(3,4-dihydro-2H-pyrrol-2-yl)pyridine in Example 8.
Figure 21:
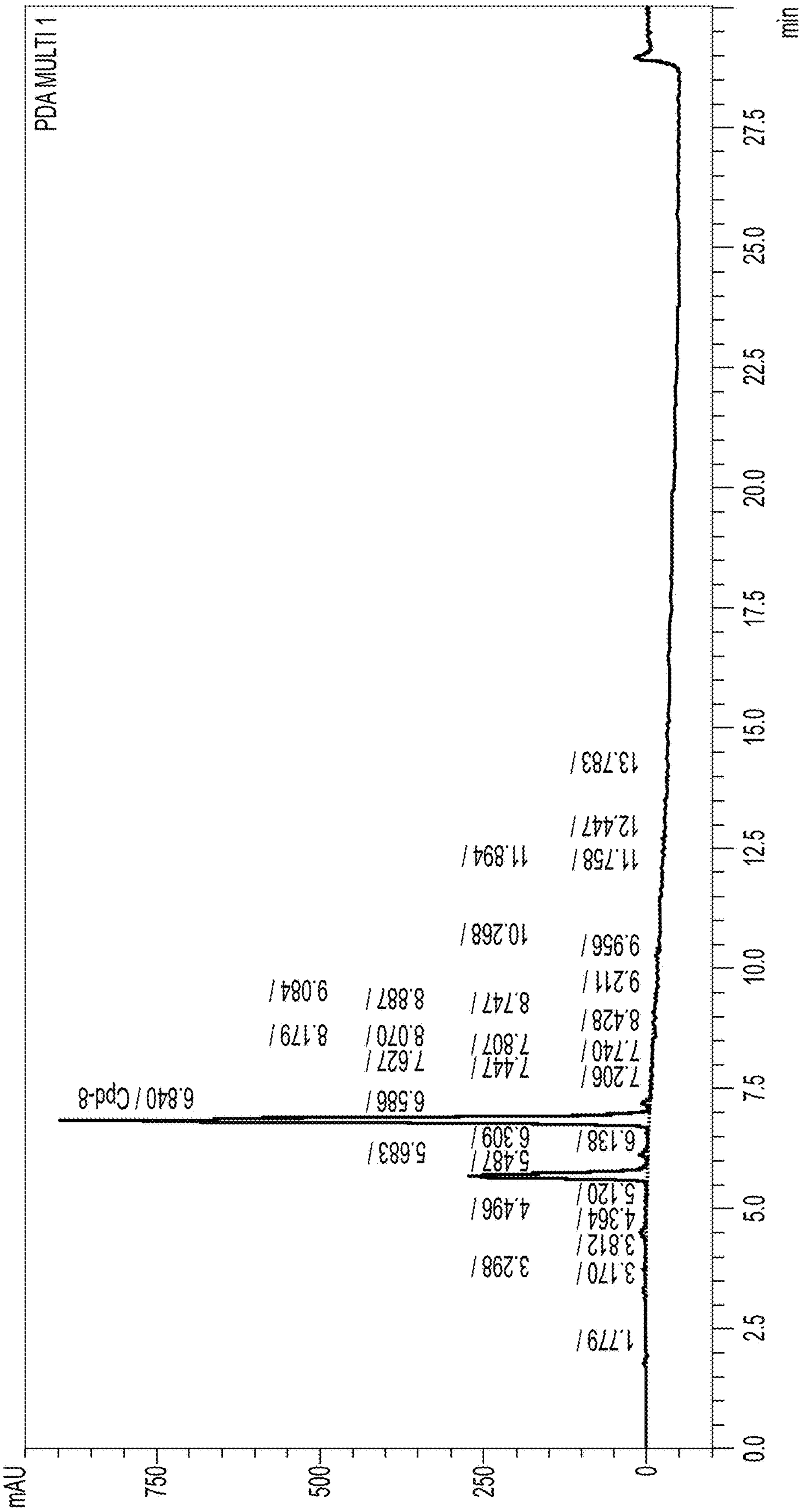
FIG. 21 shows HPLC chromatogram of the Stage 2 product in synthesis scheme III of 2,4,6-Tri(3,4-dihydro-2H-pyrrol-2-yl)pyridine in Example 8.

Stage 2 Reaction of Synthesis Scheme II:

Charged magnesium turnings (56.6 g, 11.0 eq.) and iodine (catalytic) in dry THF (1.0 L, 10.0 vol.) at 25±5° C. under nitrogen atmosphere. Heated to the mass 35° C. and added 1,2 dibromo ethane (3.97 g, 0.1 eq.) at 35±5° C. and stirred for 30 minutes. Added a solution of 2-(2-Bromoethyl)-1,3-dioxolane (383.0 g 10.0 eq.) in dry THF (500.0 mL, 5.0 vol.) to the above mixture at 35±5° C. and stirred for 2 hours at the same temperature. Added a solution of Stage 1 (100.0 g, 1.0 eq.) in dry THF (500.0 mL, 5.0 vol.) at 35±5° C. over a period of 2 hours and continued the stirring for additional 16 hours at 30±5° C. Progress of the reaction was monitored by TLC (10% MeOH in DCM). After completion of reaction, cooled the mass to 5-10° C. Quenched the reaction mass with aqueous saturated ammonium chloride solution (1.0 L, 10.0 vol.) at below 20° C. Stirred the reaction mixture at 25±5° C. for 30 minutes. Diluted the mass with ethyl acetate (1.0 L, 10.0 vol.) and filtered through celite bed. The layers was allowed to separate and re-extracted the aqueous layer with ethyl acetate (1.0 L, 10.0 vol.) 2 times. Separated the layers and combined organic layer was concentrated and dried under reduced pressure for 1 hour to get brown syrup. Crude compound was purified by column chromatography using ethyl acetate and methanol. Output of stage 2: 100 g (60.6%). $^1H$ NMR was used to confirm the structure: $^1H$ NMR (300 MHz, DMSO): δ 7.33 (s, 2H), 5.83 (s, 7.8 Hz, 1H), 5.68 (s, 6.9 Hz, 2H), 4.76 (br, 3H), 4.35-4.22 (m, 3H), 3.84-3.71 (m, 12H), 1.83-1.47 (s, 12H), 1.20-1.10 (s, 27H) as shown in FIG. 20. HPLC was used to evaluate purity: 94% area (peak 1+peak 2) as shown in FIG. 21 and Table 7 below.

TABLE 7

Purity of Stage 2 product in synthesis scheme III
Peak Table
PDA Ch1 220 nm

| Peak # | Ret. Time (min) | RRT | Height | Area | Area % | Name |
|---|---|---|---|---|---|---|
| 1 | 1.779 | 0.260 | 2102 | 7325 | 0.084 | |
| 2 | 3.170 | 0.463 | 398 | 1657 | 0.019 | |
| 3 | 3.298 | 0.482 | 1654 | 8982 | 0.102 | |
| 4 | 3.812 | 0.557 | 495 | 5240 | 0.060 | |
| 5 | 4.364 | 0.638 | 891 | 4585 | 0.052 | |
| 6 | 4.496 | 0.657 | 7123 | 69004 | 0.787 | |
| 7 | 5.120 | 0.749 | 1162 | 8561 | 0.098 | |
| 8 | 5.487 | 0.802 | 933 | 3229 | 0.037 | |
| 9 | 5.683 | 0.831 | 274110 | 2148580 | 24.500 | |
| 10 | 6.138 | 0.897 | 9821 | 79724 | 0.908 | |
| 11 | 6.309 | 0.922 | 1211 | 5896 | 0.067 | |

TABLE 7-continued

Purity of Stage 2 product in synthesis scheme III
Peak Table
PDA Ch1 220 nm

| Peak # | Ret. Time (min) | RRT | Height | Area | Area % | Name |
|---|---|---|---|---|---|---|
| 12 | 6.586 | 0.963 | 2502 | 15582 | 0.178 | |
| 13 | 6.840 | 1.000 | 901351 | 6196158 | 70.654 | Cpd-8 |
| 14 | 7.206 | 1.053 | 11690 | 70672 | 0.806 | |
| 15 | 7.447 | 1.089 | 1448 | 6751 | 0.077 | |
| 16 | 7.627 | 1.115 | 1798 | 11137 | 0.127 | |
| 17 | 7.740 | 1.132 | 648 | 2520 | 0.029 | |
| 18 | 7.807 | 1.141 | 577 | 1852 | 0.021 | |
| 19 | 8.070 | 1.180 | 1551 | 9307 | 0.106 | |
| 20 | 8.179 | 1.196 | 2443 | 15287 | 0.174 | |
| 21 | 8.428 | 1.232 | 512 | 2637 | 0.030 | |
| 22 | 8.747 | 1.279 | 520 | 2385 | 0.027 | |
| 23 | 8.887 | 1.299 | 2816 | 16536 | 0.189 | |
| 24 | 9.084 | 1.328 | 4348 | 28241 | 0.322 | |
| 25 | 9.211 | 1.347 | 1216 | 6204 | 0.071 | |
| 26 | 9.956 | 1.455 | 1224 | 6194 | 0.071 | |
| 27 | 10.268 | 1.501 | 4229 | 25601 | 0.292 | |
| 28 | 11.758 | 1.719 | 331 | 1091 | 0.012 | |
| 29 | 11.894 | 1.739 | 637 | 2573 | 0.029 | |
| 30 | 12.447 | 1.820 | 749 | 3426 | 0.039 | |
| 31 | 13.783 | 2.015 | 299 | 2762 | 0.031 | |
| Total | | | 1240789 | 8769598 | 100.000 | |

Figure 22:
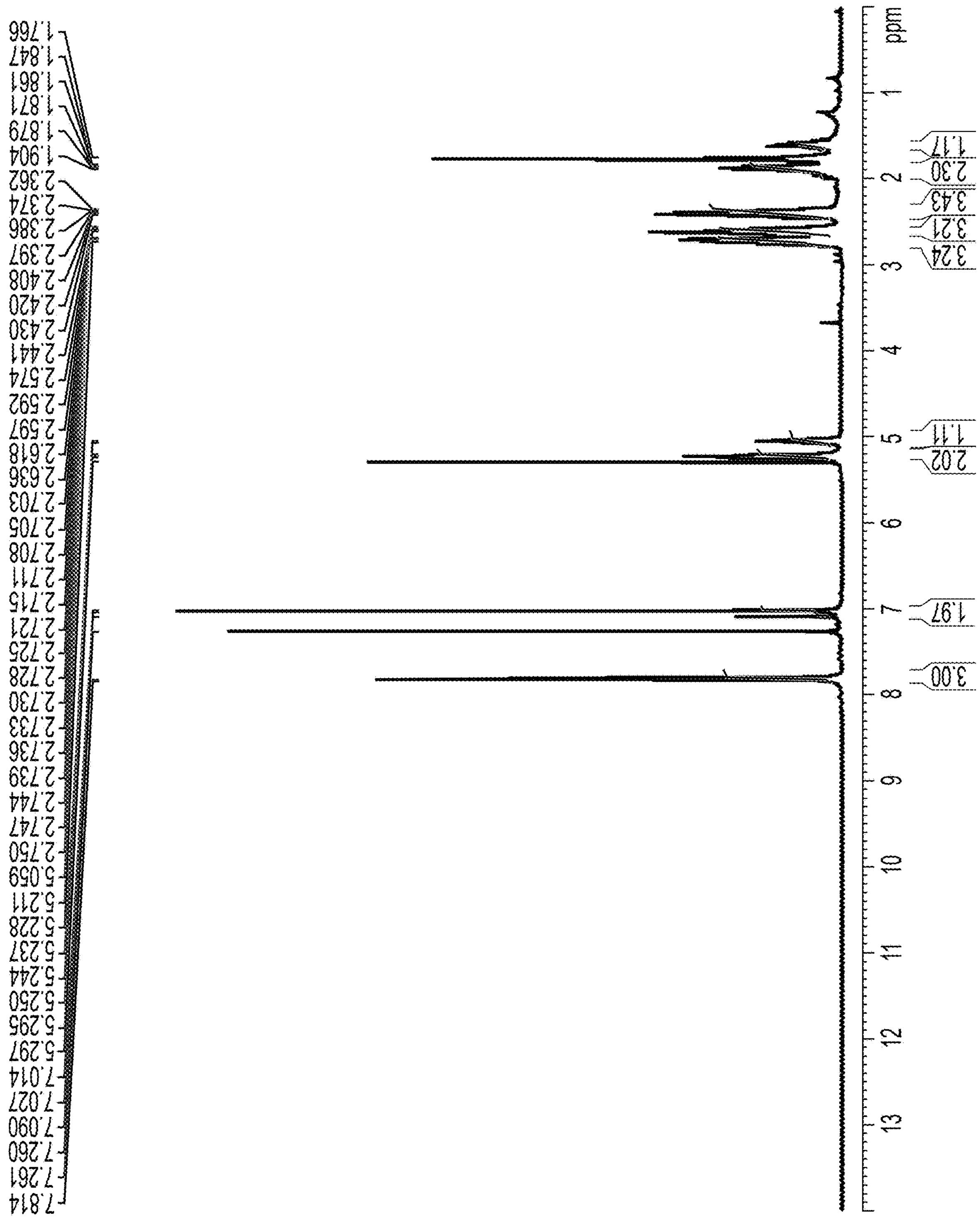
FIG. 22 shows $^1$H NMR spectrum of Stage 3 product in synthesis scheme III of 2,4,6-Tri(3,4-dihydro-2H-pyrrol-2-yl)pyridine in Example 8.
Figure 23:
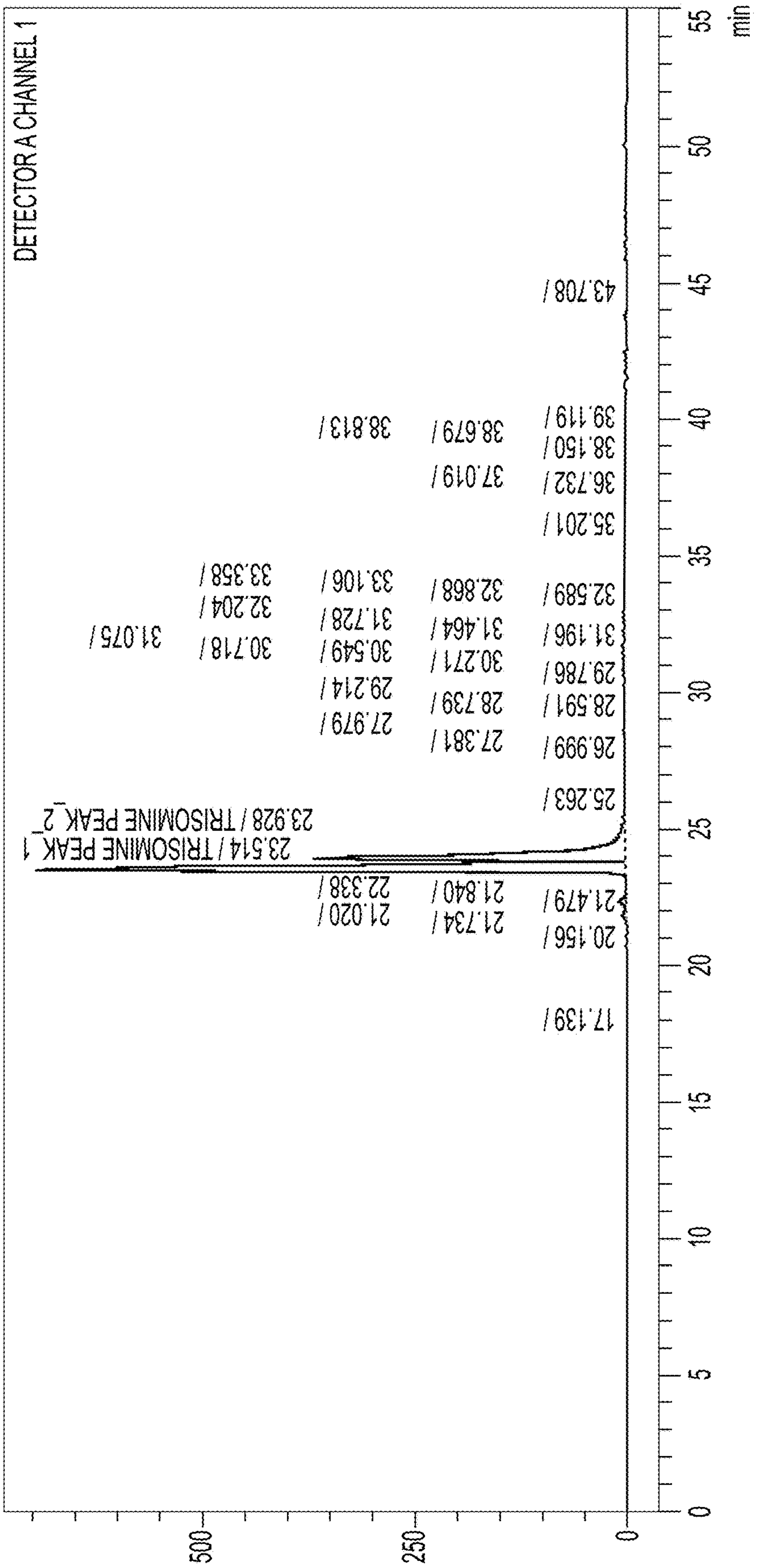
FIG. 23 shows HPLC chromatogram of the Stage 3 product in synthesis scheme III of 2,4,6-Tri(3,4-dihydro-2H-pyrrol-2-yl)pyridine in Example 8.

Stage 3 Reaction of Synthesis Scheme III was Performed as Follows:

Stage 2 (20.0 g, 1.0 eq.) product was dissolved in DCM (100.0 mL, 5.0 vol) at 25±5° C. Cooled the solution to 0-5° C. and added 10% aq. Sulphuric acid (600.0 mL, 30.0 vol.) slowly at 0-5° C. Stirred the reaction mass for 4 hours at 0±5° C. Progress of the reaction was monitored by TLC. After reaction completion, reaction mass allowed to separate the organic and aqueous layers, aqueous layer was washed with DCM (200.0 mL, 10.0 vol.) five times. The aqueous layer was added in to the 20% sodium hydroxide solution (400.0 mL, 20.0 vol.) at 5-10° C. over a period of 1 hour. The pH of the mass was adjusted using 20% sodium hydroxide solution (40.0 mL, 2.0 vol.) to obtain the pH about 12.6. Aqueous layer was extracted with cold DCM (200.0 mL, 10.0 vol.) five times. Combined the organic layer concentrated at below 28° C. to get pale brown solid. Output of stage 3: 5.9 g (82.0%). $^1H$ NMR was used to confirm the structure: $^1H$ NMR (400 MHz, $CDCl_3$): δ 7.81-7.80 (m, 3H), 7.07-7.00 (m, 2H), 5.18-5.24 (m, 2H), 5.06-5.01 (m, 1H), 2.75-2.67 (m, 3H), 2.64-2.55 (m, 3H), 2.44-2.33 (m, 3H), 2.44-2.33 (m, 3H), 1.95-1.80 (m, 2H), 1.65-1.50 (m, 1H) as shown in FIG. 22. Purity was measured by using HPLC: HPLC purity: 92.9% area (peak 1+peak 2) as shown in FIG. 23 and Table 8 below.

TABLE 8

Purity of Stage 3 product (Trisomine)
Detector A Channel 1 260 nm
Peak Table

| Peak # | Ret. Time (min) | RRT | Height | Area | Area % | Name |
|---|---|---|---|---|---|---|
| 1 | 17.139 | 0.729 | 374 | 4066 | 0.025 | |
| 2 | 20.156 | 0.857 | 409 | 3715 | 0.022 | |
| 3 | 20.734 | 0.882 | 774 | 6683 | 0.040 | |
| 4 | 21.020 | 0.894 | 352 | 3208 | 0.019 | |
| 5 | 21.479 | 0.913 | 234 | 1755 | 0.011 | |
| 6 | 21.840 | 0.929 | 4037 | 53658 | 0.324 | |
| 7 | 22.338 | 0.950 | 9368 | 127882 | 0.771 | |

TABLE 8-continued

Purity of Stage 3 product (Trisomine)
Detector A Channel 1 260 nm
Peak Table

| Peak # | Ret. Time (min) | RRT | Height | Area | Area % | Name |
|---|---|---|---|---|---|---|
| 8 | 23.514 | 1.000 | 692823 | 9690952 | 58.437 | trisomine peak-1 |
| 9 | 23.928 | 1.018 | 368259 | 6169241 | 37.201 | trisomine peak-2 |
| 10 | 25.263 | 1.074 | 2702 | 78055 | 0.471 | |
| 11 | 26.999 | 1.148 | 254 | 2315 | 0.014 | |
| 12 | 27.381 | 1.164 | 362 | 3909 | 0.024 | |
| 13 | 27.979 | 1.190 | 953 | 14948 | 0.090 | |
| 14 | 28.591 | 1.216 | 1096 | 11756 | 0.071 | |
| 15 | 28.739 | 1.222 | 750 | 5063 | 0.031 | |
| 16 | 29.214 | 1.242 | 541 | 4546 | 0.027 | |
| 17 | 29.786 | 1.267 | 647 | 4177 | 0.025 | |
| 18 | 30.271 | 1.287 | 1617 | 9837 | 0.059 | |
| 19 | 30.549 | 1.299 | 2254 | 44804 | 0.270 | |
| 20 | 30.718 | 1.306 | 2320 | 31729 | 0.191 | |
| 21 | 31.075 | 1.322 | 2026 | 31994 | 0.193 | |
| 22 | 31.196 | 1.327 | 1735 | 14527 | 0.088 | |
| 23 | 31.464 | 1.338 | 2455 | 37481 | 0.226 | |
| 24 | 31.728 | 1.349 | 1667 | 28952 | 0.175 | |
| 25 | 32.204 | 1.370 | 2197 | 31653 | 0.191 | |
| 26 | 32.589 | 1.386 | 2125 | 46742 | 0.282 | |
| 27 | 32.868 | 1.398 | 1353 | 16900 | 0.102 | |
| 28 | 33.106 | 1.408 | 738 | 5361 | 0.032 | |
| 29 | 33.358 | 1.419 | 489 | 7483 | 0.045 | |
| 30 | 35.201 | 1.497 | 387 | 11519 | 0.069 | |
| 31 | 36.732 | 1.562 | 1208 | 20744 | 0.125 | |
| 32 | 37.019 | 1.574 | 1436 | 33949 | 0.205 | |
| 33 | 38.150 | 1.622 | 472 | 2892 | 0.017 | |
| 34 | 38.679 | 1.645 | 1041 | 11528 | 0.070 | |
| 35 | 38.813 | 1.651 | 646 | 5010 | 0.030 | |
| 36 | 39.119 | 1.664 | 249 | 2407 | 0.015 | |
| 37 | 43.780 | 1.862 | 228 | 2207 | 0.013 | |
| Total | | | 1110579 | 16583647 | 100.000 | |

Example 9: Affinity Computations of 2,4,6-tris(3,4-dihydro-2H-pyrrol-2-yl)pyridine and $Fe^{2+}$ Ions in Water Solution

Introduction

Water is a complex environment that is capable of interacting with solutes, especially with charged molecules, in several different ways.

The NIST SRD46: Critically Selected Stability Constants of Metal Complexes database was used to obtain several affinity constants pertaining to $Fe^{2+}$ complexes and the dissociation constant for the iron complex of diethylenetriamine, [dien-Fe]2+, record 3201, with a pK=6.33 or equivalently with a $\Delta G^0$=36.11 kJ/mol was chosen for this study. The structures of the two test compounds are shown below:

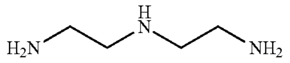

diethylenetriamine

-continued

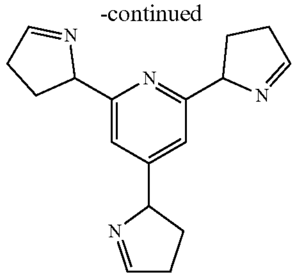

2,4,6-tris(3,4-dihydro-2H-pyrrol-2-yl)pyridine

"2,4,6-tris(3,4-dihydro-2H-pyrrol-2-yl)pyridine" is sometimes referred to herein as "D102," and these two terms are equivalent.

Methods:

All computations were performed in parallel for 2,4,6-tris(3,4-dihydro-2H-pyrrol-2-yl)pyridine and diethylenetriamine.

For each complex and their dissociation products the computation was conducted in different phases at different levels of approximation as explained in "A Chemist's Guide to Density Functional Theory, 2nd Edition, Wolfram Koch, Max C. Holthausen, ISBN: 978-3-527-30372-4. The computations were conducted by using the following models:

1. Hartree Fock-3c (HF-3c) is a low theory level and does not consider the solvent, It contains some empirical corrections to HF. The obtained geometries are usually good and are the main reason for this kind of computation. It is based on a three term correction of an HF calculation in a minimal MINIX basis set.
2. Density Functional Theory (DFT)-B3LYP def2-TZVP: a standard good theory level with binding affinity estimates accuracy within 8 kJ/mol in vacuum. It provides a good idea of the process and can validate the geometries obtained in the first step. It does not take into consideration solvent effect.
3. DFT-B3LYP def2-TZVP CPCM SMD: the solvent is treated as a continuous dielectric, the electrostatic effects are mainly correct, but chemospecific solvent effects are not taken into account. In this model, the molecule is surrounded, outside of an excluded volume, by a polarizable medium. Therefore, the electrical charge distribution of the solute induces apparent polarization charges on the separation surface, which in turn generate electrostatic forces on the solute. See Sure, et al., Comput. Chem. 2013, 34, 1672-1685. DOI: 10.1002/jcc.23317, and Barone, et al., (1998) J. Phys. Chem. A, 102, 1995.

DFT-B3LYP def2-TZVP CPCM SMD+explicit water: several explicit water molecules are added to the model to gauge the effect of solvent binding effects. Thermodynamic properties are evaluated at the minimum energy conformations and alongside short fixed temperature quantum molecular (QM) dynamics.

Results

Figure 24:
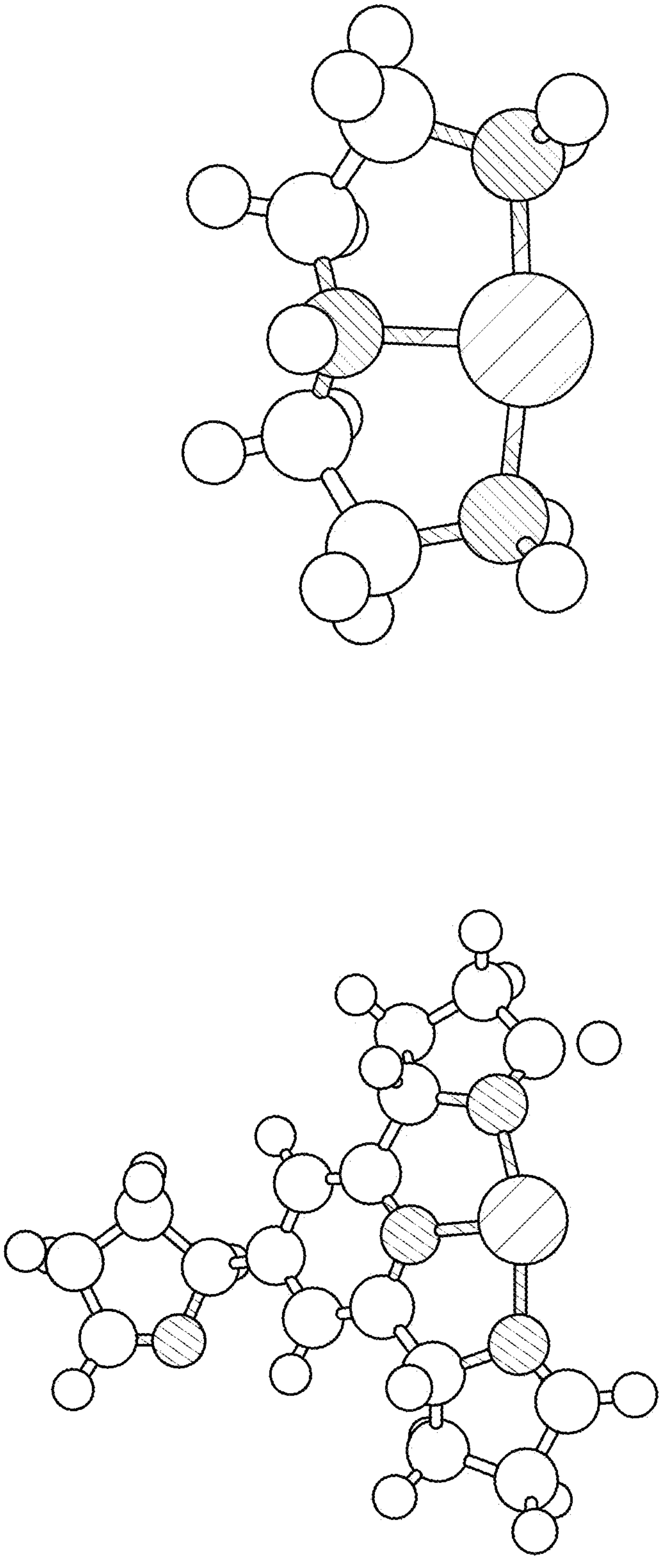
FIG. 24 shows structure optimization without explicit water molecules.

A short phase of HF-3c sampling showed that both [2,4,6-tris(3,4-dihydro-2H-pyrrol-2-yl)pyridine—Fe2+] and [diethylenetriamine—Fe2+] have tridented stable conformations as shown in FIG. 24. The formation of the [2,4,6-tris(3,4-dihydro-2H-pyrrol-2-yl)pyridine—Fe2+] is hindered by the rigidity of the structure, and it can only be formed by forcing the system to overcome the transition configuration. By increasing the level of approximation, Phases 2 and 3 did not change visibly the results. This is expected as molecular structures and bond parameters such as bond lengths are rather stable towards these improvements of the theory.

Figure 25:
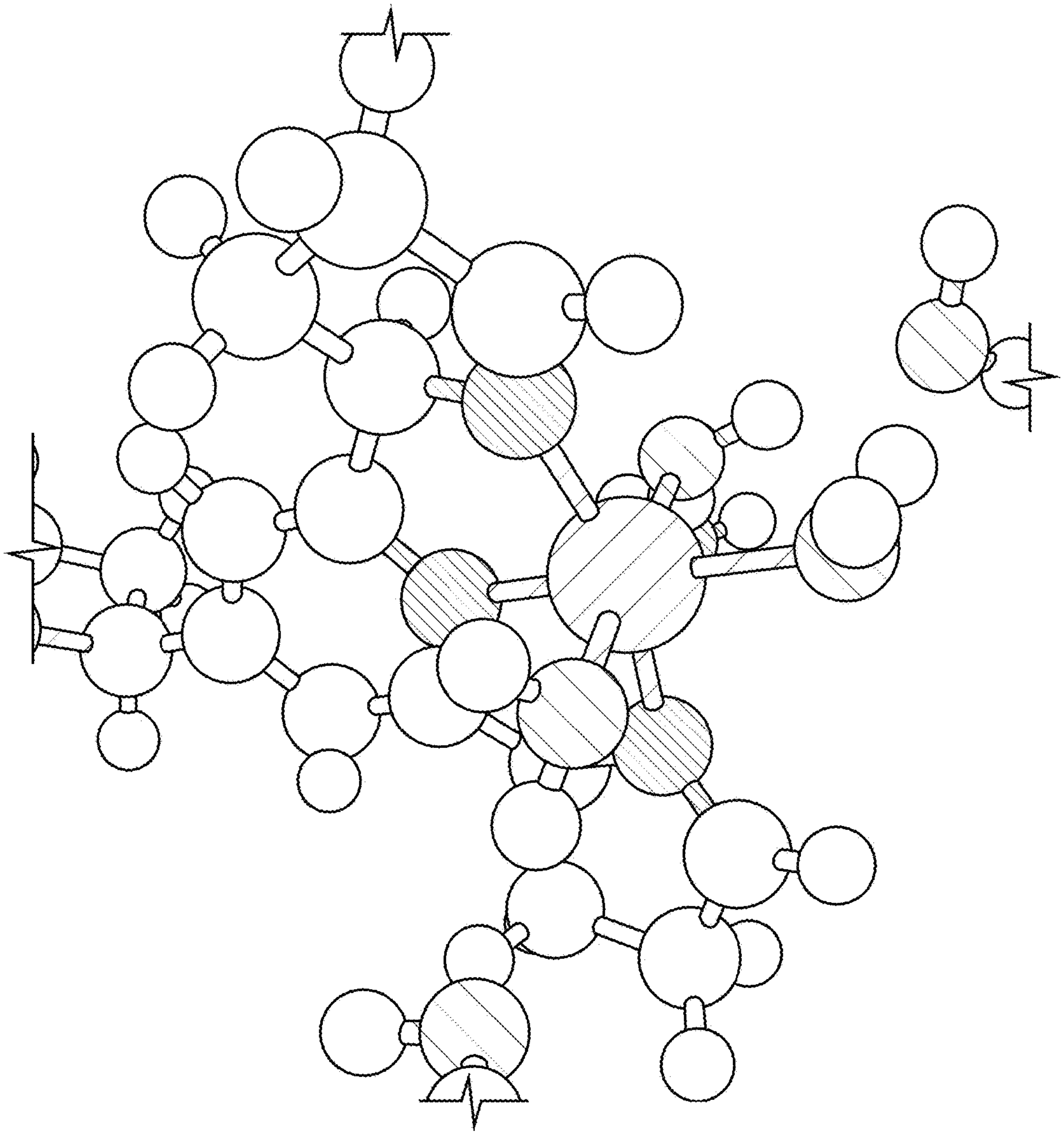
FIG. 25 shows complexation of 2,4,6-Tri(3,4-dihydro-2H-pyrrol-2-yl)pyridine, $Fe^{2+}$, and 6 water molecules.

In phase 4, each of the complexes was prepared with 4, 5, and 6 water molecules, and 3 of these water molecules were always directly coordinated with the Fe2+ ion as shown in FIG. 25.

Of the dissociated parts, iron was computed as $[Fe\text{-}6H_2O]^{2+}$, which is an octahedral complex. The computation was conducted with spin states S=0, 1,2, and confirmed that hydrated iron is preferably in the high spin configuration S=2, which is consistent with empirical rules.

Each of the ligands was computed with 2, 3, and 4 explicit water molecules. In all configurations, one or two water molecules were seen to form specific bonds with the nitrogen atoms of the ligand.

The scheme of the complex formation reaction for a given ligand L is as follows:

$$L + [Fe\bullet 6H_2O]^{2+} \Longleftrightarrow [L\bullet Fe\bullet 6H_2O]^{2+}$$

If two water molecules specifically bind the ligand, the reaction becomes:

$$[L\bullet 2\,H_2O] + [Fe\bullet 6H_2O]^{2+} \Longleftrightarrow [L\bullet Fe\bullet 6H_2O]^{2+} + 2\,H_2O$$

The free water energy for the stoichiometric equilibration was extrapolated from the compounds with different explicit water contents. In addition, the zero point vibrational energy (ZPE) relieved in complex dissociation is reported. The zero point energy is a contribution to be considered since a quantum system is never at rest, as it has a minimum vibrational energy. This vibrational energy is relieved when the system dissociates, usually diminishing the dissociation energy.

From the various energy components, the following complexation of diethylenetriamine is obtained:

$$\Delta U = [\text{dien}\cdot Fe\cdot 6H_2O]^{2+} - [Fe\cdot 6H_2O]^{2+} - [\text{dien}\cdot 2H_2O] + 2*E(H_2O)+ZPE \qquad \text{Eq. 1}$$

-continued $$\Delta U = (-2046.555322 + 1722.106539 + 477.306018 - 2*76.44354 + 0.005989)\ \text{Hartree} = -0.023873\ \text{Hartree} = -62\ \text{kJ/mol}$$

where $E(H_2O)$ has been estimated from the energies of the compounds with varying amounts of explicit water, e.g.:

$$E(H_2O) = (E([\text{dien}\cdot 4H_2O] - E[\text{dien}\cdot 2H_2O]))/2$$

$$E(H_2O) = (-630.193115 + 477.306018)/2\ \text{Hartree} = -76.4435485\ \text{Hartree}$$

It was observed that there is a good linear relationship between energy and number of explicit water molecules. It was observed that the complexation energy $\Delta G^0$ was overestimated by about 25 kJ/mol even considering the $T\Delta S^0$ term of the $\Delta G^0=\Delta U^0-T\Delta S^0$ equation. This discrepancy might be attributed to the complex effects of water that cannot be fully accounted for, and to the density Functional B3LYP treatment of the iron high spin state since this density function has been mainly optimized on a large database of ab initio and experimental data of dissociation energies and structure geometries of organic molecules.

For the complexation of 2,4,6-tris(3,4-dihydro-2H-pyrrol-2-yl)pyridine (D102), it is similarly obtained:

$$E(H_2O) = (E([D102\cdot 4H_2O] - E[D102.2H_2O]))/2 \qquad \text{Eq. 2}$$

$$E(H_2O) = (-1184.377994 + 1031.485547)/2\ \text{Hartree} = 76.44622\ \text{Hartree}$$

$$\Delta U = [D102\cdot Fe\cdot 6H_2O]^{2+} - [Fe\cdot 6H_2O]^{2+} - [D102.2H_2O] + 2*E(H_2O) + ZPE$$

$$\Delta U = (-2600.741175 + 1722.106539 + 1031.48554 - 2*76.44622 + 0.005803)\ \text{Hartree} = -0.0357\ \text{Hartree} = -93.7\ \text{kJ/mol}$$

Table 9 below summarizes the single computational results:

TABLE 9

| Reaction | Compound | Energy (Hartree)[%] | ZPE* (Hartree) |
|---|---|---|---|
| dien complexation | $[Fe\cdot 6H_2O]^{2+}$ | −1722.106539 | |
| (Eq.1) | $[\text{dien}\cdot Fe—4H_2O]^{2+}$ | −1893.665763 | 0.005989 |
| | $[\text{dien}\cdot Fe—5H_2O]^{2+}$ | −1970.111196 | |
| | $[\text{dien}\cdot Fe—6H_2O]^{2+}$ | −2046.555322 | |
| | $[\text{dien}\cdot 2H_2O]$ | −477.306018 | |
| | $[\text{dien}\cdot 3H_2O]$ | −553.747647 | |
| | $[\text{dien}\cdot 4H_2O]$ | −630.193115 | |
| D102 complexation | $[Fe\cdot 6H_2O]^{2+}$ | −1722.106539 | |
| neutral environment | $[D102\cdot Fe—4H_2O]^{2+}$ | −2447.850871 | 0.005803 |
| (Eq.2) | $[D102\cdot Fe—5H_2O]^{2+}$ | −2524.296231 | |
| | $[D102\cdot Fe—6H_2O]^{2+}$ | −2600.741175 | |
| | $[D102\cdot 2H_2O]$ | −1031.485547 | |
| | $[D102\cdot 3H_2O]$ | −1107.93013 | |
| | $[D102\cdot 4H_2O]$ | −1184.377994 | |
| D102 complexation | $[Fe(OH)_2\cdot 4H_2O]$ | −1721.189904 | 0.006365 |
| basic environment | $[D102\cdot 2H_2O]$ | −1031.485547 | |
| (Eq.3) | $[D102\cdot Fe(OH)_2\cdot 4H_2O]$ | −2599.799515 | |

[%]Hartree is twice the energy of a hydrogen atom and corresponds to 2625.4996 kJ/mol.

*ZPE = Zero Point Energy 2,4,6-tris(3,4-dihydro-2H-pyrrol-2-yl)pyridine is therefore a much stronger complexing agent for $Fe^{2+}$ than diethylenetriamine. Adopting a similar value of $\Delta G^0-\Delta U^0$ for 2,4,6-tris(3,4-dihydro-2H-pyrrol-2-yl)pyridine as for diethylenetriamine; i.e. factoring both $T\Delta S^0$ and the computational error μ, it can be estimated for 2,4,6-tris(3,4-dihydro-2H-pyrrol-2-yl)pyridine:

$$\Delta G^0_{D_{102}} = \Delta U^0_{D_{102}} + T\Delta S^0_{dien} + \mu =$$

$$\Delta U^0_{D_{102}} + \Delta G^0_{dien} - \Delta U^0_{dien} = (-93.6 - 36.1 + 62.0)\text{kJ/mol}$$

$$\Delta G^0_{D_{102}} = -67.8 \text{ kJ/mol}$$

$$pK = \frac{\Delta G^0_{D_{102}}}{\ln(10)RT} \approx 11.5$$

where $$R = 8.3144\frac{J}{\text{Kmol}},\ T = 298K \Rightarrow RT = 2.478 \text{ kJ/mol},\ \ln(10) = 2.303$$

For the complexation reaction of 2,4,6-tris(3,4-dihydro-2H-pyrrol-2-yl)pyridine (D102) with $Fe(OH)_2$, i.e. for the reaction scheme:

$$[D102 \cdot Fe(OH)_2 \cdot 4H_2O] \Rightarrow D102 \cdot [Fe(OH)_2 \cdot 4H_2O]$$

we similarly obtain:

$$\Delta U = (-2599.799515 + 1721.189904 + 1031.48554 - 2 * 76.44622 + 0.006365) \text{ Hartree} = -0.01014 \text{ Hartree} = -27 \text{ kJ/mol}$$

Accordingly, $Fe(OH)_2$ is a weak binder.

Finally, short time (500 femtoseconds) QM dynamics were conducted for each of the main species with the maximum number of explicit water reported above to check whether different nuclear configurations are available and relevant to the thermodynamic properties of the system. The statistical analysis of the molecular dynamic's frames did not reveal any important correction to the above reported results.

CONCLUSIONS

The following reaction was thermodynamically favored by 93.7 kJ/mol:

$$[D102 \bullet 2H_2O] + [Fe \bullet 6H_2O]^{2+} \longleftrightarrow [D102 \bullet Fe — 6H_2O]^{2+} + 2\ H_2O$$

The pK of this reaction was determined to be:

$$K_{eq} = \frac{[Fe^{2+}][D102]}{[D102Fe^{2+}]} = 10^{-11}$$

According to this pK value, it will require at least 10 μM 2,4,6-tris(3,4-dihydro-2H-pyrrol-2-yl)pyridine for complexation of a 1 μM $Fe^{2+}$ solution.

Example 10: Synthesis of 2,4,6-tris(3,4-dihydro-2H-pyrrol-2-yl)pyridine-Zn

[Batch 1] Compound 9 from Example 5 above (1.4 g, 0.005 mol, 1 eq) was dissolved in EtOH (30 ml) with effective stirring and heating to 50-55° C. to obtain a clear yellow solution. $ZnCl_2$ (0.75 g, 0.0055 mol, 1.1 eq) was dissolved in EtOH (15 ml) and it was added dropwise to the first hot solution. A white solid was precipitated. The suspension was stirred for a further 30 min at 50° C. and then it was cooled to RT (20° C.). The solid was filtered, washed with EtOH (5 ml), and dried under a high vacuum Yield: 2.0 g (93%). Solubility tests were conducted with this batch.

Figure 27:
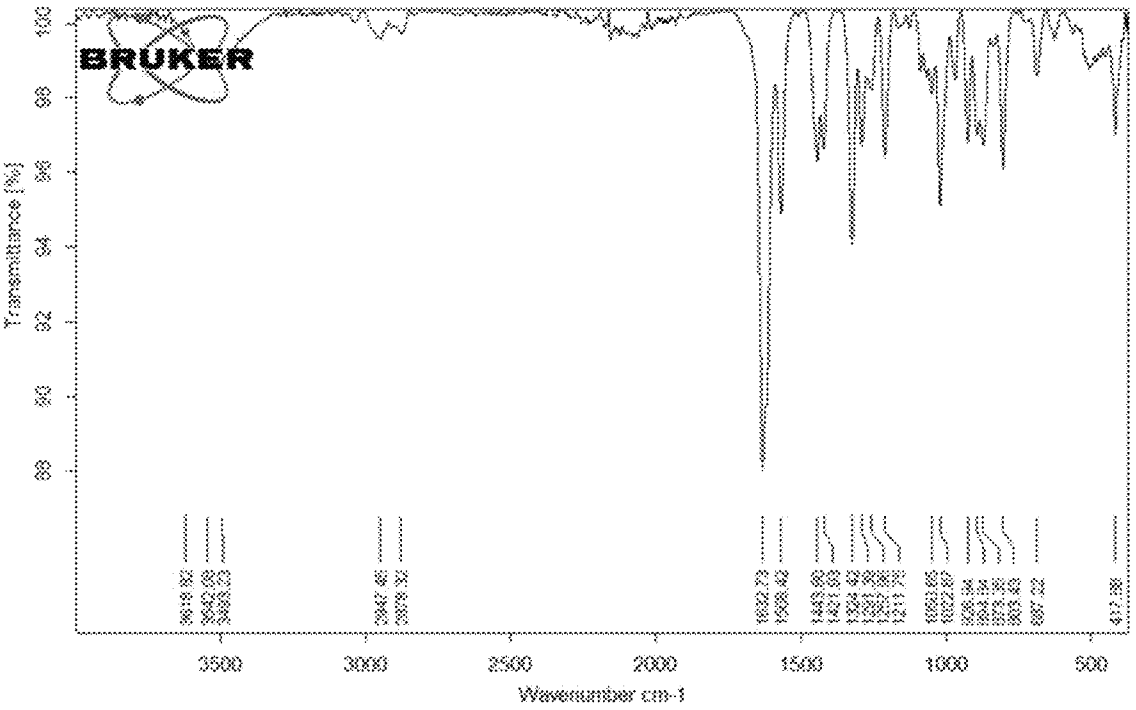
FIG. 27 shows IR (infrared) spectrum for a lot of $C_{17}H_{20}N_4ZnCl_2$ synthesized according to the protocol set forth in Example 10, Batch 2.
Figure 30:
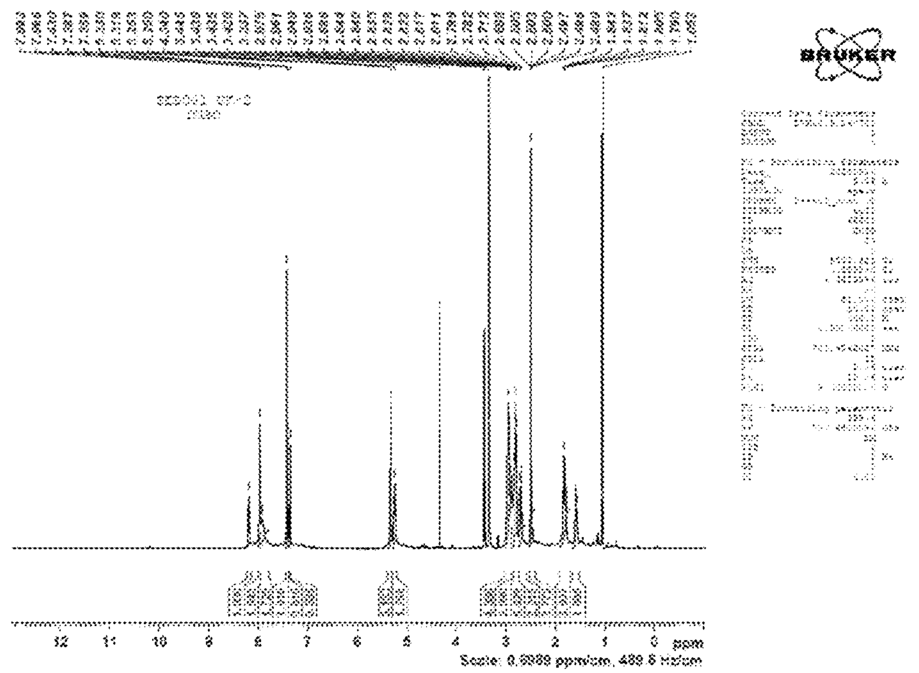
FIG. 30 shows $^1$H NMR spectrum for a lot of $C_{17}H_{20}N_4ZnBr_2$ synthesized according to the protocol set forth in Example 10, Batch 3.
Figure 31:
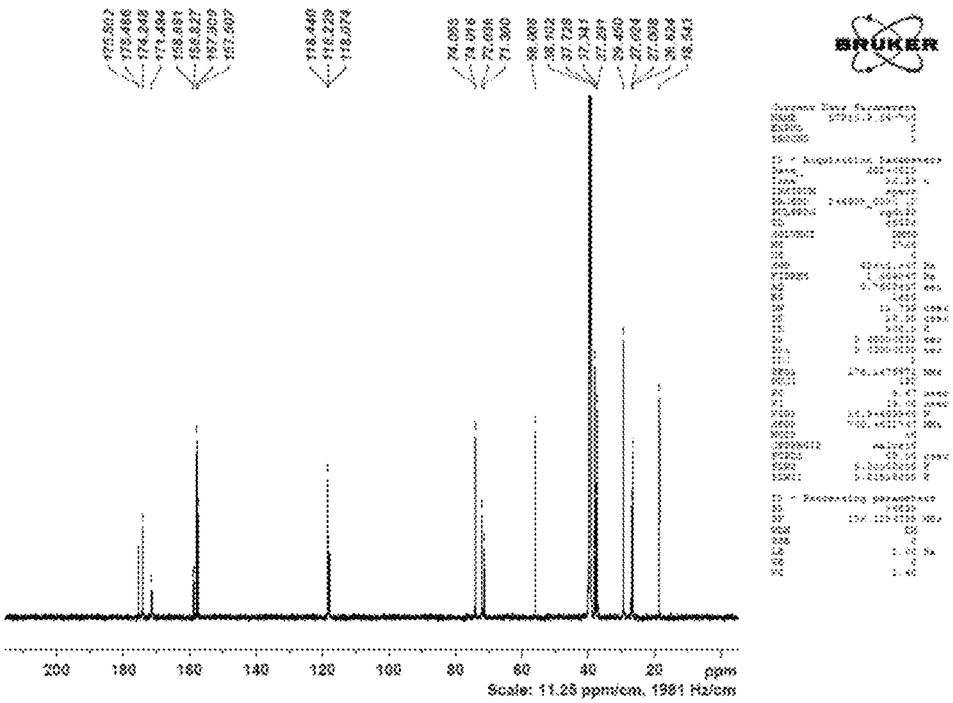
FIG. 31 shows $^{13}$C NMR spectrum for a lot of $C_{17}H_{20}N_4ZnBr_2$ synthesized according to the protocol set forth in Example 10, Batch 3.

[Batch 2] Compound 9 from Example 5 above (4.2 g, 0.015 mol, 1 eq) was dissolved in EtOH (100 ml) with effective stirring and heating to 50° C. to obtain a clear yellow solution. $ZnCl_2$ (2.5 g, 0.018 mol, 1.2 eq) was dissolved in EtOH (45 ml) and it was added dropwise to the first hot solution. A white solid was precipitated. The suspension was stirred for a further 30 min at 50° C. and then it was cooled to RT (20° C.). The solid was filtered, washed with EtOH (20 ml), and dried under a high vacuum on a yield of 5.36 g (80%). The material was subjected to NMR, elemental analysis, FTIR, HRMS, and ICP analysis. FTIR, $^1$H-NMR and $^{13}$C-NMR results in given in FIGS. 27, 30 and 31, respectively.

Figure 26:
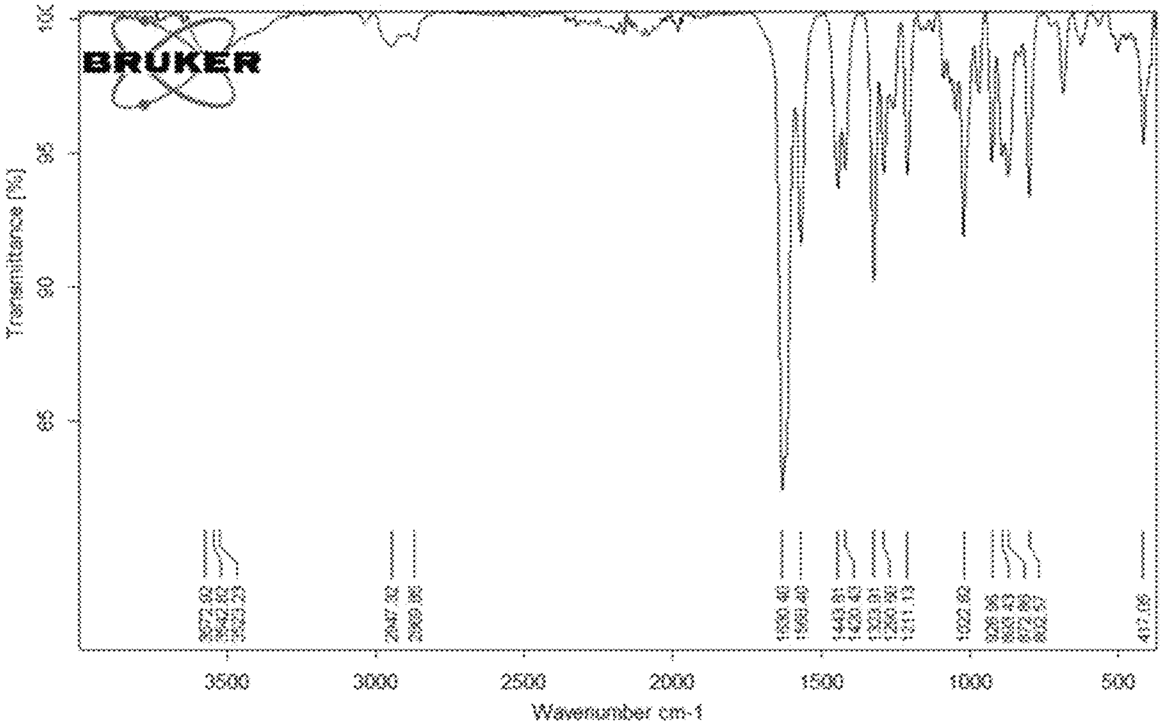
FIG. 26 shows IR (infrared) spectrum for a lot of $C_{17}H_{20}N_4ZnBr_2$ synthesized according to the protocol set forth in Example 10, Batch 3.
Figure 32:
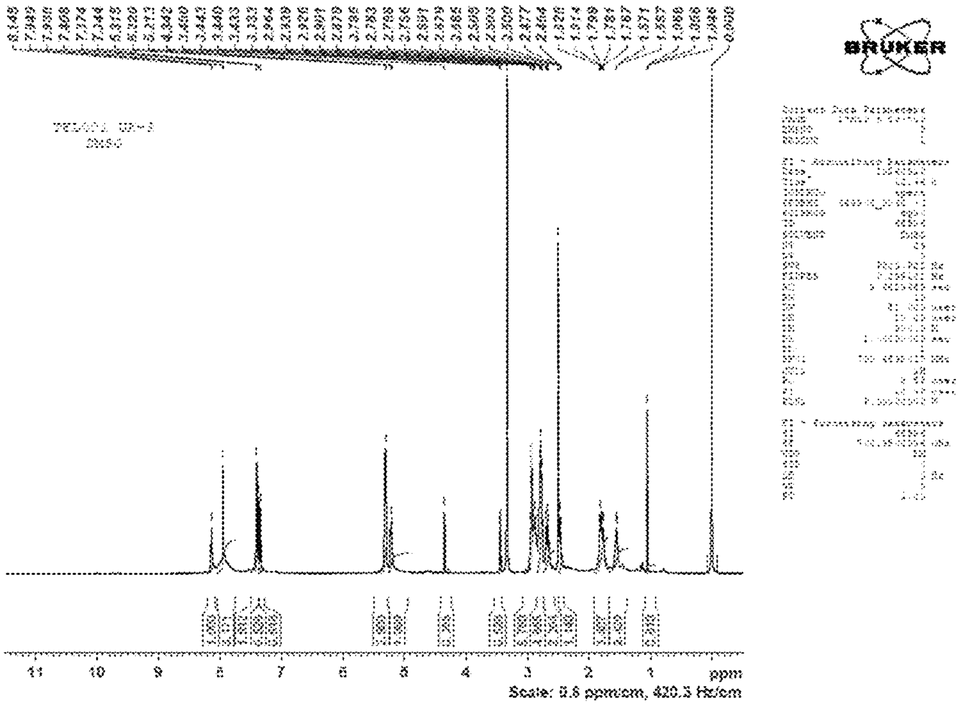
FIG. 32 shows $^1$H NMR spectrum for a lot of $C_{17}H_{20}N_4ZnCl_2$ synthesized according to the protocol set forth in Example 10, Batch 2.
Figure 33:
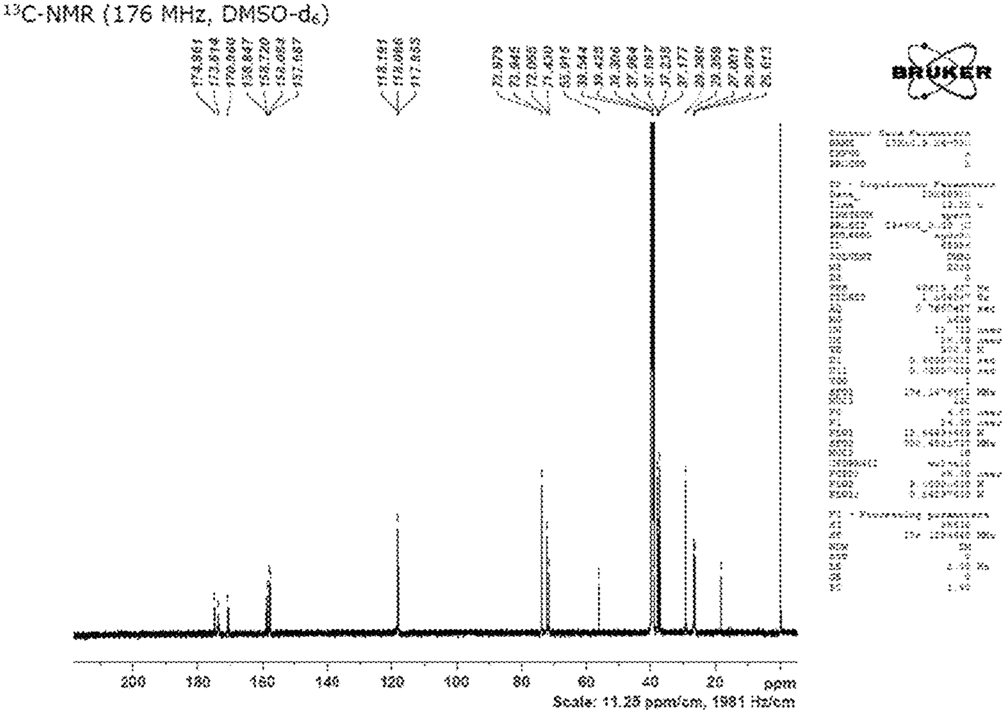
FIG. 33 shows $^{13}$C NMR spectrum for a lot of $C_{17}H_{20}N_4ZnCl_2$ synthesized according to the protocol set forth in Example 10, Batch 2.

[Batch 3] Compound 9 from Example 5 above (1.4 g, 0.005 mol, 1 eq) was dissolved in EtOH (30 ml) at effective stirring and heating to 50-55° C. to obtain a clear yellow solution. $ZnBr_2$ (1.24 g, 0.0055 mol, 1.1 eq) was dissolved in EtOH (15 ml) and it was added dropwise to the first hot solution. A white solid was precipitated. The suspension was stirred for 30 min at 50° C. and it was cooled to RT (20° C.). The solid was filtered, washed with EtOH (5 ml), and dried. Yield: 2.5 g (95%). The material was subjected to NMR, elemental analysis, FTIR, HRMS, and ICP analysis. FTIR, $^1$H-NMR and $^{13}$C-NMR results in given in FIGS. 26, 32 and 33, respectively.

Based on literature, the following bands of the main functional groups illustrate the main differences between the complexes vs. the ligand Compound 9 (see Table 10 below).

TABLE 10

| | Experimental results [cm$^{-1}$] | | |
|---|---|---|---|
| Functional group | Compound 9 | Batch 3 | Batch 2 |
| NH [a] | — | 3572.92 | 3618.82 |
| | | 3542.82 | 3542.08 |
| | | 3523.23 | 3493.23 |
| C—H (aromatic, alkene) | 2946.40 | 2947.32 | 2947.45 |
| | 2868.12 | 2869.85 | 2878.32 |
| C═N (imine/pyridine) and C═C [a,b] | 1618.43 | 1630.40 | 1632.73 |
| | 1601.70 | 1568.40 | 1568.42 |
| | 1560.45 | | |
| Zn—X [c] | — | 417.05 | 417.88 |

[a] Nat. Sci. 2007,41,158;
[b] Inorganica Chimica Acta, 1974,9,51;
[c] Burapha University International Conference (July 2013).

The spectra of the complexes (Batches 3 and 2) are very similar. Additionally, both complexes show similarities to the ligand itself. The observed shifts in bands and changes in intensity ratios compared to the ligand (~2800-2900 cm$^{-1}$ and 3550-3600 cm$^{-1}$) strongly suggest the formation of a complex.

Elemental analysis for C, H, N atoms was performed at Bar Ilan University, with Elementar UNICUBE, micro elemental analyzer. Tables 11 and 12 below present the results, the molecular formula L-Zn—$X_2$ per batch was examined for fitting.

TABLE 11

| Compound 9 | | | | | |
|---|---|---|---|---|---|
| Name | Weight [mg] | Molecular formula | N [%] | C [%] | H [%] |
| Theoretical | | $C_{17}H_{20}N_4$ | 19.98 | 72.83 | 7.19 |
| Experimental | 4.073 | | 17.6 | 67.4 | 7.326 |

TABLE 12

| Compound 9-Zn | | | | | |
|---|---|---|---|---|---|
| Name | Weight [mg] | Molecular formula | N [%] | C [%] | H [%] |
| Theoretical | | $C_{17}H_{20}N_4ZnBr_2$ | 11.08 | 40.39 | 3.99 |
| Experimental | 4.364 | Batch 3 | 9.03 | 34.3 | 3.905 |
| Theoretical | | $C_{17}H_{20}N_4ZnCl_2$ | 13.45 | 49.01 | 4.84 |
| Experimental | 4.237 | Batch 2 | 10.97 | 41.16 | 4.641 |

Based on the elemental analysis, the ligand appears to contain impurities, as indicated by deviations in the carbon and nitrogen measurements (Table 11). The impurities likewise impacted the results observed in the complexes (Table 12).

JCP measurements were performed at Bar Ilan University with SPECTRO ARCOS JCP-GES Multi-view FHX22. About 160 mg from each complex was weighed and analyzed for Zn, Br, and Cl content (% w). Tables 13-15 below present the JCP results.

TABLE 13

| Batch | Zn (ppm) | % Zn | Br (ppm) | % Br | Cl (ppm) | % Cl |
|---|---|---|---|---|---|---|
| 3 | 171271.9 | 17.13 | 356743.7 | 35.67 | | |
| 2 | 210911.4 | 21.09 | | | 214424 | 21.44 |

TABLE 14

| Batch | Weight | Zn in sample | Br in sample | Cl in sample |
|---|---|---|---|---|
| 3 | 160 mg | 27 mg | 57 mg | |
| | 1 g | 171 mg | 357 mg | |
| 2 | 160 mg | 34 mg | | 34 mg |
| | 1 g | 211 mg | | 214 mg |

Number of moles of each element and the ratio calculation according to the ICP results are given in Table 15 below:

TABLE 15

| | N (mol) | | | | Equimolar ratio | | | |
|---|---|---|---|---|---|---|---|---|
| Batch | Ligand | Zn | Br | Cl | Ligand | Zn | Br | Cl |
| 3* | 0.269 | 0.419 | 0.722 | — | 1.0 | 1.5 | 2.7 | — |
| 2** | 0.328 | 0.516 | — | 0.968 | 1.0 | 1.6 | — | 3.0 |

*Mw (Batch 3) = Ligand (280) + Zn (64) + 2Br (2 * 79) = 502
**Mw (Batch 2) = Ligand (280) + Zn (64) + 2Cl (2 * 35) = 414

According to the calculated equimolar ratio of each complex's components, the ICP results align with the elemental analysis suggestive outcome of the following molecular composition of L-Zn—$X_2$.

HRMS analysis was conducted at Bar Ilan University, with Q-TOF 6545 (High Resolution) Agilent, by dissolving the complexes in a 1:1 (v/v) acetonitrile/water mixture and directly injecting them into the ESI-QTOF instrument. For both complexes, the following m/z were detected:

$$m/z\text{: 281-free Ligand}$$

$$m/z\text{: 425 and 379-}L\text{-Zn-}X(X = \text{Br and Cl respectively})$$

$$m/z\text{: 705 and 659-}L_2\text{-Zn-}X(X = \text{Br and Cl respectively})$$

$$m/z\text{: 930 and 797-}L_2\text{-Zn-}X3(X = \text{Br and Cl respectively})$$

Figure 28:
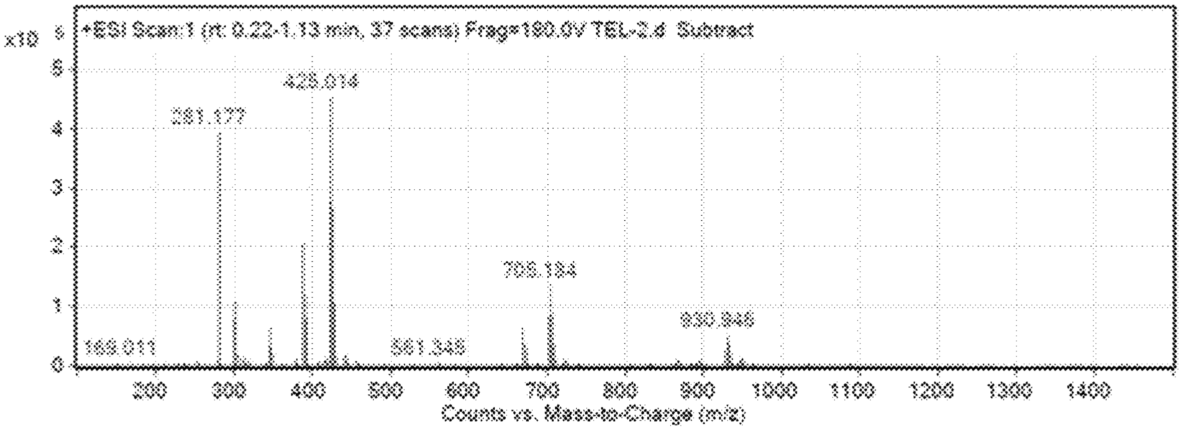
FIG. 28 shows HRMS for a lot of $C_{17}H_{20}N_4ZnBr_2$ synthesized according to the protocol set forth in Example 10, Batch 3.
Figure 29:
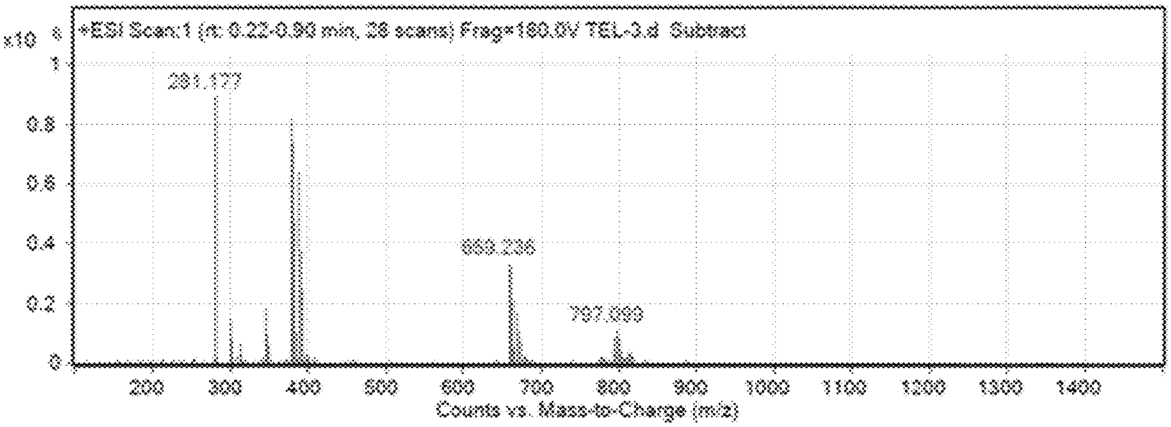
FIG. 29 shows HRMS for a lot of $C_{17}H_{20}N_4ZnCl_2$ synthesized according to the protocol set forth in Example 10, Batch 2.

There are some uncertainties in the HRMS analysis regarding the stability of complexes in their diluent and in the ionization process. Nonetheless, the presence of Zn and each chlorine/bromine was evident in the complexes as shown in the FIRMS (FIGS. 28-29).

Based on the FIRMS results (FIG. 28), the structures present in Batch 3 appear to be:

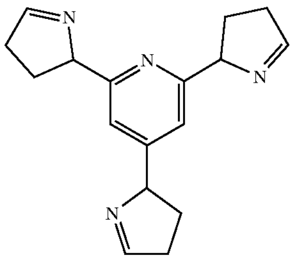

$C_{17}H_{20}N_4$
Exact Mass: 280.2
m/z: 280.2 (100%)
281.2 (20.1%)

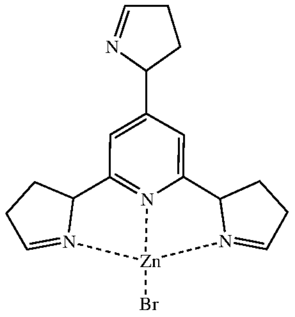

$C_{17}H_{20}BrN_4Zn$
Exact Mass: 423.0
m/z: 425 (100%)
423.0 (63.97%), 427.0 (63.3%)

-continued
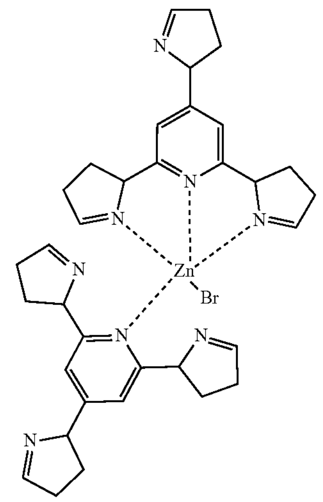
$C_{34}H_{40}BrN_8Zn$
Exact mass: 703.2
m/z: 705.2 (100%)
707.2 (67.7%), 703.2 (61.5%), 706.2 (44.0%)
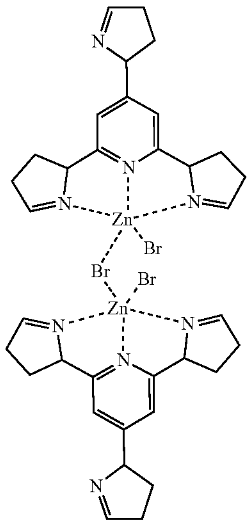
$C_{34}H_{40}Br_3N_8Zn_2$
Exact Mass: 925.0
m/z: 930.9 (100%)
928.9 (91.7%), 932.9 (77.6%), 926.9 (50.8%)
According to the HRMS results (FIG. 29), the structures present in Batch 2 appear to be:
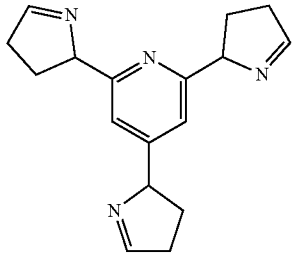
$C_{17}H_{20}N_4$
Exact Mass: 280.2
m/z: 280.2 (100%)
281.2 (20.1%)
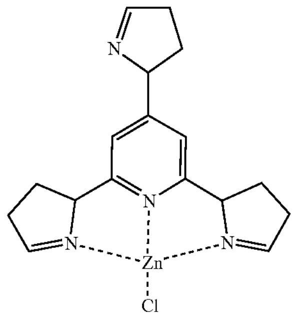
$C_{17}H_{20}ClN_4Zn$
Exact Mass: 379.1
m/z: 379.1 (100%), 381.1 (91.2%),
383.1 (60.3%), 382.1 (26.5%)
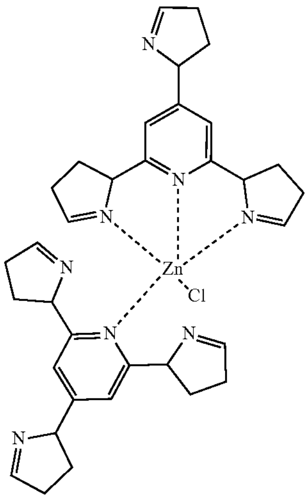
$C_{34}H_{40}ClN_8Zn$
Exact mass: 659.2
m/z: 659.2 (100%)
661.2 (97.2%), 663.2 (67.4%)

-continued

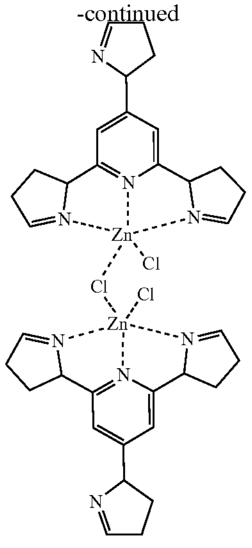

$C_{34}H_{40}Cl_3N_8Zn_2$

Exact Mass: 793.1 m/z: 797.1 (100%)

799.1 (80.9%), 795.1 (79.7%)

What is claimed is:

1. A compound having a structure according to Formula Ia or Formula Ib set forth below:

Formula Ia

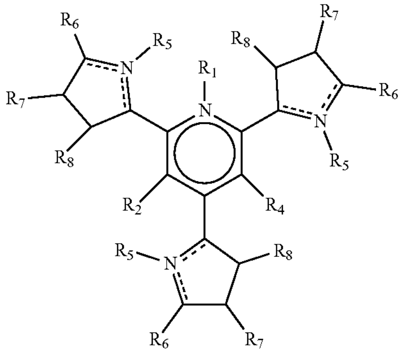

Formula Ib

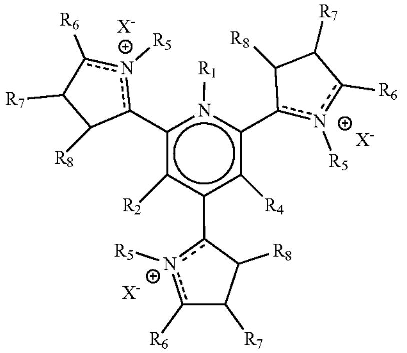

or a pharmaceutically acceptable ester or solvate thereof, wherein $X^-$ is an ion of an acid forming a pharmaceutically acceptable salt, wherein $R_1$, $R_2$, $R_4$, $R_5$, $R_6$, $R_7$, and $R_8$ are independently selected from the group consisting of nothing, H, OH, protected hydroxyl, alkyl, alkenyl, alkynyl, acyl, aryl, heteroaryl, cycloalkyl, and heterocycle; wherein the alkyl, alkenyl, alkynyl or acyl is optionally substituted with one or more substituents independently selected from the group consisting of halogen, —OH, alkyl, —O-alkyl, $NR^AR^B$, —S-alkyl, —SO-alkyl, —$SO_2$-alkyl, alkenyl, alkynyl, aryl, heteroaryl, cycloalkyl, and heterocycle; wherein $R^A$ and $R^B$ are each independently selected from hydrogen and $C_{1-4}$ alkyl; wherein the aryl or heteroaryl, whether alone or as part of a substituent group, is optionally substituted with one or more substituents independently selected from the group consisting of halogen, —OH, alkyl, —O-alkyl, —COOH, —C(O)—$C_{1-4}$ alkyl, —C(O)O—$C_{1-4}$ alkyl, $NR^CR^D$, —S-alkyl, —SO-alkyl and —$SO_2$-alkyl; wherein $R^C$ and $R^D$ are each independently selected from hydrogen and $C_{1-4}$ alkyl; and wherein ⚋ represents a single bond or a double bond with the proviso that within a five-membered ring, one ⚋ is a single bond and the other ⚋ is a double bond.

2. A compound having a structure according to Formula Ia or Formula Ib set forth below:

Formula Ia

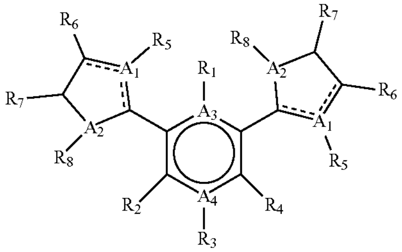

Formula Ib

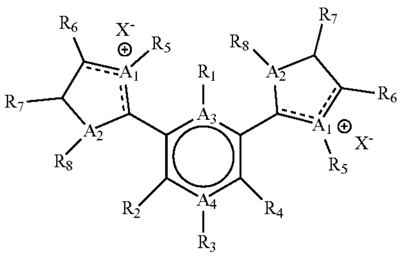

or a pharmaceutically acceptable ester or solvate thereof, wherein $X^-$ is an ion of an acid forming a pharmaceutically acceptable salt, where $A_1$, $A_2$, $A_3$, and $A_4$ are independently selected from nitrogen and carbon; provided that at least one of $A_3$ or $A_4$ is nitrogen, wherein $R_1$, $R_2$, $R_3$, $R_4$, $R_5$, $R_6$, $R_7$, and $R_8$ are independently selected from the group consisting of nothing, H, OH, protected hydroxyl, alkyl, alkenyl, alkynyl, acyl, aryl, heteroaryl, cycloalkyl, and heterocycle; wherein $R_1$ is nothing if $A_3$ is N; wherein $R_3$ is nothing if $A_4$ is N: wherein the alkyl, alkenyl, alkynyl or acyl is optionally substituted with one or more substituents independently selected from the group consisting of halogen, —OH, alkyl, —O-alkyl, $NR^AR^B$, —S-alkyl, —SO-alkyl, —$SO_2$-alkyl, alkenyl, alkynyl, aryl, heteroaryl, cycloalkyl, and heterocycle; wherein $R^A$ and $R^B$ are each independently selected from hydrogen and $C_{1-4}$ alkyl; wherein the aryl or heteroaryl, whether alone or as part of a substituent group, is optionally substituted with one or more substituents independently selected from the group consisting of halogen, —OH, alkyl, —O-alkyl, —COOH, —C(O)—$C_{1-4}$ alkyl, —C(O)O—$C_{1-4}$ alkyl, $NR^CR^D$, —S-alkyl, —SO-alkyl and —$SO_2$-alkyl; wherein $R^C$ and $R^D$ are each independently selected B from hydrogen and $C_{1-4}$ alkyl; wherein - - - represents a single bond or a double bond with the proviso that within a five-membered ring, one - - - is a single bond and the other - - - is a double bond; and provided that at least one of $R_2$ and/or $R_4$ has the structure according to Formula IIa or Formula IIb:

Formula IIa

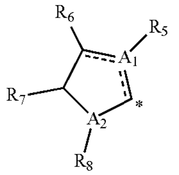

Formula IIb

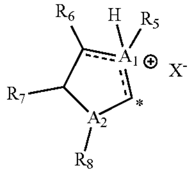

wherein in Formula IIa and Formula IIb $X^-$, - - - , $A_1$, $A_2$, $R_5$, $R_6$, $R_7$, and $R_8$ are defined as above and the * indicates the point of attachment of Formula IIa and/or Formula IIb to Formula Ia or Formula Ib.

3. The compound of claim 2, wherein $A_1$ and $A_4$ are N, and $R_3$ is nothing.

4. The compound of claim 3, wherein $A_2$ is C.

5. The compound of claim 3, wherein $A_3$ is N.

6. The compound of claim 5, wherein $A_2$ is C.

7. A compound having a structure selected from the group consisting of:

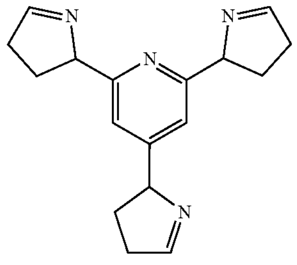

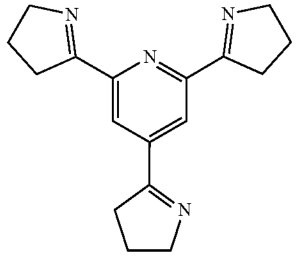

-continued

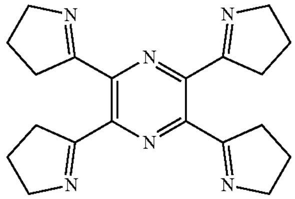

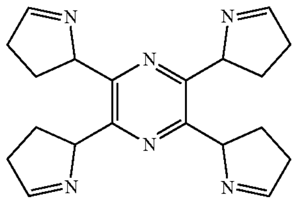

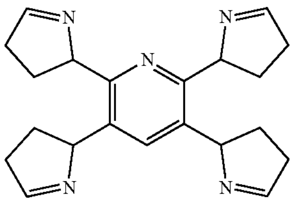

and

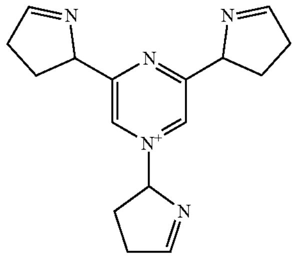

or a pharmaceutically acceptable salt-ester or solvate thereof.

8. The compound of claim 7 having the structure:

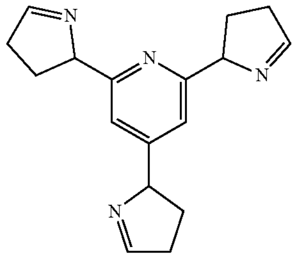 [SMILES: C1=NC(c2cc(C3CCC=N3)nc(C3CCC=N3)c2)CC1]

2,4,6-tris(3,4-dihydro-2H-pyrrol-2-yl)pyridine or a pharmaceutically acceptable salt or solvate thereof.

9. The compound of claim 1 which is a pharmaceutically acceptable salt having a structure according to Formula VIa, Formula VIb, Formula VIc or any combination thereof:

Formula VIa

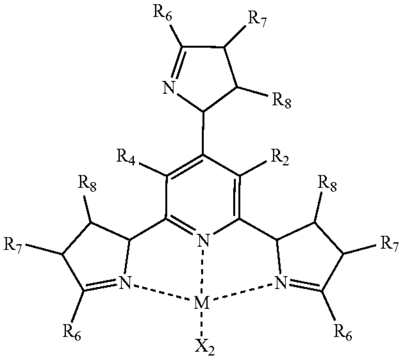

Formula VIb

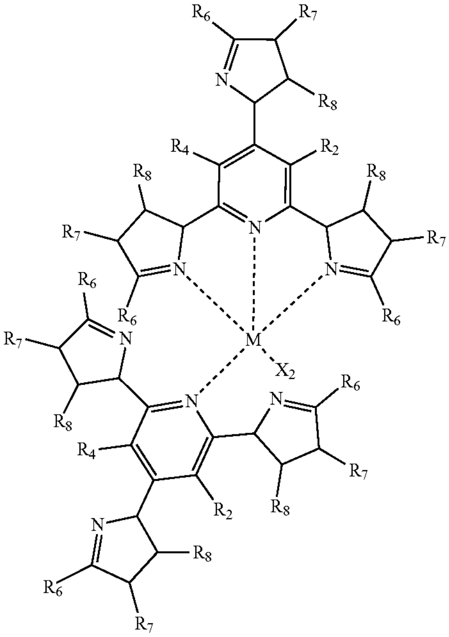

-continued

Formula VIc

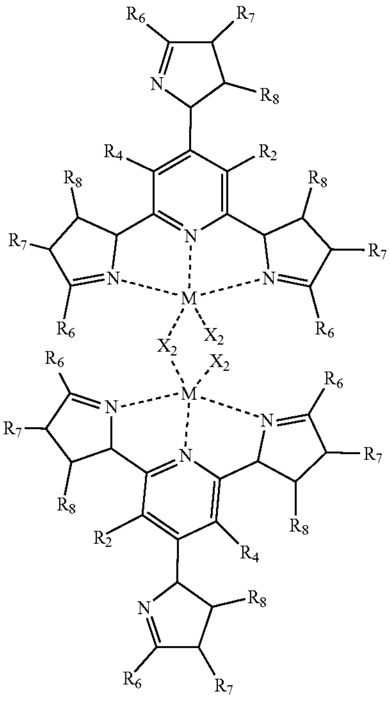

wherein each $X_2$ is independently an ion of an acid forming a pharmaceutically acceptable salt, and each M is independently a transition metal selected from the group consisting of scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, and gold.

10. The compound of claim 9 wherein each M is independently zinc or silver.

11. The compound of claim 9 having a structure selected from the group consisting of:

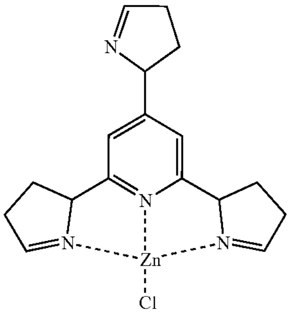

-continued
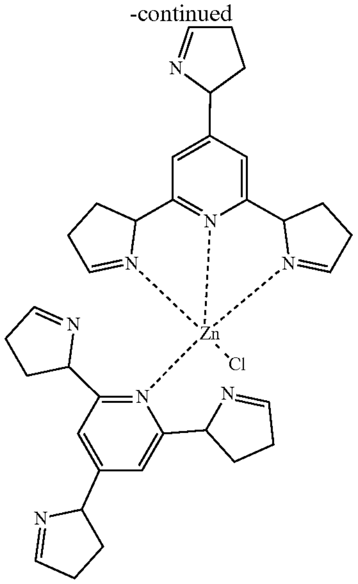
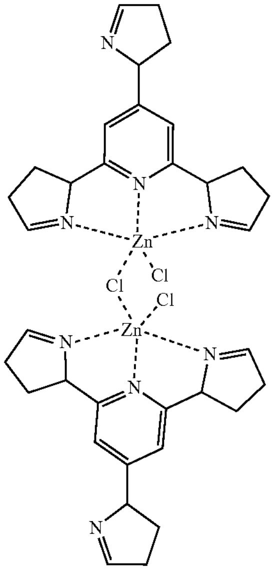
and a combination thereof.
12. The compound of claim 9 having a structure selected from the group consisting of:
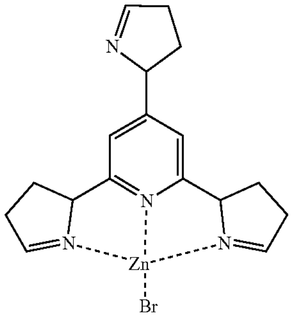
-continued
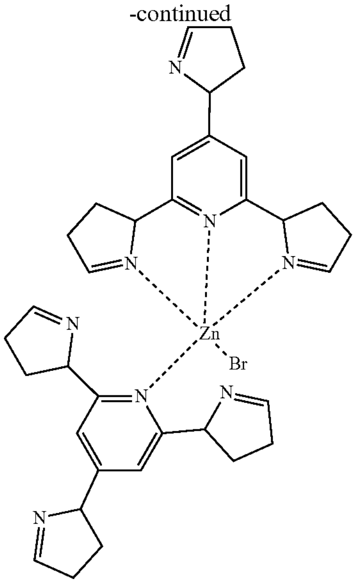
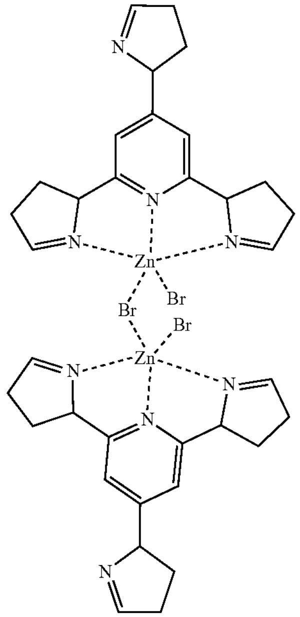
and a combination thereof.
13. A pharmaceutical composition comprising an effective amount of a compound claim 1 and a pharmaceutically acceptable vehicle therefor.
* * * * *